US008614298B2

(12) United States Patent
Shafer et al.

(10) Patent No.: US 8,614,298 B2
(45) Date of Patent: *Dec. 24, 2013

(54) HUMANIZED ANTI-AMYLOID BETA ANTIBODIES

(75) Inventors: Lisa Lynn Shafer, Stillwater, MN (US); Francis Joseph Carr, Aberdeenshire (GB); James Peter Gregson, Essex (GB); Dawn Ann Bembridge, Hertfordshire (GB); Tim Jones, Cambridgeshire (GB)

(73) Assignee: Medtronic, Inc., Minneapolis, MN (US)

( * ) Notice: Subject to any disclaimer, the term of this patent is extended or adjusted under 35 U.S.C. 154(b) by 240 days.

This patent is subject to a terminal disclaimer.

(21) Appl. No.: 13/052,597

(22) Filed: Mar. 21, 2011

(65) Prior Publication Data

US 2011/0177076 A1    Jul. 21, 2011

Related U.S. Application Data

(60) Division of application No. 12/323,682, filed on Nov. 26, 2008, now Pat. No. 7,931,899, and a continuation-in-part of application No. 12/120,269, filed on May 14, 2008.

(60) Provisional application No. 60/990,401, filed on Nov. 27, 2007, provisional application No. 60/917,911, filed on May 14, 2007, provisional application No. 60/984,775, filed on Nov. 2, 2007.

(51) Int. Cl.
*C07K 16/46* (2006.01)
*C07K 16/18* (2006.01)
*A61K 39/395* (2006.01)
*A61M 5/14* (2006.01)
*A61K 9/08* (2006.01)

(52) U.S. Cl.
USPC ............... 530/387.3; 530/388.1; 530/388.25; 530/387.1; 604/891.1; 424/133.1; 424/139.1; 424/141.1

(58) Field of Classification Search
None
See application file for complete search history.

(56) References Cited

FOREIGN PATENT DOCUMENTS

| WO | WO 02/46237 | 6/2002 |
|----|----|----|
| WO | WO 03/016466 | 2/2003 |
| WO | WO 03/070760 | 8/2003 |
| WO | WO 2004/029630 | 4/2004 |
| WO | WO 2006/066171 | 6/2006 |
| WO | WO 2006/081171 | 8/2006 |
| WO | WO 2007/050359 | 5/2007 |
| WO | WO 2007/064972 | 6/2007 |
| WO | WO 2007/113172 | 10/2007 |

OTHER PUBLICATIONS

PCT Search Report and Written Opinion dated Nov. 4, 2009.

*Primary Examiner* — Kimberly A Ballard
(74) *Attorney, Agent, or Firm* — Mueting Raasch & Gebhardt PA

(57) ABSTRACT

Humanized anti-Aβ antibodies derived from a murine antibody directed to a N-terminal epitope of Aβ are described. The humanized antibodies have reduced or no human T cell epitopes and bind Aβ with an affinity similar to that of the murine antibody.

16 Claims, 21 Drawing Sheets

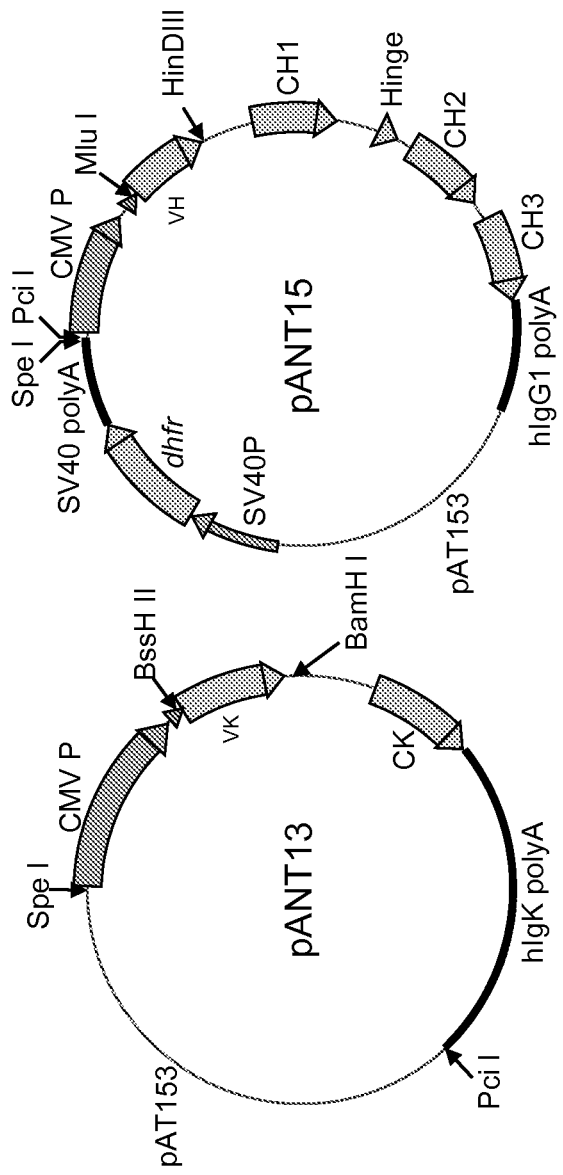
Figure 1: Light Chain and Heavy Chain Expression Vectors.

FIGURE 2: SEQUENCES OF MOUSE (CHIMERIC), DEIMMUNIZED ("DeI"), HUMANIZED ("GRAFTED") AND COMPOSITE HUMAN ANTIBODY ("CHAB") VARIANTS OF 6E10
(****=CDRs)

Heavy Chain Seqs:

```
                  **********           ******************                                                    **********                 SEQ_ID_NO:
Mouse:   EVQLQQSGAELVKPGASVKLSCTASGFNIKDIYIHWVKQREQGLEWIGRIDPVNVNTRYDSRFQGKATITSDASSNTAYLHLNSLTSEDTAVYYCSRSYYNGRRFTYWGQGTLVTVSA  (36)
DeI:     EVQLQQSGAELVKPGASVKVSCTASGFNIKDIYIHWVKQREQGLEWIGRIDPVNVNTRFDSRFQGKATITSDASSNTAYMELSSLRSEDTAVYYCSRSYYNGRRFTYWGQGTLVTVSA  (42)
GRAFT1:  QVQLVQSGAEVKKPGASVKVSCKASGFNIKDLYIHWVRQAPGQGLEWMGRIDPVNVGRFDSRFQGRVTMTRDTSTSTVYMELSSLRSEDTAVYYCARSYYNGRRFTYWGQGTLVTVSS  (44)
GRAFT2:  QVQLVQSGAEVKKPGASVKVSCTASGFNIKDLYIHWVRQAPGQGLEWMGRIDPVNVNTRFDSRFQGRVTMTRDTSTSTVYMELSSLRSEDTAVYYCARSYYNGRRFTYWGQGTLVTVSS  (46)
CHAB1:   EVQLVQSGAELKKPGASVKVSCTASGFNIKDIYIHWVRQAPGQRLEWIGRIDPVNVNTRYDSRFQGRATITSDASTNTAYMELSSLRSEDTAVYYCSRSYYNGRRFTYWGQGILVTVSS  (47)
CHAB2:   EVQLVQSGAEVKKPGASVKVSCTASGFNIKDLYIHWVRQARGQRLEWIGRIDPVNVNTRYDSRFQGRATITSDASTNTAYMELSSLRSEDTAVYYCSRSYYNGRRFTYWGQGILVTVSS  (48)
CHAB3:   QVQLVQSGAEVKKPGASVKVSCTASGFNIKDLYIHWVRQARGQRLEWIGRIDPVNVNTRYDSRFQGRATITSDASTNTAYMELSSLRSEDTAVYYCSRSYYNGRRFTYWGQGILVTVSS  (49)
CHAB4:   QVQLVQSGAEVKKPGASVKVSCTASGFNIKDLYIHWVRQARGQRLEWIGRIDPVNVNTRYDSRFQGRATITSDASTNTAYMELSSLRSEDTAVYYCSRSYYNGRRFTYWGQGILVTVSS  (50)
CHAB5:   QVQLVQSGAEVKKPGASVKVSCTASGFNIADLYIHWVRQARGQRLEWIGRIDPVNVNTRYDSRFQGRVTITSDASTNTAYMELSSLRSEDTAVYYCSRSYYNGRRFTYWGQGILVTVSS  (51)
```

Light Chain Seqs:

```
                    **************          ********                  **********                SEQ_ID_NO:
Mouse:   DIVMTQTPSSLTVTAGEKVTIICKASQSVLSSGNQKNYLTWYQQKPGQPPKLLIYWASIRESGVPDRFTGSGSGTFFTLTISSVQAEDLAVYYCQNDYNYPFTFGGGTKLEIK  (37)
DeI:     DIVMTQSPSSLTVTAGEDAALICKASQSILSSGNQKNYLTWYQQKPGQPPKLLIYWASIRESGVPDRFTGSGSGTFFTLTISSVQAEDLAVYYCQNDYNYPFTFGGGTKLEIK  (43)
GRAFT:   DIVMTQSPLSLAVSLGDRATINCKASQSLLSSGNQKNYLTWYQQKPGQAPRKLLIYWASIRESGVPDRFSGSGSGTDFTLTISSLQAEDVAVYYCQNDYNYPFTFGQGTKLLIK  (45)
CHAB1:   DIVMTQSPDSLTVSLGERATINCKASQSLLSSGNQKNYLTWYQQKPGQPPKLLIYWASIRESGVPDRFSGSGSGTFFTLTISSLQAEDVAVYYCQNDYNYPFTFGQGTKLLIK  (52)
CHAB2:   DIVMTQSPSSLTASVGDRVTITCKASQSVLSSGNQKNYLTWYQQKPGQPPKLLIYWASIRESGVPDRFSGSGSGTFFTLTISSLQAEDVAVYYCQNDYNYPFTFGQGTKLLIK  (53)
CHAB3:   DIVMTQSPSSLTASVGDRVTITCKASQSLLSSGNQKNYLTWYQQKPGQPPKLLIYWASIRESGVPDRFSGSGSGTDFTLTISSLQALDVAVYYCQNDYNYPFTFGQGTKLLIK  (54)
```

FIG. 3: Initial Sequences of Anti-Beta Amyloid (MDT-2007) Heavy and Light Chains (a) Heavy chain VH1

```
         10        20        30        40        50        60        70        80        90       100
GAGGTTCAGTTGGTGCAGTCTGGGGCTGAGCTTAAGAAGCCTGGGGCCTCAGTCAAGGTGTCCTGCAAGGTTTCTGGTTTCAACATTAAAGACACTTATA
 E  V  Q  L  V  Q  S  G  A  E  L  K  K  P  G  A  S  V  K  V  S  C  K  V  S  G  F  N  I  K  D  T  Y
                                              10                      20                      30

110       120       130       140       150       160       170       180       190       200
TACATTGGGTGAGGCAGGCCCCTGGACAGGGCCTGGAGTGGATTGGATGGATTGATCCTGAAAATGGTGATACTGAATATGCCCCGAAGTTCCAAGGCAG
 I  H  W  V  R  Q  A  P  G  Q  R  L  E  W  I  G  R  I  D  P  V  N  V  N  T  E  Y  D  S  P  R  G  R
                  40                              50  52 A                          60

210       220       230       240       250       260       270       280       290       300
GGCCACTATAACATCAGACGATCAGCAAGCACAGCTACATGGAACTGAGCAGCCTGACATCTGAAGATCTGCAGTCTATTACTGTGTTCTGTAGTCGTTAT
 A  T  I  T  S  D  T  S  S  N  T  A  Y  M  E  L  S  S  L  R  S  E  D  T  A  V  Y  Y  C  S  R  S  Y
          70                              80  82 A B C                      90

310       320       330       340       350       360
TACTAGGGTAGAGACGCTTTACTTACTGGGGCCAAGGGACTCTGGTCACTGTCTCTTCA (SEQ. ID. NO. 55)
 Y  -  G  R  R  P  F  Y  W  G  Q  G  T  L  V  T  V  S  S   (SEQ. ID. NO. 47)
 100 A  B  C                    110              113
```

CDR definitions and protein sequence numbering according to Kabat. CDR nucleotide and protein sequences are overlined Differences from murine reference sequence are underlined

FIG. 3:

(b) Light Chain Vκ1

```
         10        20        30        40        50        60        70        80        90       100
GACATTGTGATGACACAGTCTCCTGACTCCCTGACTGTGTCACTGGGAGAGAGGGCCACTATCAACTGCAAGGCCAGTCAGAGTGTTAAGTAGTGGAA
 D  I  V  M  T  Q  S  P  D  S  L  T  V  S  L  G  E  R  A  T  I  N  C  K  A  S  Q  S  L  S  S  G
                              10                        20                        27 A  B  C  D  E  F 110       120       130       140       150       160       170       180       190       200
ATCAAAAATACTTACTTGAACTGGTACCAACAGAAACCAGGGCAGGCTCCTAAATTGTTGATCTACTGGGCATCTATTAGGGAATCTGGGGTCCCTGATCG
 N  K  N  Y  L  T  W  Y  Q  Q  K  P  G  Q  A  P  K  L  L  I  Y  W  A  S  I  R  E  S  G  V  P  D  R
                 30                        40                        50                        60

210       220       230       240       250       260       270       280       290       300
CTTCAGTGGCAGTGGATCTGGGACAGATTTCACTCTCACCATCAGTTCTCTGCAGGCTGAAGACGTGGCAGTGTATTACTGTCAGCAAATGATTATAATTAT
 F  S  G  S  G  S  G  T  D  F  T  L  T  I  S  S  L  Q  A  E  D  V  A  V  Y  Y  C  Q  Q  M  D  Y  N  Y
                 70                        80                        90

310       320       330
CCCATTCACGTTCGGCCAAGGGACAAAGTTGGAAATAAAA (SEQ. ID. NO. 56)
 P  F  T  F  G  Q  G  T  K  L  E  I  K  (SEQ. ID. NO. 52)
                 100      106 A
```

CDR definitions and protein sequence numbering according to Kabat. CDR nucleotide and protein sequences are overlined Differences from murine reference sequence are underlined FIG. 4: Composite Human Antibody™ Sequence Variants of Anti-Beta Amyloid (MDT-2007) Heavy Chains (a) Heavy chain VH2

```
         10         20         30         40         50         60         70         80         90        100
GAGGTTCAGTTGGTGCAGTCTGGGGCAGAGGTTAAGAAGCCTGGGGCCTCAGTCAAGGTGTCCTGTAAGGCTTCTGGTTTCAACATTAAAGACACCTATA
 E  V  Q  L  V  Q  S  G  A  E  V  K  K  P  G  A  S  V  K  V  S  C  T  A  S  G  F  N  I  K  D  T  Y
                                              10                        20                        30
        110        120        130        140        150        160        170        180        190        200
TACATTGGGTGAAGGCAGGCCCAGGACAAGGGCTTGAGTGGATGGGAAGGCTTGAATGGATTGGAAGGATTGATCCTGAAAATGGTGATACTAAATACAATGAGAAGTTCAAGAGCAAG
 I  H  W  V  R  Q  A  R  G  Q  R  L  E  W  I  G  R  I  D  P  V  N  V  E  T  K  Y  N  E  K  F  K  S
                     40                    52 A                50                            60
        210        220        230        240        250        260        270        280        290        300
GCCACTATAACAGACAGCGATACGAGCATCCACCAGTCCACAGCTACAATACAGCCTGAGGAGTCTGAGGACACTGCCGTCTATTACTGTTCTAGGTCTTAT
 A  T  I  T  S  D  A  S  T  N  T  A  Y  N  E  L  S  S  L  R  S  E  D  T  A  V  Y  Y  C  S  R  S  Y
                70                 80   32 A B C                          90
        310        320        330        340        350        360
GGCCGGTTTCCCAGGCGACCTCTCCAGGTACTGGGGCCAAGGGACTCTGGTCACTGTCTCCTCA  (SEQ. ID. NO. 57)
 Y  G  R  F  P  R  D  L  S  R  Y  W  G  Q  G  T  L  V  T  V  S  S  (SEQ. ID. NO. 48)
     100 A B C                      110                 113
```

CDR definitions and protein sequence numbering according to Kabat. CDR nucleotide and protein sequences are overlined Differences from murine reference sequence are underlined FIG. 4:
(b) Heavy chain VH3

```
         10          20          30          40          50          60          70          80          90         100
CAGGTTCAGTTGGTGCAGTCTGGGGCAGAGGTGAAGAAGCCAGGGGCCTCAGTCAAGGTGTCCTGTACAGCTTCTGGTTTCAACATTAAAGACACCTATA
 Q  V  Q  L  V  Q  S  G  A  E  V  K  K  P  G  A  S  V  K  V  S  C  T  A  S  G  F  N  I  K  D  T  Y
                                                10                      20                      30

110         120         130         140         150         160         170         180         190         200
TACATTGGGTGAGACAGCAGGCCCAGGGCCAGGGACTGGAGTGGATTGGAAGGATTGATCCTGAAAATGGTGATATTGAATATGCTCCGAAGTTCCAGGGCAG
 I  H  W  V  R  Q  Q  A  R  G  Q  R  L  E  W  I  G  R  F  D  P  Y  N  T  R  Y  D  S  E  F  R  G  R
             40                      50   52 A               60

210         220         230         240         250         260         270         280         290         300
ATCACCATATACATCAGACGCATCCACCAATACAGCCTACATGGAGCTCAGCAGCCTGAGATCTGAGGACACTGCCGTCTATTACTGTTCTAGGTCTTAT
 A  T  I  T  S  D  A  S  T  N  T  A  Y  M  E  L  S  S  L  R  S  E  D  T  A  V  Y  Y  C  S  R  S  Y
     70                      80    82 A B C                          90

310         320         330         340         350         360
TACAATGGTAGAAGACGCTTTACTTACTGGGGCCAAGGGACTCTGGTCACTGTCTCTTCA (SEQ. ID. NO. 58)
 Y  N  G  R  R  R  F  T  Y  W  G  Q  G  T  L  V  T  V  S  S    (SEQ. ID. NO. 49)
         100 A B C                          110         113
```

CDR definitions and protein sequence numbering according to Kabat. CDR nucleotide and protein sequences are overlined Differences from murine reference sequence are underlined

FIG. 4:

(c) Heavy chain VH4

```
         10         20         30         40         50         60         70         80         90        100
CAGGTTCAGTTGGTGCAGTCTGGGGCTGAGGTGAAGAAGCCTGGGGCCTCAGTCAAGGTGTCCTGTACAGCTTCTGGTTTCAACATTAAAGACACCTATA
 Q  V  Q  L  V  Q  S  G  A  E  V  K  K  P  G  A  S  V  K  V  S  C  T  A  S  G  F  N  I  K  D  T  Y
                                                10                                  20                    30

110        120        130        140        150        160        170        180        190        200
TACATTGGGTCGAGGCAGGCCCAAGGACAGGGACTGGAGTGGATTGGAAGGATTGATCCTGCAAATGGTAATACTAAATATGATCCGAAGTTCCAGGGCAG
 I  H  W  V  R  Q  A  P  G  Q  R  L  E  W  I  G  R  I  D  P  A  N  G  N  T  K  Y  D  P  K  F  Q  G  R
                      40                                  50     52 A B C                  60

210        220        230        240        250        260        270        280        290        300
GGTCACTATAACATCAGACACGTCAATCACCACATACATGGAACTGAGCAGCCTGAGATCTGAGGACACTGCGGTCTATTACTGTTCTAGGTCTTATCAG
 V  T  I  T  S  D  T  S  I  T  T  Y  M  E  L  S  S  L  R  S  E  D  T  A  V  Y  Y  C  S  R  S  Y
                 70                            80    82 A B C                       90

310        320        330        340        350        360
TACATGGGTAGAAGATTTACTTACTGGGGCCAAGGGACTCTGGTCACTGTCTCTTCA (SEQ. ID. NO. 59)
 Y  M  G  R  R  F  T  Y  W  G  Q  G  T  L  V  T  V  S  S     (SEQ. ID. NO. 50)
      100 A  B  C                          110       113
```

CDR definitions and protein sequence numbering according to Kabat. CDR nucleotide and protein sequences are overlined Differences from murine reference sequence are underlined

FIG. 4:

(d) Heavy chain VH5

```
              10          20          30          40          50          60          70          80          90          100
CAGGTTCAGCTGGTTCAGTCTGGGGCAGAGGTGAAGAAGCCTGGGGCCTCAGTGAAGGTGTCCTGTAAGGTTTCTGGTTACACCTTCACAAGCTACAACATTAAACAGACCTATA
 Q  V  Q  L  V  Q  S  G  A  E  V  K  K  P  G  A  S  V  K  V  S  C  T  A  S  G  F  N  I  K  D  T  Y
                                  10                              20                              30

110         120         130         140         150         160         170         180         190         200
TACATTGGGTGAGGCAGGCCAGGGACAGGGGCTGGAGTGGATTGGATGGATTGATCCTGAAAGTGGTGATATTGAGTATTACTGAGAATCCGCAGTTCCAGGGGCAG
 I  H  W  V  R  Q  A  R  G  Q  R  L  E  W  I  G  R  I  D  P  V  N  G  D  T  E  Y  D  P  K  F  Q  G  R
                  40                              50                              60
                                                  52 A 210         220         230         240         250         260         270         280         290         300
GGTGACTATAACATCAGACGACGGCATCCTACACGGCTACATGGAGCTCAGCAGCCTGAGATCTGAGGACACTGCCGTGTATTACTGTGTTCTAGGTCTTAT
 V  T  I  T  S  D  A  S  T  S  T  A  Y  M  E  L  S  S  L  R  S  E  D  T  A  V  Y  Y  C  S  R  S  Y
                  70                              80                              90
                                  82 A B C 310         320         330         340         350         360
TACTACGGTTAGAACGACTTTACTTACTGGGGCCAAGGGACTCTGGTCACTGTCTCTTCA (SEQ. ID. NO. 60)
 Y  Y  G  R  R  F  T  Y  W  G  Q  G  T  L  V  T  V  S  S (SEQ. ID. NO. 51)
                  100                             110         113
                  100 A B C
```

CDR definitions and protein sequence numbering according to Kabat. CDR nucleotide and protein sequences are overlined Differences from murine reference sequence are underlined FIG. 5: Composite Human Antibody™ Sequence Variants of Anti-Beta Amyloid (MDT-2007) Light Chains (a) Light chain Vκ2

```
         10        20        30        40        50        60        70        80        90        100
GACATTGTGATGACACAGTCTCCATCTCCCTGACTGCCTCAGTTGGAGACAGAGTCACTATCACTTGCAAAGCAAGTCAAAGTCTGTTAAGCAGTGGAA
 D  I  V  M  T  Q  S  P  S  L  T  A  S  V  G  D  R  V  T  I  T  C  K  A  S  Q  S  L  L  S  S
                                                     10                        20        27 A B C D E F 110       120       130       140       150       160       170       180       190       200
ATGAAAGAACTACTTGACCTGGTACCAACAGAAACCAGGGCAGCCTCCTAAATTGTTGATCTACTTGGCATCTATTAGGGAATCTGGGGTCCCTGATCG
 N  K  N  Y  L  T  W  Y  Q  Q  K  P  G  Q  P  P  K  L  L  I  Y  W  A  S  I  R  E  S  G  V  P  D  R
                   30                        40                        50                        60

210       220       230       240       250       260       270       280       290       300
CTTCACAGGCAGTGGATCTGGAACAGATTTTCACTCTCACCATCAGTAGTCTGCAGGCTGAAGACGTTGCAGTGTATTACTGTCAGAATGATTATAATTAT
 F  T  G  S  G  S  G  T  D  F  T  L  T  I  S  S  L  Q  A  E  D  V  A  V  Y  Y  C  Q  N  D  Y  N  Y
                   70                        80                                        90

310       320       330
CCGTTCACATTCGGCCAGGGGACAAAGTTGGAGATAAAA (SEQ. ID. NO. 61)
 P  F  T  F  G  Q  G  T  K  L  E  I  K (SEQ. ID. NO. 53)
               100                 106 A
```

CDR definitions and protein sequence numbering according to Kabat. CDR nucleotide and protein sequences are overlined Differences from murine reference sequence are underlined

FIG. 5:

(b) Light chain Vκ3

```
         10         20         30         40         50         60         70         80         90        100
GACATTGTGATGACACAGTCTCCATCCTCCCTGACTGTGCCTCAGTCGGAGACAGGGTGACTATCACCTGCAAGGCCAGTCAGAGTGTTTTAAGCAGTGGAA
 D  I  V  M  T  Q  S  P  S  S  L  T  V  P  Q  S  E  T  G  D  Y  H  L  Q  G  Q  S  E  C  F  K  Q  W
                                                            T  I  T  C  K  A  S  Q  S  L  L  S  S
                                                               20                    27 A  B  C  D  E  F 110        120        130        140        150        160        170        180        190        200
ATCAGAAGAACTACTTGACTGGTACCAGCAGAAACCAGGACAGCCTCCTAAATTGTTGATCTACTGGGCATCTATTAGGGAATCTGGGGTCCCTGATCG
 N  Q  K  N  Y  L  T  W  Y  Q  Q  K  P  G  Q  P  P  K  L  L  I  Y  W  A  S  I  R  E  S  G  V  P  D  R
         30                      40                             50                           60

210        220        230        240        250        260        270        280        290        300
CTTCAGTGGCAGTGGATCTGGGACAGATTTCACTCTCACCATCAGTAGTTTGCAGGCTGAAGACGTTGCAGTGTATTACTGTCAGAATGATTATATGTAT
 F  S  G  S  G  S  G  T  D  F  T  L  T  I  S  S  L  Q  A  E  D  V  A  V  Y  Y  C  Q  N  D  Y  M  Y
      70                          80                                  90

310        320        330
CCATTCACATTCGGCCAAGGGACAAAGTTGGAGATAAAA (SEQ. ID. NO. 62)
 P  F  T  F  G  Q  G  T  K  L  E  I  K    (SEQ. ID. NO. 54)
      100                 106 A
```

CDR definitions and protein sequence numbering according to Kabat. CDR nucleotide and protein sequences are overlined Differences from murine reference sequence are underlined

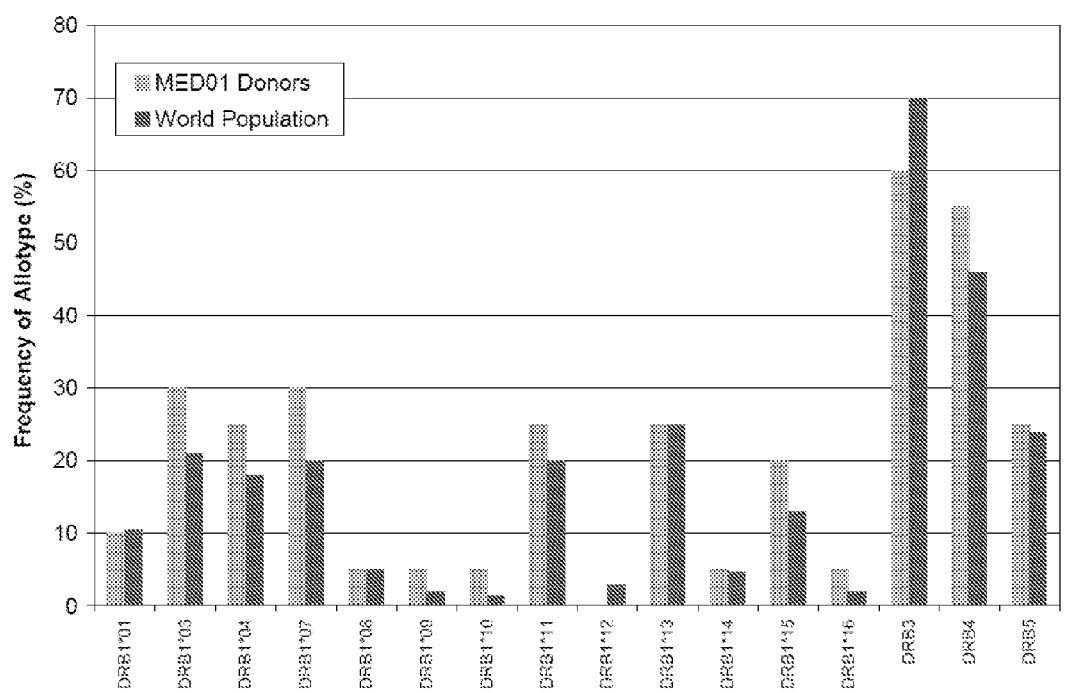
FIG. 6: Frequency of HLA class II allotypes in the world population and the study population (a)
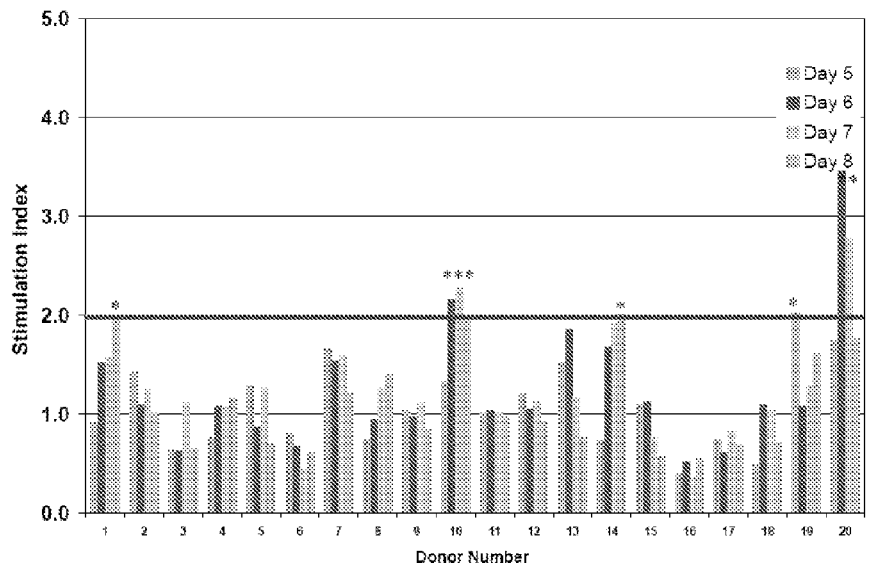
(b)
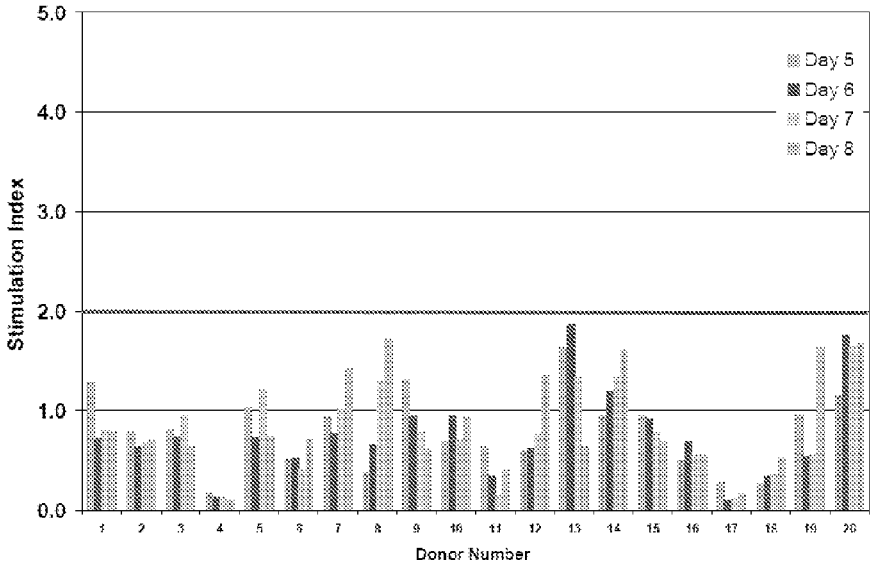
FIG. 7: MDT-2007 and chimeric antibodies were tested in EpiScreen™ time course T cell assays using PBMC from 20 donors.

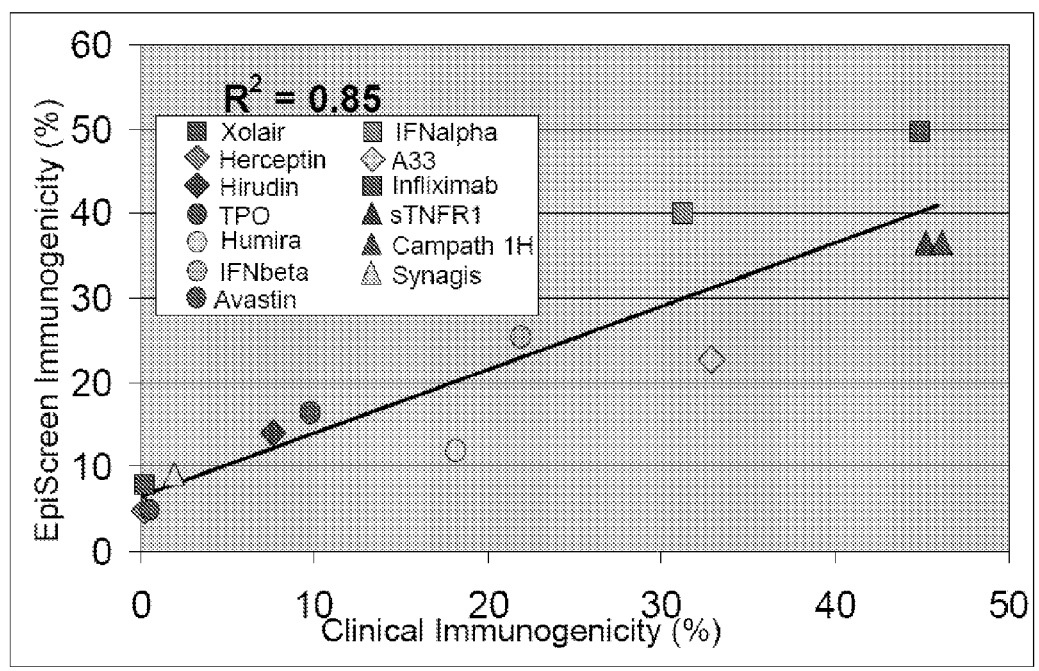
FIG. 8: Comparison of immunogencity predicted using EpiScreen Technology and immunogenicity observed in a clinical setting.

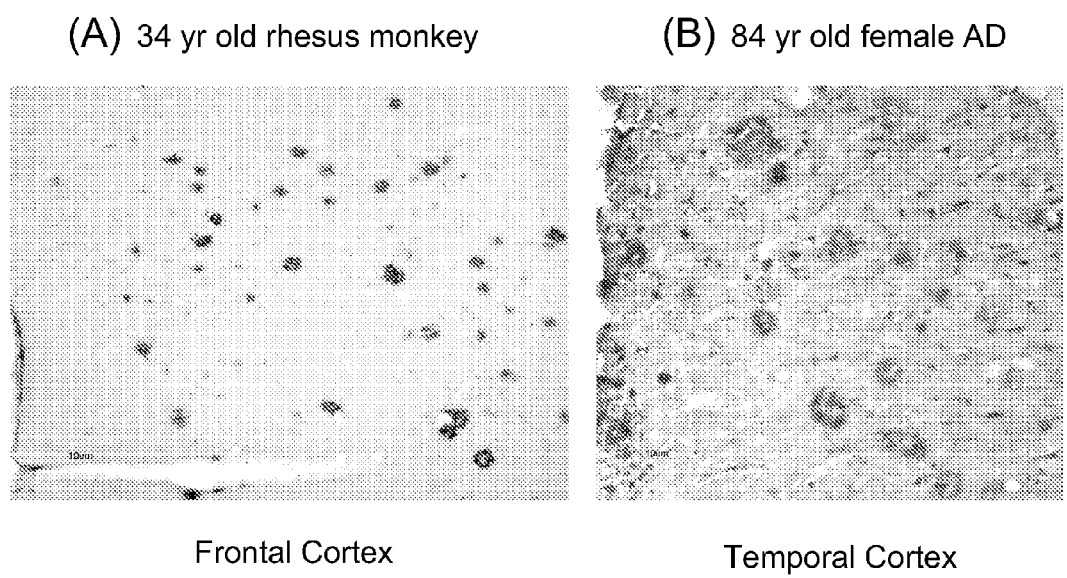
FIG. 9: MDT-2007 Amyloid Positive Plaques in the Aged Rhesus Monkey and AD Cortex

HUMANIZED ANTI-AMYLOID BETA ANTIBODIES

RELATED APPLICATIONS

This application is a divisional application of U.S. application Ser. No. 12/323,682 filed on Nov. 26, 2008 which claims the benefit of U.S. Provisional Application Ser. No. 60/990,401, filed on Nov. 27, 2007, and is a Continuation-In Part of U.S. application Ser. No. 12/120,269, filed May 14, 2008, which claims the benefit of Provisional Application Ser. Nos. 60/917,911, filed May 14, 2007, and 60/984,775, filed Nov. 2, 2007, which applications are hereby incorporated herein by reference in their respective entireties to the extent that they do not conflict with the present disclosure.

FIELD

This disclosure relates to antibodies to amyloid beta, more particularly to humanized antibodies to amyloid beta and compounds, compositions, and methods related thereto.

SEQUENCE LISTING

This application contains a Sequence Listing electronically submitted via EFS-Web to the United States Patent and Trademark Office as text filed named "SEQ_List_ST25.txt" having a size of 42 kb and created on Mar. 21, 2011. Due to the electronic filing of the Sequence Listing, the electronically submitted Sequence Listing serves as both the paper copy required by 37 CFR §1.821(c) and the CRF required by §1.821(e). The information contained in the Sequence Listing is hereby incorporated herein by reference.

BACKGROUND

Amyloid beta or "Aβ" is peptide of between about 39-43 amino acids that corresponds to a peptide formed in vivo upon cleavage of an amyloid beta A4 precursor protein (APP or ABPP) by beta-secretase (at the N-terminal portion of Aβ) and gamma secretase (at the C-terminal portion of Aβ). The most common isoforms of Aβ are Aβ40 and Aβ42, 40 and 42 amino acids, respectively. Aβ42 is less common, but is thought to be more fibrillogenic than Aβ40. Aβ is the main constituent of amyloid plaques in brains of Alzheimer's disease patients. Similar plaques can also be found in some Lewy body dementia patients. Such plaques or Aβ aggregates are also found in the cerebral vasculature of cerebral amyloid angiopathy patients.

Central and peripheral administration of antibodies directed to Aβ has been shown to be effective in reducing amyloid plaques and improving cognitive aspects of transgenic models of Alzheimer's Disease. However, the administration of antibodies or antibody fragments has had drawbacks that limit their applicability in humans due in part to immunogenicity of the antibodies or fragments. New techniques such as chimerization and humanization have been developed to reduce the immunogenicity of the antibodies or antibody fragments. Some newly developed antibodies appear to be completely free of epitopes recognized as foreign by the human immune system and may be generated by using transgenic mouse systems or phage/phagemid display.

Such completely humanized antibodies are a driving force behind the fast-paced expansion of antibody product pipelines. The generation of humanized antibodies, however, involves substituting human amino acid sequences for those of the animal in which the antibody was raised. Such alteration of the amino acid structure of an antibody may have unforeseen consequences in the ability of the antibody to bind the epitope to which it is directed.

BRIEF SUMMARY

Described herein are humanized anti-Aβ antibodies derived from a murine antibody directed to a N-terminal epitope of Aβ. The humanized antibodies have reduced or no human T cell epitopes and bind Aβ with an affinity similar to that of the murine antibody.

In various embodiments, an anti-amyloid beta antibody presented herein includes a variable heavy chain region having an amino acid sequence of SEQ ID NOs: 42, 44, 46, or 47-51, or an amino acid sequence having 90% or greater, 95% or greater, 98% or greater, or 99% or greater sequence identity to SEQ ID NOs: 42, 44, 46, or 47-51. In some embodiments where the antibody includes a heavy chain variable region having an amino acid sequence having 90% or greater, 95% or greater, 98% or greater, or 99% or greater sequence identity to SEQ ID NOs: 42, 44, 46, or 47-51, one or more or all of the amino acid differences are conservative substitutions.

In some embodiments, an anti-amyloid beta antibody presented herein includes a light chain variable region amino acid sequence of SEQ ID NOs: 43, 45, or 52-54, or an amino acid sequence having 90% or greater, 95% or greater, 98% or greater, or 99% or greater sequence identity to SEQ ID NOs: 43, 45, or 52-54. In some embodiments where the antibody includes a light chain variable region having an amino acid sequence having 90% or greater, 95% or greater, 98% or greater, or 99% or greater sequence identity to SEQ ID NOs: 43, 45, or 52-54, one or more or all of the amino acid differences are conservative substitutions.

Of course, any possible combination of such heavy chain and light chain amino acid sequences are contemplated herein. In some embodiments, a humanized antibody includes (i) a heavy chain variable region having an amino acid sequence of any of SEQ ID NOs: 47-51 and (ii) a light chain variable region having an amino acid sequence of any of SEQ ID NOs: 52-54.

In various embodiments, a method for treating a disease associated with increased or aberrant soluble Aβ, Aβ fibrils or Aβ plaques in a subject in need thereof includes administering an effective amount of a humanized antibody as described herein to the subject. The subject may be suffering from or at risk of, for example, Alzheimer's disease, Lewy body dementia, Down's syndrome, or cerebral amyloid angiopathy. The antibody may be administered directly to the subject's central nervous system, e.g., intrathecally, intraventricularly, or intraparenchymally. In some embodiments, the antibody is delivered to the subject via an infusion device implanted in the patient.

In some embodiments described herein, an isolated polynucleotide encodes an amino acid of any of SEQ ID NOs: 42-62, or an amino acid sequence having 90% or greater, 95% or greater, 98% or greater, or 99% or greater sequence identity to any of SEQ ID NOs: 42-62. In some embodiments where the antibody includes a heavy chain variable region having an amino acid sequence having 90% or greater, 95% or greater, 98% or greater, or 99% or greater sequence identity to SEQ ID NOs: 42-62, one or more or all of the amino acid differences are conservative substitutions. An expression vector may include the isolated polynucleotide. A cell may include the expression vector.

BRIEF DESCRIPTION OF THE DRAWINGS

FIG. 1 is a schematic diagram of light and heavy chain expression vectors.

FIG. 2 provides heavy chain and light chain amino acid sequences of a murine anti-Aβ antibody, a deimmunized variant of the murine antibody, humanized grafted variant of the murine antibody, and composite human antibodies derived from the murine antibody.

FIG. 3-5 provide nucleotide sequences corresponding to the amino acid sequences of the composite human antibodies shown in FIG. 2.

FIG. 6 is a graph showing the frequency of HLA class II allotypes in the world population and a population studied.

FIGS. 7a-b are graphs of results of MDT-2007 and chimeric antibodies tested in EPISCREEN™ (Antitope Ltd.) time course T cell assays using PBMC from 20 donors. Bulk cultures of PBMC incubated with test antibodies were sampled on days 5, 6, 7 and 8, and pulsed with 3H-Thymidine. Cells were harvested and incorporation of radioactivity measured by scintillation counting. Results for each triplicate sample were averaged and normalized by conversion to Stimulation Index (SI). The SI for each time point with each donor is shown above for (a) the chimeric antibody and (b) MDT-2007. The cut-off for determining positive responses with an SI≥2 is highlighted by the horizontal line at 2.0 and significant responses (p<0.05 in a student's t-test) are indicated (*).

FIG. 8 is a graph of a comparison of immunogenicity predicted using EPISCREEN™ (Antitope Ltd.) technology and immunogenicity observed in a clinical setting. Thirteen therapeutic proteins were tested for their relative risk of immunogenicity using EPISCREEN™ (Antitope Ltd.) technology. Results were plotted against the frequency of immunogenicity (antitherapeutic antibody responses) observed for each protein when used in the clinic (data sourced from PubMed). The line of regression and the correlation coefficient is shown.

FIGS. 9A-B are images of MDT-2007 amyloid positive plaques in a section of the frontal cortex of an aged Rhesus monkey (A) and a section of a temporal cortex of an 84 year-old human female diagnosed with Alzheimer's Disease (B).

Figure 10:
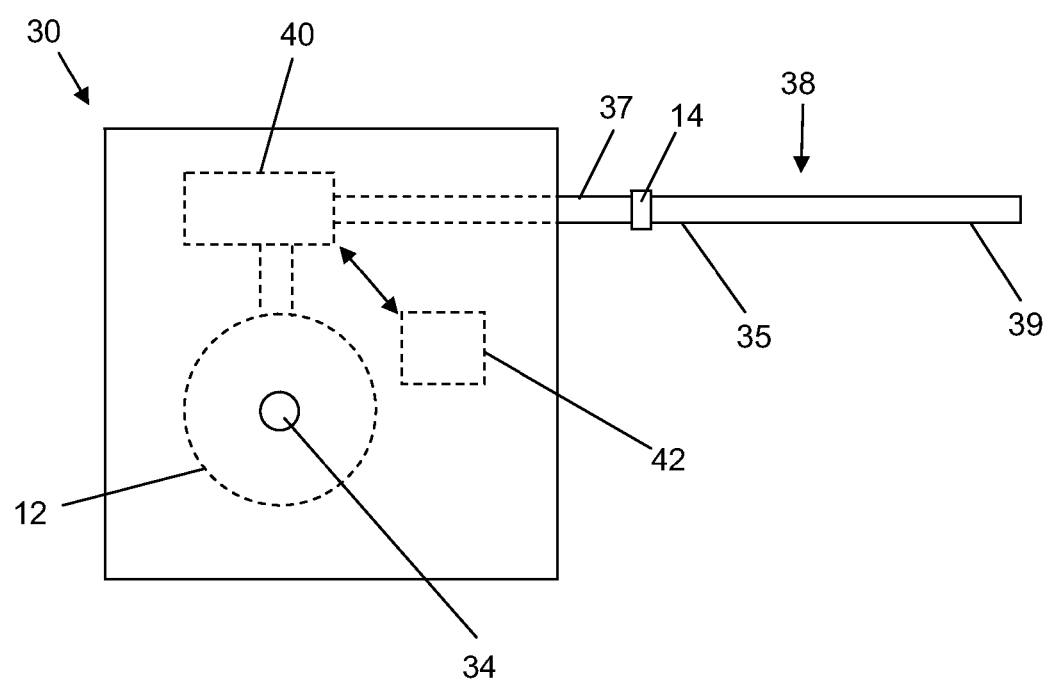
FIG. 10 is a schematic drawing of a side view of a representative infusion device showing selected internal components in block form.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of compositions of matter, apparatuses and methods. It is to be understood that other embodiments are contemplated and may be made without departing from the scope or spirit of the present disclosure. The following detailed description, therefore, is not to be taken in a limiting sense.

Definitions

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The term "antibody" is used in the broadest sense and specifically includes, for example, single anti-Aβ monoclonal antibodies (including agonist, antagonist, and neutralizing antibodies), anti-Aβ antibody compositions with poly-epitopic specificity, single chain anti-anti-Aβ antibodies, and fragments of anti-Aβ antibodies (see below). The term "monoclonal antibody" as used herein refers to an antibody obtained from a population of substantially homogeneous antibodies, i.e., the individual antibodies forming the population are identical except for possible naturally-occurring mutations that may be present in minor amounts. An antibody may include an immunoglobulin constant domain from any immunoglobulin, such as IgG-1, IgG-2, IgG-3, or IgG-4 subtypes, IgA (including IgA-1 and IgA-2), IgE, IgD or IgM.

As used herein, an "antibody fragment" means a portion of an intact antibody, most typically the antigen binding or variable region of the intact antibody. Examples of antibody fragments include Fab, Fab', F(ab')$_2$, and Fv fragments; diaries; linear antibodies (Zapata et al., Protein Eng. 8 (10): 1057-1062 [1995]); and single-chain antibody molecules.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments include the $V_H$ and $V_L$ domains of antibody, wherein these domains are present in a single polypeptide chain. Preferably, the Fv polypeptide further comprises a polypeptide linker between the $V_H$ and $V_L$ domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889-7893 (1993).

The term hybridoma describes the combination of a B cell that can recognize a particular antigen and a myeloma cell that lives indefinitely to make the hybridoma cell a kind of perpetual antibody-producing factory. The antibodies are therefore generated from animal cells, typically the mouse.

In most cases, the patient's immune system starts to recognize the mouse hybridoma cell as 'foreign' and will therefore destroy them. For this reason, the part of the mouse antibody gene responsible for recognizing a specific tumor antigen is combined with other parts from a human antibody gene. The product of this mouse-human antibody gene, called a "humanized" monoclonal antibody. This product looks enough like a normal human antibody to avoid being destroyed by the patient's own immune system. This helps the antibody to be effective for longer periods and avoids eliciting a potentially harmful immune response.

As used herein, the terms "treat", "therapy", and the like mean alleviating, slowing the progression, preventing, attenuating, or curing the treated disease.

As used herein, "disease", "disorder", "condition" and the like, as they relate to a subject's health, are used interchangeably and have meanings ascribed to each and all of such terms.

As used herein, "subject" means a mammal to which an agent, such as an antibody, is administered for the purposes of treatment or investigation. Mammals include mice, rats, cats, guinea pigs, hamsters, dogs, monkeys, chimpanzees, and humans.

As used herein, "isolated", in the context of an antibody or nucleic acid molecule encoding an antibody, means the antibody or nucleic acid has been removed from its natural milieu or has been altered from its natural state. As such "isolated" does not necessarily reflect the extent to which the antibody or nucleic acid molecule has been purified. However, it will be understood that an antibody or nucleic acid molecule that has been purified to some degree is "isolated". If the antibody or nucleic acid molecule does not exist in a natural milieu, i.e. it does not exist in nature, the molecule is "isolated" regardless of where it is present. By way of example, a humanized antibody that does not naturally exist in humans is "isolated" even when it is present in humans.

A "conservative amino acid substitution" refers to substituting an amino acid of a polypeptide for another amino acid that is functionally similar. Such conservative amino acids may be substituted for each other in a polypeptide with a minimal disturbance to the structure or function of the polypeptide according to well-known techniques. The following five groups each contain amino acids that may be conservatively substituted for one another: Aliphatic: Glycine (G), Alanine (A), Valine (V), Leucine (L), Isoleucine (I); Aromatic: Phenylalanine (F), Tyrosine (T), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q).

Antibodies, Vectors, and Cells

In various embodiments, a humanized antibody includes a heavy chain variable region having an amino acid sequence of SEQ ID NOs: 42, 44, 46, or 47-51 (see FIG. 2), or an amino acid sequence having 90% or greater, 95% or greater, 98% or greater, or 99% or greater sequence identity to SEQ ID NOs: 42, 44, 46, or 47-51. In some embodiments where the antibody includes a heavy chain variable region having an amino acid sequence having 90% or greater, 95% or greater, 98% or greater, or 99% or greater sequence identity to SEQ ID NOs: 42, 44, 46, or 47-51, one or more or all of the amino acid differences are conservative substitutions. The humanized antibody may further includes a light chain variable region amino acid sequence of SEQ ID NOs: 43, 45, or 52-54 (see FIG. 2), or an amino acid sequence having 90% or greater, 95% or greater, 98% or greater, or 99% or greater sequence identity to SEQ ID NOs: 43, 45, or 52-54. In some embodiments where the antibody includes a light chain variable region having an amino acid sequence having 90% or greater, 95% or greater, 98% or greater, or 99% or greater sequence identity to SEQ ID NOs: 43, 45, or 52-54, one or more or all of the amino acid differences are conservative substitutions. Any possible combination of such heavy chain and light chain amino acid sequences are contemplated. In some embodiments, a humanized antibody includes (i) a heavy chain variable region having an amino acid sequence of any of SEQ ID NOs: 47-51 and (ii) a light chain variable region having an amino acid sequence of any of SEQ ID NOs: 52-54.

In various embodiments, a humanized antibody includes (i) a variable heavy chain region comprising an amino acid sequence of SEQ ID NO:47 and (ii) a variable light chain region comprising an amino acid sequence of SEQ ID NO:52.

In various embodiments, a humanized antibody includes (i) a variable heavy chain region comprising an amino acid sequence of SEQ ID NO:48 and (ii) a variable light chain region comprising an amino acid sequence of SEQ ID NO:54.

In various embodiments, a humanized antibody includes (i) a variable heavy chain region comprising an amino acid sequence of SEQ ID NO:50 and (ii) a variable light chain region comprising an amino acid sequence of SEQ ID NO:52.

In various embodiments, a humanized antibody includes (i) a variable heavy chain region comprising an amino acid sequence of SEQ ID NO:51 and (ii) a variable light chain region comprising an amino acid sequence of SEQ ID NO:52.

In various embodiments, a humanized antibody includes (i) a variable heavy chain region comprising an amino acid sequence of SEQ ID NO:50 and (ii) a variable light chain region comprising an amino acid sequence of SEQ ID NO:53.

In various embodiments, a humanized antibody includes (i) a variable heavy chain region comprising an amino acid sequence of SEQ ID NO:51 and (ii) a variable light chain region comprising an amino acid sequence of SEQ ID NO:53.

In various embodiments, a polynucleotide includes a sequence that encodes a humanized antibody as described herein. In some embodiments, the polynucleotide comprises a sequence selected from the group consisting of SEQ ID NOs: 55, 56, 57, 58, 59, 60, 61, and 62.

In various embodiments, an expression vector includes a polynucleotide as described above.

In some embodiments, a cell contains such an expression vector. In numerous embodiments, the expression of the expression vector results in production of an antibody as described above.

Humanized antibodies, as described herein, may be prepared according to any known or developed method. Typically, the humanized antibodies will be expressed from expression vectors transfected or transformed into cells; e.g., as described the Examples provided below.

Cloning and Expression of Humanized Antibodies

Host cells may be transfected or transformed with cloning vectors or expression vectors for humanized antibody production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Anproach, M. Butler, ed. (IRL Press, 1991) and Molecular Cloning, A Laboratory Manual, $3^{rd}$ edition, vols 1-3, eds. Sambrook and Russel (2001) Cold Spring Harbor Laboratory Press.

Methods of eukaryotic cell transfection and prokaryotic cell transformation are known to those of ordinarily skill in the art and include, for example, $CaCl_2$, $CaPO_4$, liposome-mediated and electroporation. Depending on the host cell used, transformation is performed using standard techniques appropriate to such cells. For example, calcium treatment employing calcium chloride, as described Molecular Cloning, A Laboratory Manual, 3rd edition, vols 1-3, eds. Sambrook and Russel (2001) Cold Spring Harbor Laboratory Press, or electroporation may be used for prokaryotes. For mammalian cells that do not contain cell walls, the calcium phosphate precipitation method of Graham and van der Eb, Virology, 52:456-457 (1978) may be employed. General aspects of mammalian cell host system transfections have been described in, e.g., U.S. Pat. No. 4,399,216. Transformations into yeast are typically carried out according to the method of Van Solingen et al., J. Bact., 130:946 (1977) or Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185:527-537 (1990) and Mansour et al., Nature, 336:348-352 (1988).

Suitable host cells for cloning the DNA in the vectors herein include prokaryote, yeast, or higher eukaryote cells. Suitable prokaryotes include eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. Alternatively or in addition, in vitro methods of cloning, e.g., PCR or other nucleic acid polymerase reactions are suitable.

Suitable host cells for the expression of glycosylated humanized antibodies include those derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); Chinese hamster ovary cells/-DHFP (CHO, Urlaub and Chasin, Proc. Natl. Acad. Sci. USA, 77:4216 (1980)); mouse sertoli cells (TM4, Mather, Biol. Reprod., 23:243-251 (1980)); human lung cells (W138, ATCC CCL 75); human liver cells (Hep G2, HB 8065); and mouse mammary tumor (MMT 060562, ATCC CCL51). The selection of the appropriate host cell is within the routine ability skill in the art.

The nucleic acid (e.g., cDNA or genomic DNA) encoding a humanized antibody (or portion thereof) may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to those of skill in the art.

The humanized antibody (or portion thereof) may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the humanized antibody (or portion thereof)-encoding DNA that is inserted into the vector.

Expression vectors or cloning vectors may include a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Expression and cloning vectors usually contain a promoter operably linked to the humanized antibody (or portion thereof)-encoding nucleic acid sequence to direct mRNA synthesis. Promoters recognized by a variety of potential host cells are well known. Promoters suitable for use with prokaryotic hosts include the β-lactamase and lactose promoter systems [Chang et al., Nature, 275:615 (1978); Goeddel et al., Nature, 281:544 (1979)], alkaline phosphatase, a tryptophan (trp) promoter system [Goeddel, Nucleic Acids Res., 8:4057 (1980); EP 36,776], and hybrid promoters such as the tac promoter [deBoer et al., Proc. Natl. Acad. Sci. USA, 80:21-25 (1983)]. Promoters for use in bacterial systems also will contain a Shine-Dalgarno (S.D.) sequence operably linked to the DNA encoding HCN or Kir2.1 channel.

Humanized antibody (or portion thereof) transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the humanized antibody by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the humanized antibody (or portion thereof) coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding a humanized antibody (or portion thereof).

For example, a viral vector, such as an adeno-associated viral (AAV) vector may be operatively linked components of control elements. For example, a typical vector includes a transcriptional initiation region, a nucleotide sequence of the protein to be expressed, and a transcriptional termination region. Typically, such an operatively linked construct will be flanked at its 5 and 3 regions with AAV ITR sequences, which are viral cis elements. The control sequences can often be provided from promoters derived from viruses such as, polyoma, Adenovirus 2, cytomegalovirus, and Simian Virus 40. Viral regulatory sequences can be chosen to achieve a high level of expression in a variety of cells. Alternatively, ubiquitously expressing promoters, such as the early cytomegalovirus promoter can be utilized to accomplish expression in any cell type. A third alternative is the use of promoters that drive tissue specific expression. This approach is particularly useful where expression of the desired protein in non-target tissue may have deleterious effects. Thus, according to various embodiments, the vector contains the proximal human brain natriuretic brain (hBNP) promoter that functions as a cardiac-specific promoter. For details on construction of such a vector see LaPointe et al., "Left Ventricular Targeting of Reporter Gene Expression In Vivo by Human BNP Promoter in an Adenoviral Vector," Am. J. Physiol. Heart Circ. Physiol., 283:H1439-45 (2002).

Expression vectors containing DNA encoding a humanized antibody (or portion thereof) may be administered in vivo in any known or future developed manner. In various embodiments, the expression vectors are packaged into viruses, such as adenoviruses, and are delivered in proximity to targeted cells, tissue or organs. In various embodiments, the expression vectors are packaged into adenoviruses, such as helper-dependent adeno virus (HDAd) or adeno-associated virus pseudo-type 9 (AAV2/9). HDAd virus packaging typically illicits less of an immunogenic response in vivo compared to some other adenoviruses and thus allows for longer term expression. AAV2/9 packaging can result in cardiac tropism as well as a prolonged expression time frame.

Alternatively, non-viral delivery systems are employed. For example, liposomes, DNA complexes, plasmid, liposome complexes, naked DNA, DNA-coated particles, or polymer based systems may be used to deliver the desired sequence to the cells. The above-mentioned delivery systems and protocols therefore can be found in Gene Targeting Protocols, Kmeic 2ed., pages 1-35 (2002) and Gene Transfer and Expression Protocols, Vol. 7, Murray ed., Pages 81-89 (1991).

An expression vector including a polynucleotide encoding a humanized antibody (or portion thereof) can be delivered into a cell by, for example, transfection or transduction procedures. Transfection and transduction refer to the acquisition by a cell of new genetic material by incorporation of added nucleic acid molecules. Transfection can occur by physical or chemical methods. Many transfection techniques are known to those of ordinary skill in the art including, without limitation, calcium phosphate DNA co-precipitation, DEAE-dextrin DNA transfection, electroporation, naked plasmid adsorption, and cationic liposome-mediated transfection. Transduction refers to the process of transferring nucleic acid into a cell using a DNA or RNA virus. Suitable viral vectors for use as transducing agents include, but are not limited to, retroviral vectors, adeno associated viral vectors, vaccinia viruses, an Semliki Foret virus vectors.

Separate vectors may be employed to express a light chain and a heavy chain. Of course, nucleic acid encoding a heavy chain and a light chain may be introduced into a single vector.

Antibody Compositions

Humanized anti-Aβ antibodies can be administered for the treatment of various disorders in the form of pharmaceutical compositions. Pharmaceutical compositions may be used for the purposes of treatment or for investigation.

Antibodies as described herein can be administered as pharmaceutical compositions the antibody and a variety of other pharmaceutically acceptable components. See Remington's Pharmaceutical Science (15th ed., Mack Publishing Company, Easton, Pa. (1980)). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to adversely affect the biological activity of the antibody. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized SEPHAROSE™ (GE Healthcare Bio-Sciences Ltd.), agarose, cellulose, and the like), polymeric amino acids, amino acid copolymers, and lipid aggregates (such as oil droplets or liposomes).

Pharmaceutical compositions may be injectable compositions. Injectable compositions include solutions, suspensions, dispersions, and the like. Injectable solutions, suspensions, dispersions, and the like may be formulated according to techniques well-known in the art (see, for example, Remington's Pharmaceutical Sciences, Chapter 43, 14th Ed., Mack Publishing Co., Easton, Pa.), using suitable dispersing or wetting and suspending agents, such as sterile oils, including synthetic mono- or diglycerides, and fatty acids, including oleic acid.

Injectable compositions that include an anti-Aβ antibody may be prepared in water, saline, isotonic saline, phosphate-buffered saline, citrate-buffered saline, and the like and may optionally mixed with a nontoxic surfactant. Dispersions may also be prepared in glycerol, liquid polyethylene, glycols, DNA, vegetable oils, triacetin, and the like and mixtures thereof. Under ordinary conditions of storage and use, these preparations may contain a preservative to prevent the growth of microorganisms. Pharmaceutical dosage forms suitable for injection or infusion include sterile, aqueous solutions or dispersions or sterile powders comprising an active ingredient which powders are adapted for the extemporaneous preparation of sterile injectable or infusible solutions or dispersions. Preferably, the ultimate dosage form is a sterile fluid and stable under the conditions of manufacture and storage. A liquid carrier or vehicle of the solution, suspension or dispersion may be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. Proper fluidity of solutions, suspensions or dispersions may be maintained, for example, by the formation of liposomes, by the maintenance of the desired particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. Isotonic agents such as sugars, buffers, or sodium chloride may be included. Prolonged absorption of the injectable compositions can be brought about by the inclusion in the composition of agents delaying absorption—for example, aluminum monosterate hydrogels and gelatin. Solubility enhancers may be added.

Sterile injectable compositions may be prepared by incorporating an anti-Aβ antibody in the desired amount in the appropriate solvent with various other ingredients, e.g. as enumerated above, and followed by sterilization, as desired, by, for example filter sterilization. In the case of sterile powders for the preparation of sterile injectable solutions, methods of preparation include vacuum drying and freeze-drying techniques, which yield a powder of the active ingredient plus any additional desired ingredient present in a previously sterile-filtered solution. Any suitable sterilization process may be employed, such as filter sterilization, e.g. 0.22 micron filter or nanofiltration, gamma or electron beam sterilization, or pused white light. Other suitable sterilization processes include UtiSter (Pegasus Biologics, Irvine Calif.) and those described in, e.g., U.S. Pat. No. 6,946,098 and U.S. Pat. No. 5,730,933.

In various embodiments, the final solution is adjusted to have a pH between about 4 and about 9, between about 5 and about 7, between about 5.5 and about 6.5, or about 6. The pH of the composition may be adjusted with a pharmacologically acceptable acid, base or buffer. Hydrochloric acid is an example of a suitable acid, and sodium hydroxide is an example of a suitable base. The hydrochloric acid or sodium hydroxide may be in any suitable form, such as a 1N solution A resultant injectable solution preferably contains an amount of one or more anti-Aβ antibodies effective to treat a disease associated with increase or aberrant soluble Aβ or to allow meaningful study of a subject to which the solution is injected. In various embodiments for direct CNS infusion, an anti-Aβ antibody is present in an injectable composition at a concentration between about 0.0001 mg/ml and about 50 mg/ml. In various embodiments, an anti-Aβ antibody is present in an injectable composition at a concentration between about 0.01 mg/mL and about 10 mg/mL. In various embodiments, an anti-Aβ antibody is present in an injectable composition at a concentration of about 1 mg/mL.

Of course, anti-Aβ antibodies may be administered to the CNS in the form of a depot injection or implant preparation, which can be formulated in such a manner as to permit a sustained or pulsatile release of the active ingredient.

The formulations discussed above or other formulations containing an anti-Aβ antibody may be administered to a subject via any acceptable route. In various embodiments, a formulation comprising an antibody agent capable of binding Aβ is chronically administered directly to the CNS of a subject. By chronically, it is meant over the course or days, weeks or months. In some circumstances, chronic administration may occur at various times or continuously over the life of the patient after therapy is initiated, or until the patient no longer presents symptoms of the treated disease state. As used herein, "direct administration to the CNS", or the like, means delivery of an agent via a delivery region infusion portion of a catheter, where the delivery portion of the catheter is located within the CNS. Example routes of direct CNS administration include intraparenchymal, intrathecal, intracerebroventricular, epidural, or the like. Non-limiting examples of catheters include cannulas, needles, tubes, and the like. A delivery portion of a catheter is typically located at or near a distal end portion of a catheter and may include an opening in fluid communication with a lumen of a catheter.

In some embodiments, formulations containing an anti-Aβ antibody are administered to the CNS via an implantable infusion device, for example, as described below with regard to FIGS. 10-16 and associated text under the heading "delivery device". Suitable systems and conditions for delivering anti-Aβ antibodies via an implantable infusion device are described in, e.g., U.S. patent application Ser. No. 12/120,269, filed May 14, 2008, which application is hereby incorporated herein by reference in its entirety to the extent that it does not conflict with the present disclosure.

An injectable composition including an anti-Aβ antibody may be delivered at any suitable rate. For chronic delivery to the CNS, the composition may be delivered at a rate of 0.01-15 ml/day, 0.01-5 ml/day, or 0.01-1 ml/day. It will be understood that the concentration of the anti-Aβ antibody in the composition may be adjusted, based on the delivery rate, to achieve a desired daily dose. The rate of delivery may be constant or may be variable. In various embodiments, delivery includes periods of increased delivery rate (e.g., pulsed boluses) on top of a constant lower rate. Such pulsed boluses may readily be achieved with a programmable infusion device such as the SYNCHROMED II® (Medtronic, Inc.) infusion device. Such pulsed bolus administration may result in improved distribution of the delivered antibody relative to constant rate delivery due to increased convection. In some embodiments, the antibody may be delivered for a period of time, the delivery may then be halted, and then resumed. For example, the antibody may be delivered for one hour to one week, delivery may then be halted for one hour to one week, and so on. Such a dosing scheme may serve to prolong the delivery life of the antibody, as the half life of the delivered antibody may be considerably shorter than the half life of an antibody housed in a reservoir of an infusion device.

In some embodiments, the mode of delivery may be altered during the course of treatment. For example, the antibody may be delivered i.c.v. at one stage of treatment and delivered intraparenchymally (i.p.a) at another stage of treatment, as conditions warrant. For example, if it is desired to obtain microglial activation to clear of Aβ, i.p.a. administration may be desired. If clearance via a CSF sink is desired, i.c.v. administration may be desired. Alternatively, or in addition, an antibody may be delivered i.c.v. and i.p.a at the same time. Regardless of whether the route of administration is altered or if delivery is accomplished simultaneously via two routes, it may be desirable to implant a delivery region of a catheter intraparenchymally and implant a delivery region of the same (e.g., split catheter) or different catheter in the CSF at the time of initial implant.

In some embodiments, an antibody may be conjugated with poly-sialic acid, dextran, polyethylene glycol, or the like. Polysialylation may result in reduced proteolysis, retention of binding and biological activity, prolongation of half-life in the circulation, or reduction in immunogenicity of the antibody. Studies have been performed that show that mouse 6E10 anti-amyloid beta IgG and F(ab')$_2$ antibodies are capable of being sialylated, that sialylation does not adversely affect the ability of the antibody to bind amyloid beta, and that bioavailability (plasma half-life) is markedly enhanced by between about three- and forty-fold (data not shown). If humanized antibodies described herein are to be conjugated with polysialic acid, significantly less antibody may need to be delivered to achieve a desired effect, which could result in reduced toxicity. Such effects may be most desirable for systemic administration, where dosages tend to be greater than with direct central administration. However, conjugation with polysialic acid or other polymers may be desirable and beneficial with intracerebroventricular or intraparenchymal administration, whether delivered via an implantable infusion system or via bolus infusion.

Methods

Administering an antibody capable of binding Aβ in the CNS of a subject as described herein or according to any other known or developed technique may be used to treat or prevent a disease associated with increased or aberrant soluble Aβ, amyloid fibrils or amyloid plaques. Examples of disease associated with increased or aberrant soluble Aβ, amyloid fibrils or amyloid plaques include Alzheimer's disease (AD), cerebral amyloid angiopathy (CAA), Lewy body dementia, and Down's Syndrome (DS).

Any amount of antibody effective to bind Aβ, whether soluble, in fibrils, plaques, or the like may be employed. In general, a daily dose of between about 0.0001 and about 1 mg of the antibody per kg of the subject's body weight will be effective. In various embodiments, daily doses of between about 0.001 and about 1, between about 0.01 and about 0.1, or between about 0.1 and about 1 mg of the antibody per kg of the subject's body weight are administered to the subject's CNS. The above daily doses should be generally effective for i.c.v. delivery to a lateral ventrical of the subject. For intrathecal delivery, increased dosages may be warranted. For example, daily dosages may be increased by about 20% relative to i.c.v. Any other suitable modification in dosing based on route of administration in comparison to i.c.v. may be employed. Of course, the antibody need not be administered daily, but may be administered only once, once a week, once a month, every other day, or according to any other suitable regimen.

In various embodiments a method includes identifying a subject suffering from or at risk of AD and chronically delivering to the CNS of the subject an antibody directed to Aft Those at risk of AD include those of advancing age, family history of the disease, mutations in APP or related genes, having heart disease risk factors, having stress or high levels of anxiety. Identification of those suffering from or at risk of AD can be readily accomplished by a physician. Diagnosis may be based on mental, psychiatric and neuropyschological assessments, blood tests, brain imaging (PET, MRI, CT scan), urine tests, tests on the cerebrospinal fluid obtained through lumbar puncture, or the like.

In various embodiments a method includes identifying a patient suffering from or at risk of CAA and chronically delivering to the CNS of the patient a humanized antibody directed to Aβ Symptoms of CAA include weakness or paralysis of the limbs, difficulty speaking, loss of sensation or balance, or even coma. If blood leaks out to the sensitive tissue around the brain, it can cause a sudden and severe headache. Other symptoms sometimes caused by irritation of the surrounding brain are seizures (convulsions) or short spells of temporary neurologic symptoms such as tingling or weakness in the limbs or face. CAA patients can be identified by, e.g., examination of an evacuated hematoma or brain biopsy specimen, the frequency of APOE $\epsilon$2 or $\epsilon$4 alleles, with clinical or radiographic (MRI and CT scans) grounds according the Boston Criteria (Knudsen et al., 2001, Neurology; 56:537-539), or the like. Those at risk of CAA include those of advancing age, those having the APOE genotype, and those having other risk factors associated with AD.

In various embodiments a method includes identifying a patient suffering from or at risk of Down Syndrome and chronically delivering to the CNS of the patient a humanized antibody directed to Aβ. A newborn with Down syndrome can be identified at birth by a physician's physical exam. The diagnosis may be confirmed through kariotyping. Multiple screening tests may be used to test or diagnosis a patient prior to birth (biomarkers, nuchal translucency, amniocentesis, etc.). A Down's syndrome patient may be diagnosis with AD using diagnostic criteria relevant for AD.

In various embodiments a method includes identifying a patient suffering from or at risk of Lewy body dementia and chronically delivering to the CNS of the patient a humanized antibody directed to Aβ. Those suffering from or at risk of Lewy body dementia can be identified by mental, psychiatric or neuropyschological assessments, blood tests, brain imaging (PET, MRI, CT scan), urine tests, tests on the cerebrospinal fluid obtained through lumbar puncture, or the like. Those at risk of Lewy body dementia include those of advancing age.

In various embodiments, cerebral plaques may be cleared or prevented from forming by administering anti-Aβ antibodies to a subject's CNS. It will be understood that achieving any level of clearing of a plaque or plaques will constitute clearing of the plaque or plaques. It will be further understood that achieving any level of prevention of formation of a plaque or plaques will constitute preventing formation of the plaque or plaques. Accordingly, in various embodiments, methods for clearing plaques include delivering, to a subject in need thereof, an amount of a humanized anti-Aβ antibody effective in clearing the plaques. In various embodiments, methods for preventing the formation of plaques include delivering, to a subject in need thereof, an amount of a humanized anti-Aβ antibody effective in preventing the formation the plaques. The methods may further include clearing or preventing parenchymal amyloid plaques or soluble forms of Aβ. The methods may further include improving cognitive aspects of the subject.

In various embodiments, cognitive abilities of a subject are improved by administering anti-Aβ antibodies to a subject's CNS.

In various embodiments, parenchymal amyloid plaques or soluble forms of Aβ are cleared in a subject by administering anti-Aβ antibodies to a subject's CNS.

The ability of a therapy described herein to treat a disease may be evaluated through medical examination, e.g. as discussed above, or by diagnostic or other tests. In various embodiments, a method as described in WO 2006/107814 (Bateman et al.) is performed. For example, a subject may be administered radiolabeled leucine. Samples, such as plasma or CSF, may then be obtained to quantify the labeled-to-unlabeled leucine in, for example, amyloid beta or other key disease related biomarkers, to determine the production and clearance rate of such proteins or polypeptides.

Clearing of, or formation of, amyloid beta can be evaluated in vivo by structural or functional neuro-imaging techniques. For example, diffusion tensor MRI (reviewed in Parente et al., 2008; Chua et al., 2008), PET imaging with the Aβ binding compound, Pittsburgh Compound B (PiB, Klunk et al., 2004; Fagan et al., 2006; Fagan et al 2007) or other SPECT based imaging of fibrillar Aβ structures and measurement of CSF levels of Aβ42 or tau may be employed. Distribution of vascular Aβ may be evaluated using differential interpretation of PET imaging of PiB (Johnson et al., 2007). Additionally, a cerebral microhemorrahage may be recognized by on gradient-echo or T-2 weighted MRI sequences (Viswanathan and Chabriat, 2006).

Similarly, detection of hemorrhages of the cerebral vasculature can be evaluated by imaging techniques, clinical evaluation, or the like. Spontaneous intracerebral hemorrhage (ICH) usually results in a focal neurologic deficit and is easily diagnosed on clinical and radiographic grounds (computed tomography (CT) scan, T-2 weighted MRI). Cerebral microhemorrhage results from underlying small vessel pathologies such as hypertensive vasculpathy or CAA. Cerebral microhemorrhages, best visualized by MRI, result from rupture of small blood vessels. The MRI diagnosis can be variable as described by Orgagozo et al., 2003 (Subacute meningoencephalitis in a subset of patients with AD after Aβ42 immunization-Elan Trial). For instance, patients showing signs and symptoms of aseptic meningoencephalitis MRIs showed only meningeal enhancement, whereas others had meningeal thickening, white matter lesions, with or without enhancing or edema, and a majority had posterior cerebral cortical or cerebellar lesions. Other potential diagnostics include changes in intracranial pressure, which may be detected by specific MRI techniques (Glick, et al., 2006, Alperin) or other standard techniques as described in Method of detecting brain microhemmorhage (U.S. Pat. No. 5,951,476).

In various embodiments, a humanized antibody is used to detect Aβ; e.g., in a diagnostic assay or as part of a diagnostic kit. For example, the humanized antibody may be used to determine the ability of a therapeutic agent or putative therapeutic agent to affect processing of APP to produce soluble Aβ. In such uses, it may be desirable for the antibody to be labeled; e.g., with a fluorescent tag, a paramagnetic tag, or the like.

Delivery Device

In various embodiments, formulations containing an anti-Aβ antibody are administered to the CNS via an infusion device. A system including an infusion device may be used to deliver a composition containing an anti-Aβ antibody to the CNS of a subject. The system may further includes a catheter operably couplable to the infusion device. The infusion device may include a drive mechanism. Non-limiting examples of drive mechanisms include peristaltic pumps, osmotic pumps, piston pumps, pressurized gas mechanisms, and the like. Devices including such drive mechanisms may be fixed-rate pumps, variable rate pumps, selectable rate pumps, programmable pumps and the like. Each of the aforementioned infusion systems contain a reservoir for housing a fluid composition containing the anti-Aβ antibody. The catheter includes one or more delivery regions, through which the fluid may be delivered to one or more target regions of the subject. The infusion device may be implantable or may be placed external to the subject.

An infusion device 30 according to various embodiments is shown in FIG. 10 and includes a reservoir 12 for housing a composition and a drive mechanism 40 operably coupled to the reservoir 12. The catheter 38 shown in FIG. 11 has a proximal end 35 coupled to the therapy delivery device 30 and a distal end 39 configured to be implanted in a target location of a subject. Between the proximal end 35 and distal end 39 or at the distal end 39, the catheter 38 has one or more delivery regions (not shown), such as openings, through which the composition may be delivered. The infusion device 30 may have a port 34 into which a hypodermic needle can be inserted to inject a composition into reservoir 12. The infusion device 30 may have a catheter port 37, to which the proximal end 35 of catheter 38 may be coupled. The catheter port 37 may be operably coupled to reservoir 12. A connector 14, such as a barbed connector or sutureless connector, may be used to couple the catheter 38 to the catheter port 37 of the infusion device 30. The infusion device 30 may be operated to discharge a predetermined dosage of the pumped fluid into a target region of a subject. The infusion device 30 may contain a microprocessor 42 or similar device that can be programmed to control the amount of fluid delivery. The programming may be accomplished with an external programmer/control unit via telemetry. A controlled amount of fluid may be delivered over a specified time period. With the use of a programmable infusion device 30, dosage regimens may be programmed and tailored for a particular patient. Additionally, different therapeutic dosages can be programmed for different combinations of fluid comprising therapeutics. Those skilled in the art will recognize that a programmable infusion device 30 allows for starting conservatively with lower doses and adjusting to a more aggressive dosing scheme, if warranted, based on safety and efficacy factors.

While not shown in FIG. 10, device 30 may include a catheter access port to allow for direct delivery of a composition including an anti-Aβ antibody via catheter 38. Also not shown are other components, such as one-way valves, that may be included at one or more locations along the fluid flow path of the device 30. It will be understood that the components and the configuration of the components depicted in FIG. 10 may be readily modified to achieve a suitable infusion device 30 for delivering an injectable composition including a humanized anti-Aβ antibody.

Figure 11:
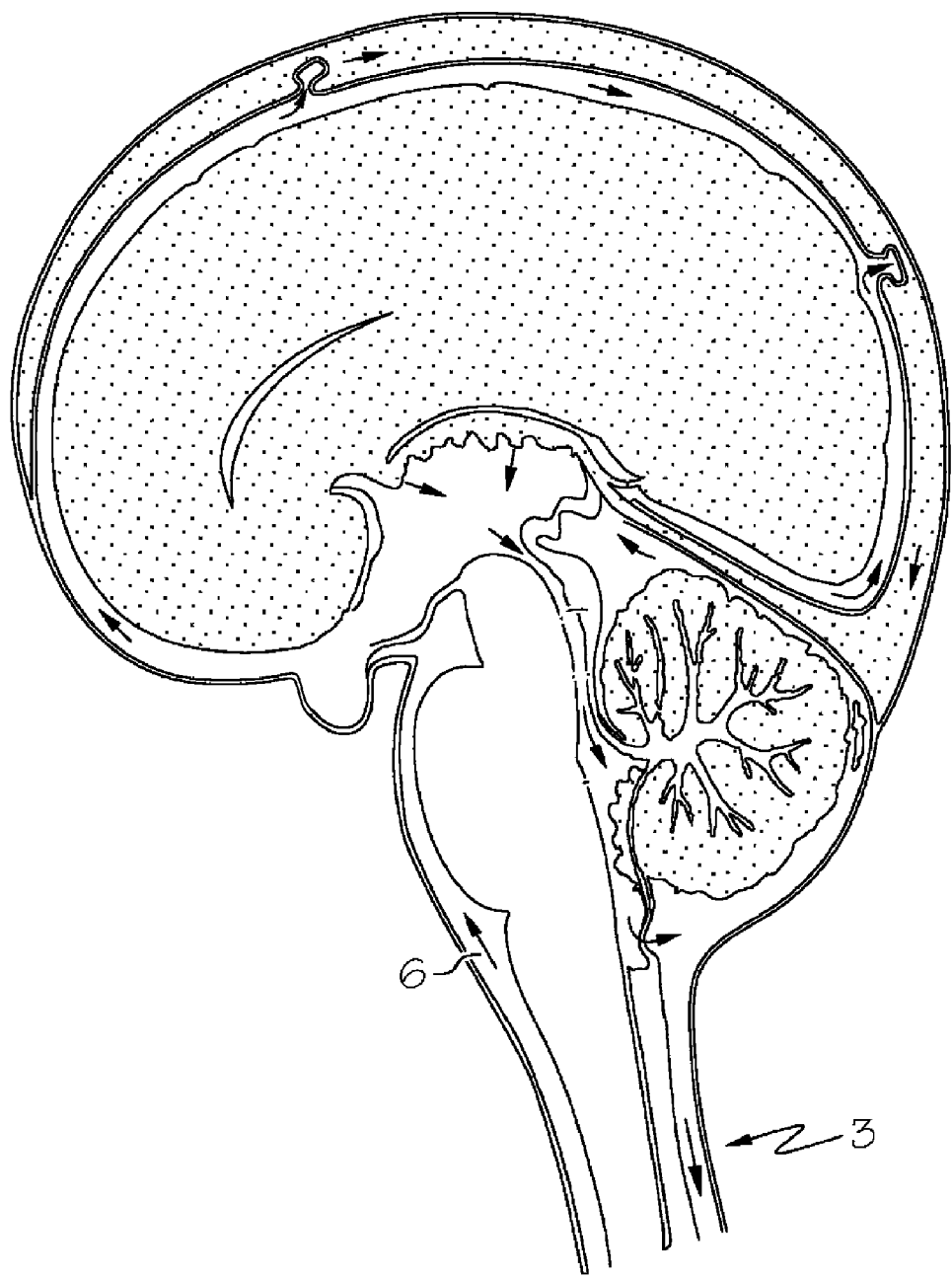
FIG. 11 is a schematic drawing of a section of a brain and portions of a spinal cord showing cerebrospinal fluid flow.

According to various embodiments, a composition comprising a humanized anti-Aβ antibody may be delivered directly to cerebrospinal fluid of a subject. Referring to FIG. 11, cerebrospinal fluid (CSF) 6 exits the foramen of Magendie and Luschka to flow around the brainstem and cerebellum. The arrows within the subarachnoid space 3 in FIG. 11 indicate cerebrospinal fluid 6 flow. The subarachnoid space 3 is a compartment within the central nervous system that contains cerebrospinal fluid 6. The cerebrospinal fluid 6 is produced in the ventricular system of the brain and communicates freely with the subarachnoid space 3 via the foramen of Magendie and Luschka. A composition containing an anti-Aβ antibody may be delivered to cerebrospinal fluid 6 of a subject anywhere that the cerebrospinal fluid 6 is accessible. For example, the composition may be administered intrathecally or intracerebroventricularly.

Figure 12:
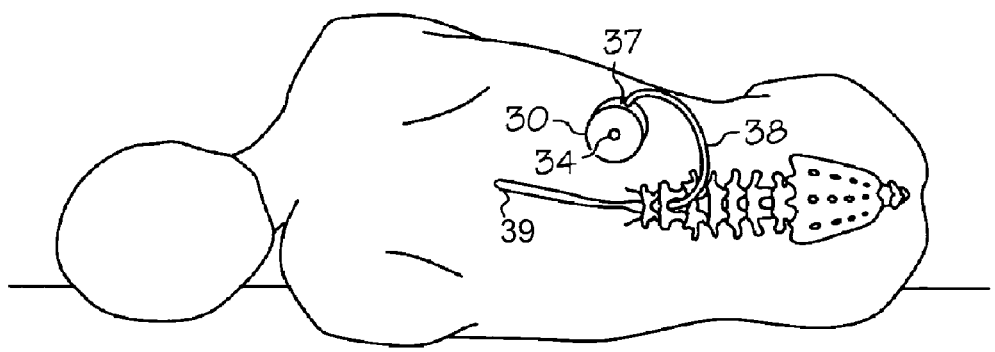
FIG. 12 is a schematic drawing of a view of an infusion device and associated catheter implanted in a patient.

FIG. 12 illustrates a representative implantable system configured for intrathecal delivery of a composition containing an anti-Aβ antibody. As shown in FIG. 12, a system or device 30 may be implanted below the skin of a patient. Preferably the device 30 is implanted in a location where the implantation interferes as little as practicable with activity of the subject in which it is implanted. One suitable location for implanting the device 30 is subcutaneously in the lower abdomen. In various embodiments, catheter 38 is positioned so that the distal end 39 of catheter 38 is located in the subarachnoid space 3 of the spinal cord such that a delivery region (not shown) of catheter is also located within the subarachnoid space 3. It will be understood that the delivery region can be placed in a multitude of locations to direct delivery of an agent to a multitude of locations within the cerebrospinal fluid 6 of the patient. The location of the distal end 39 and delivery region(s) of the catheter 38 may be adjusted to improve therapeutic efficacy.

According to various embodiments, a composition containing a humanized anti-Aβ antibody may be delivered intraparenchymally directly to brain tissue of a subject. An infusion device may be used to deliver the agent to the brain tissue. A catheter may be operably coupled to the infusion device and a delivery region of the catheter may be placed in or near a target region of the brain.

Figure 13:
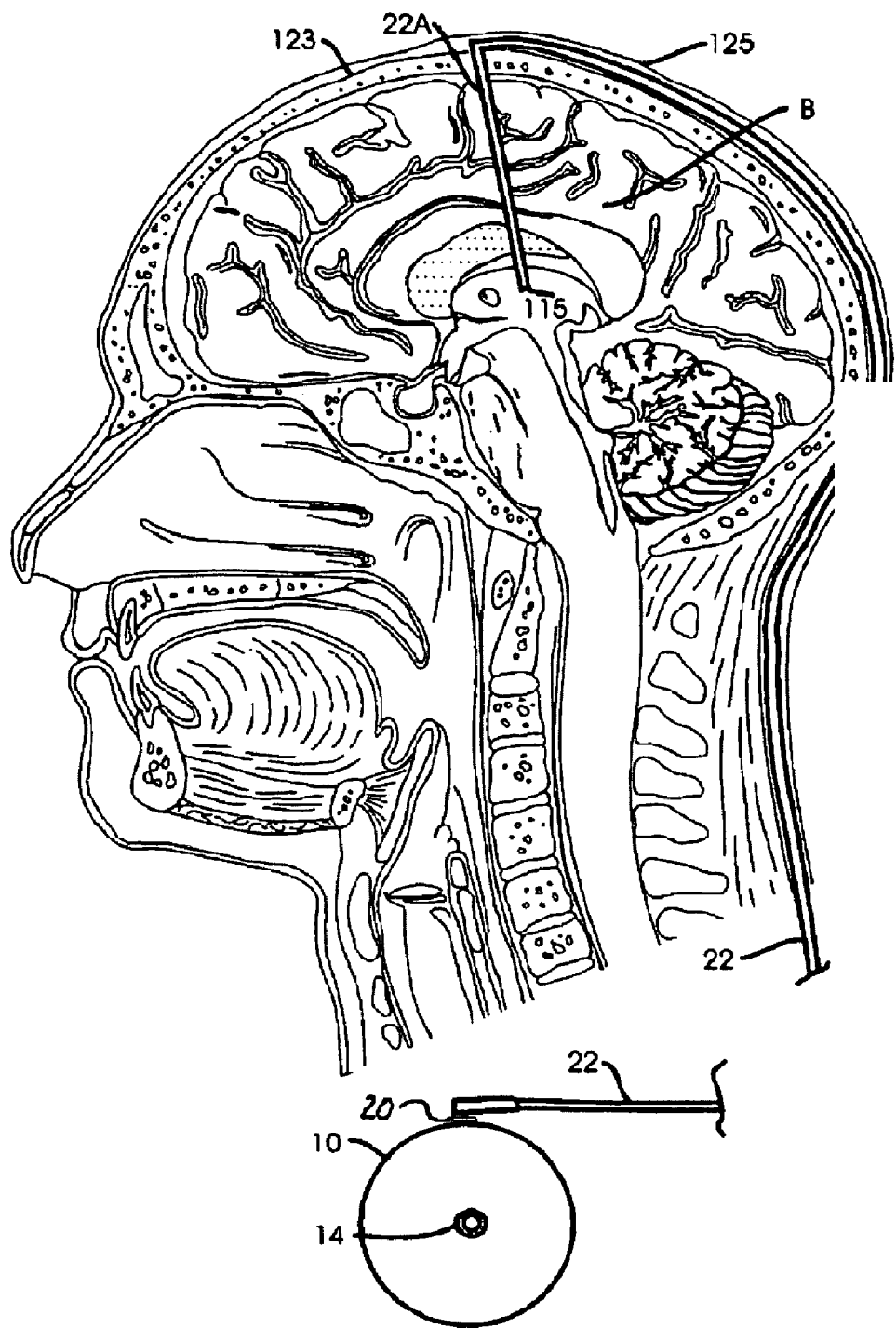
FIG. 13 is a schematic drawing of a view of a section of a patient showing an implanted infusion device and associated catheter implanted.

One suitable system for administering a therapeutic agent to the brain is discussed in U.S. Pat. No. 5,711,316 (Elsberry). Referring to FIG. 13, a system or infusion device 10 may be implanted below the skin of a subject. The device 10 may have a port 14 into which a hypodermic needle can be inserted through the skin to inject a quantity of a composition comprising a therapeutic agent. The composition is delivered from device 10 through a catheter port 20 into a catheter 22. Catheter 22 is positioned to deliver the agent to specific infusion sites in a brain (B). Device 10 may take the form of the like-numbered device shown in U.S. Pat. No. 4,692,147 (Duggan), assigned to Medtronic, Inc., Minneapolis, Minn., or take the form of a SYNCHROMED II® (Medtronic, Inc.) infusion device. The distal end of catheter 22 terminates in a cylindrical hollow tube 22A having a distal end 115 implanted into a target portion of the brain by conventional stereotactic surgical techniques. Additional details about end 115, according to various embodiments, may be obtained from U.S. application Ser. No. 08/430,960 entitled "Intraparenchymal Infusion Catheter System," filed Apr. 28, 1995 in the name of Dennis Elsberry et al. and assigned to the same assignee as the present application. Tube 22A is surgically implanted through a hole in the skull 123 and catheter 22 is implanted between the skull and the scalp 125 as shown in FIG. 13. Catheter 22 may be coupled to implanted device 10 in the manner shown or in any other suitable manner.

Figure 14:
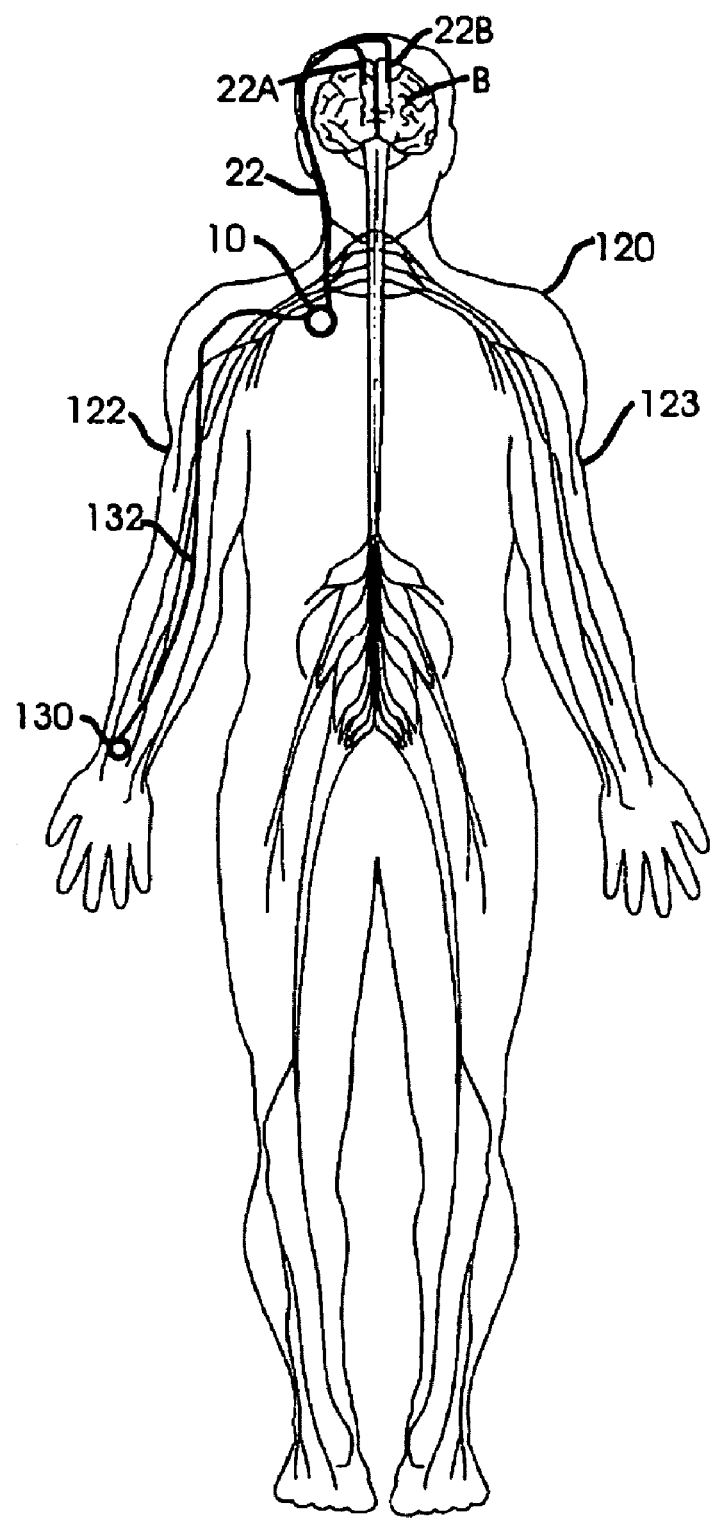
FIG. 14 is a schematic drawing of a view showing an implanted infusion device and associated catheter in the environment of a patient.

Referring to FIG. 14, a therapy delivery device 10 is implanted in a human body 120 in the location shown or may be implanted in any other suitable location. Body 120 includes arms 122 and 123. In various embodiments and as depicted, catheter 22 is divided into twin or similar tubes 22A and 22B that are implanted into the brain bilaterally. In some embodiments, tube 22B is supplied with a composition from a separate catheter and pump. Of course, unilateral delivery may be performed in accordance with the teachings presented herein.

Figure 15:
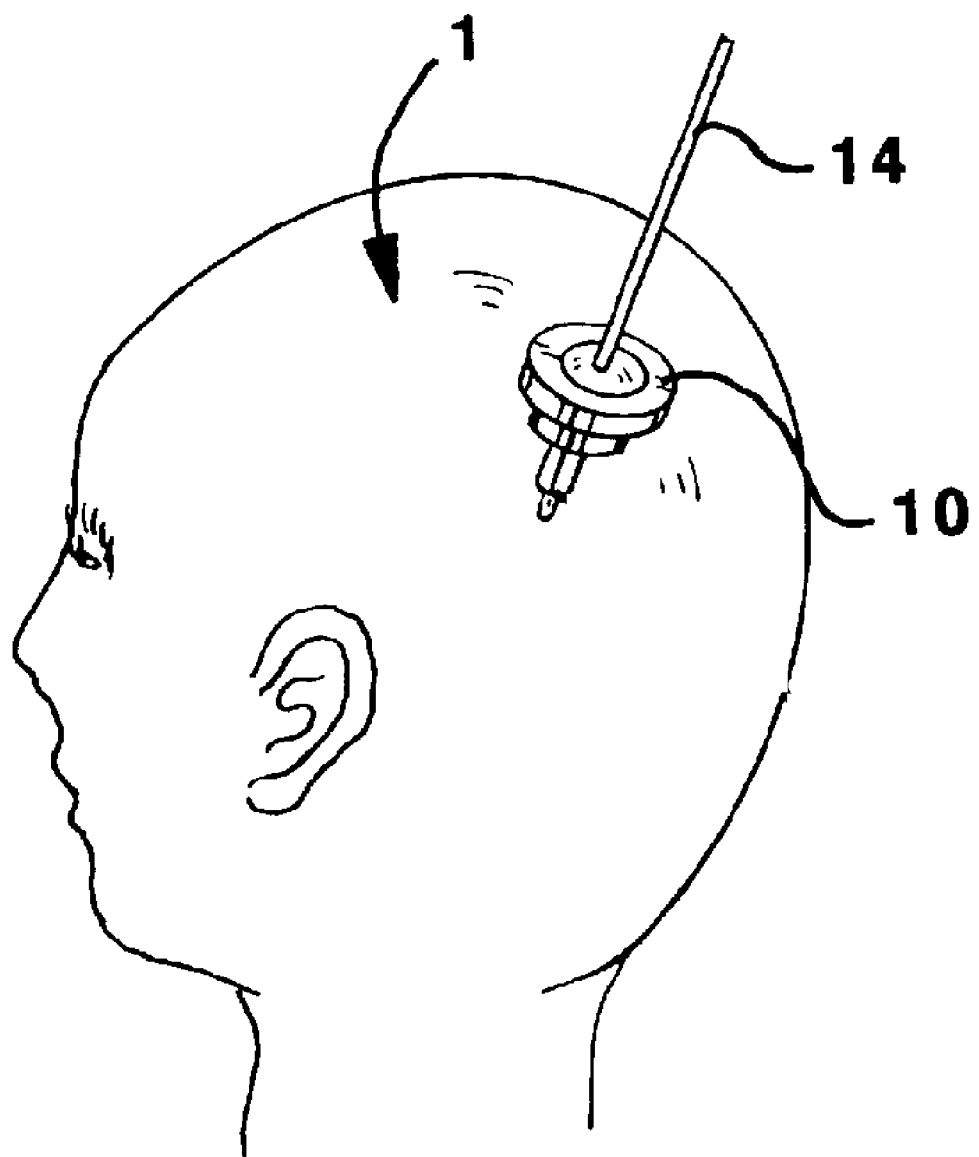
FIG. 15 is a schematic drawing of a view showing an injection port in the environment of a patient.

Referring to FIG. 15, a humanized anti-Aβ antibody may be delivered to a subject's CNS via an injection port 10 implanted subcutaneously in the scalp of a patient 1, e.g. as described in U.S. Pat. No. 5,954,687 or otherwise known in the art. A guide catheter 10 may be used to guide an infusion catheter through port 10 to a target location. Of course, an infusion catheter may be directly be inserted through port 10 to the target location.

Any other known or developed implantable or external infusion device or port may be employed.

Figure 16:
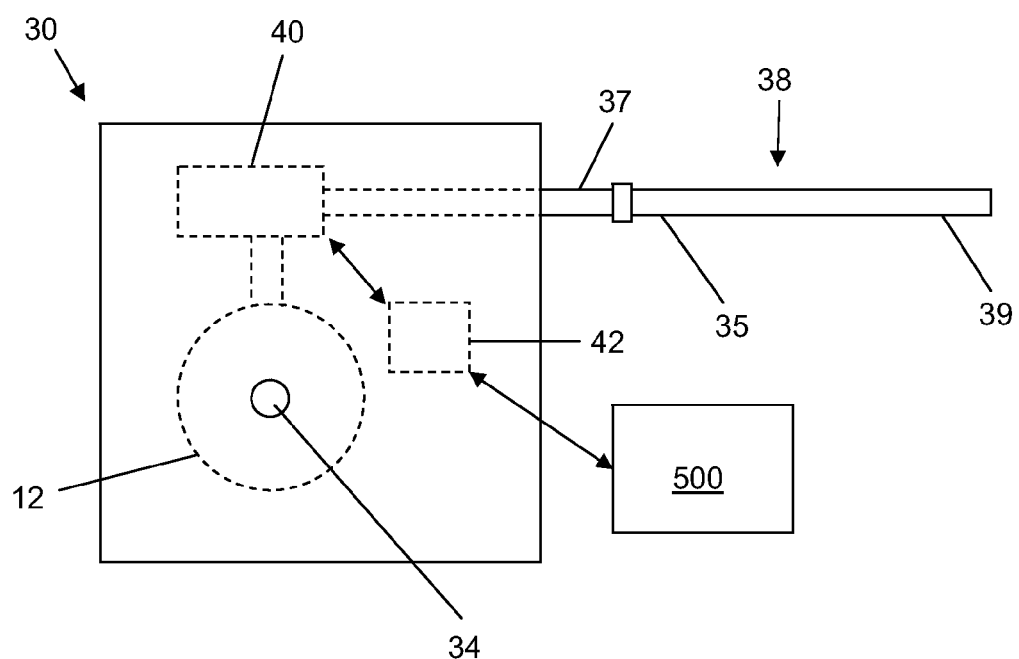
FIG. 16 is a schematic drawing of a side view of a representative system including an infusion device and a sensor, showing some internal components in block form.

Referring to FIG. 16, a representative system including an infusion device 30 and a sensor 500 is shown. The sensor 500 may detect an attribute of the nervous system, which attribute may reflect a pathology associated with a disease to be treated or studied or the amount of antibody already in the targeted region. A microprocessor 42 may analyze output from the sensor 50 and regulate the amount of antibody delivered to the brain. Sensor 500 may be operably coupled to processor 42 in any manner. For example, sensor 500 may be connected to processor via a direct electrical connection, such as through a wire or cable, or via wireless communication. Sensed information, whether processed or not, may be recoded by device 30 and stored in memory (not shown). The stored sensed memory may be relayed to an external programmer, where a physician may modify one or more parameter associated with the therapy based on the relayed information. Alternatively, based on the sensed information, processor 42 may adjust one or more parameters associated with therapy delivery. For example, processor 42 may adjust the amount or timing of the infusion of an anti-Aβ antibody. It will be understood that two or more sensors 500 may be employed.

Sensor 500 may detect a polypeptide associated with a CNS disorder to be treated or investigated; a physiological effect, such as a change in membrane potential; a clinical response, such as blood pressure; or the like. In various embodiments, a component of an infused composition, such as the anti-Aβ antibody or other component, which may be added specifically for the purpose of detection by the sensor 500, is detected. Any suitable sensor 500 may be used. A biosensor may be used to detect the presence of a polypeptide or other molecule in a patient. Any known or future developed biosensor may be used. The biosensor may have, e.g., an enzyme, an antibody, a receptor, or the like operably coupled to, e.g., a suitable physical transducer capable of converting the biological signal into an electrical signal. In some situations, receptors or enzymes that reversibly bind the molecule being detected may be preferred. In various embodiments, sensor 500 is a sensor as described in, e.g., U.S. Pat. No. 5,978,702, entitled TECHNIQUES OF TREATING EPILEPSY BY BRAIN STIMULATION AND DRUG INFUSION, or U.S. patent application Ser. No. 10/826,925, entitled COLLECTING SLEEP QUALITY INFORMATION VIA A MEDICAL DEVICE, filed Apr. 15, 2004, or U.S. patent application Ser. No. 10/820,677, entitled DEVICE AND METHOD FOR ATTENUATING AN IMMUNE RESPONSE, filed Apr. 8, 2004.

Examples of sensor technology that may be adapted for use in some embodiments include those disclosed in: (i) U.S. Pat. No. 5,640,764 for "Method of forming a tubular feed-through hermetic seal for an implantable medical device;" (ii) U.S. Pat. No. 5,660,163 for "Glucose sensor assembly;" (iii) U.S. Pat. No. 5,750,926 for "Hermetically sealed electrical feedthrough for use with implantable electronic devices;" (iv) U.S. Pat. No. 5,791,344 for "Patient monitoring system;" (v) U.S. Pat. No. 5,917,346 for "Low power current to frequency converter circuit for use in implantable sensors;" (vi) U.S. Pat. No. 5,957,958 for "Implantable electrode arrays;" (vii) U.S. Pat. No. 5,999,848 for "Daisy chainable sensors and stimulators for implantation in living tissue;" (viii) U.S. Pat. No. 6,043,437 for "Alumina insulation for coating implantable components and other microminiature devices;" (ix) U.S. Pat. No. 6,088,608 for "Electrochemical sensor and integrity tests therefor;" or (x) U.S. Pat. No. 6,259,937 for "Implantable substrate sensor."

EXAMPLES

In the Examples that follow, recombinant DNA techniques were performed using methods well known in the art and, as appropriate, supplier instructions for use of enzymes were used in these methods. Sources of general methods included Molecular Cloning, A Laboratory Manual, $3^{rd}$ edition, vols 1-3, eds. Sambrook and Russel (2001) Cold Spring Harbor Laboratory Press, and Current Protocols in Molecular Biology, ed. Ausubel, John Wiley and Sons. Detailed laboratory methods are also described below. Analysis of T cell epitopes was performed according to methods published in PCT/GB2007/000736 (Antitope Ltd).

Example 1

Chimeric 6E10 mRNA was extracted from the hybridoma 6E10 cells (Covance, Inc., Emeryville, Calif.) using a Poly A Tract System 1000 mRNA extraction kit (Promega Corp. Madison Wis.) according to manufacturer's instructions. mRNA was reverse transcribed as follows. For the kappa light chain, 5.0 microliter of mRNA was mixed with 1.0 microliter of 20 pmol/microliter MuIgGκ$V_L$-3' primer OL040 (Table 2) and 5.5 microliter nuclease free water (Promega Corp. Madison Wis.). For the lambda light chain, 5.0 microliter of mRNA was mixed with 1.0 microliter of 20 pmol/microliter MuIgGλ$V_L$-3' primer OL042 (Table 2) and 5.5 microliter nuclease free water (Promega Corp. Madison Wis.). For the gamma heavy chain, 5 microliter of mRNA was mixed with 1.0 microliter of 20 pmol/microliter MuIgG$V_H$-3' primer OL023 (Table 1) and 5.5 µl nuclease free water (Promega Corp. Madison Wis.). All three reaction mixes were placed in the pre-heated block of the thermal cycler set at 70° C. for 5 minutes. These were chilled on ice for 5 minutes before adding to each 4.0 microliter ImPromII 5× reaction buffer (Promega Corp. Madison Wis.), 0.5 microliter RNasin ribonuclease inhibitor (Promega Corp. Madison Wis.), 2.0 microliter 25 mM $MgCl_2$ (Promega Corp. Madison Wis.), 1.0 microliter 10 mM dNTP mix (Invitrogen, Paisley UK) and 1.0 microliter Improm II reverse transcriptase (Promega Corp. Madison Wis.). The reaction mixes were incubated at room temperature for 5 minutes before being transferred to a pre-heated PCR block set at 42° C. for 1 hour. After this time the reverse transcriptase was heat inactivated by incubating at 70° C. in a PCR block for fifteen minutes.

Heavy and light chain sequences were amplified from cDNA as follows: A PCR master mix was prepared by adding 37.5 microliter 10× Hi-Fi Expand PCR buffer: (Roche, Mannheim Germany), 7.5 microliter 10 mM dNTP mix (Invitrogen, Paisley UK) and 3.75 microliter Hi-Fi Expand DNA polymerase (Roche, Mannheim Germany) to 273.75 microliter nuclease free water. This master mix was dispensed in 21.5 microliter aliquots into 15 thin walled PCR reaction tubes on ice. Into six of these tubes was added 2.5 microliter of MuIgVH-3' reverse transcription reaction mix and 1.0 microliter of heavy chain 5' primer pools HA to HF (see Table 1 for primer sequences and primer pool constituents). To another seven tubes was added 2.5 microliter of MuIgKVL-3' reverse transcription reaction and 1.0 microliter of light chain 5' primer pools LA to LG (Table 2). Into the final tube was added 2.5 microliter of MuIgKVL-3' reverse transcription reaction and 1.0 microliter of lambda light chain primer MuIgλVL5'-LI. Reactions were placed in the block of the thermal cycler and heated to 95° C. for 2 minutes. The PCR reaction was performed for 40 cycles of 94° C. for 30 seconds, 55° C. for 1 minute and 72° C. for 30 seconds. Finally the PCR products were heated at 72° C. for 5 minutes, and then held at 4° C.

Amplification products were cloned into pGEM-T easy vector using the pGEM-T easy Vector System I (Promega Corp. Madison Wis.) kit and sequenced. The resultant mouse VH (SEQ. ID. NO. 36) and VL (SEQ. ID. NO. 37) sequences are shown in FIG. 2 ("Mouse").

For generation of a chimeric antibody, VH region genes were amplified by PCR using the primers OL330, GAT-CACGCGTGTCCACTCCGAAGTGCAGCTG-GTGGAGTC (SEQ ID NO. 63), and OL331, GTACAAGCT-TACCTGAGGAGACGGTGACTGAGG (SEQ ID NO. 64); these were designed to engineer in a 5' MluI and a 3' HindIII restriction enzyme site using plasmid DNA from one of the cDNA clones as template. Into a 0.5 ml PCR tube was added 5 microliter 10× Hi-Fi Expand PCR buffer: (Roche, Mannheim Germany), 1.0 microliter 10 mM dNTP mix (Invitrogen, Paisley UK), 0.5 microliter of Primer OL330, 0.5 microliter of primer OL331, 1.0 microliter template DNA and 0.5 microliter Hi-Fi Expand DNA polymerase (Roche, Mannheim Germany) to 41.5 microliter nuclease free water.

VL regions were amplified in a similar method using the oligonucleotides OL332, CATGGCGCGCGATGTGA-CATCCAGATGACTCAGTC (SEQ ID NO. 65), and OL333, TGCGGGATCCAACTGAGGAAGCAAAGTT-TAAATTCTACTCACGTCTCAGCTCCA GCTTGGTCC (SEQ ID NO. 66), to engineer in BssHII and BamHI restriction enzyme sites. Reactions were placed in the block of the thermal cycler and heated to 95° C. for 2 minutes. The polymerase chain reaction (PCR) was performed for 30 cycles of 94° C. for 30 seconds, 55° C. for 1 minute and 72° C. for 30 seconds. Finally the PCR products were heated at 72° C. for 5 minutes, and then held at 4° C. VH and VL region PCR products were then cloned into the vectors pANT15 and pANT13 respectively (FIG. 1) at the MluI/HindIII and BssHII/BamHI sites respectively. Both pANT15 and pANT13 are pAT153-based plasmids containing a human Ig expression cassette. The heavy chain cassette in pANT15 consists of a human genomic IgG1 constant region gene driven by hCMVie promoter, with a downstream human IgG polyA region. pANT15 also contains a hamster dhfr gene driven by the SV40 promoter with a downstream SV40 polyA region. The light chain cassette of pANT13 includes the genomic human kappa constant region driven by hCMVie promoter with downstream light chain polyA region. Cloning sites between a human Ig leader sequence and the constant regions allow the insertion of the variable region genes.

NS0 cells (ECACC 85110503, Porton, UK) were co-transfected with these two plasmids via electroporation and selected in DMEM (Invitrogen, Paisley UK)+5% FBS (Ultra low IgG Cat No. 16250-078 Invitrogen, Paisley UK)+Penicillin/Streptomycin (Invitrogen, Paisley UK)+100 nM Methotrexate (Sigma, Poole UK). Methotrexate resistant colonies were isolated and antibody was purified by Protein A affinity chromatography using a 1 ml HiTrap MabSelect Sure column (GE Healthcare, Amersham UK) following the manufacturers recommended conditions.

NS0 supernatants were quantified for antibody expression in IgG Fc/Kappa ELISA using purified human IgG1/Kappa (Sigma, Poole UK) as standards. Immunosorb 96 well plates (Nalge nunc Hereford, UK) were coated with mouse anti-human IgG Fc-specific antibody (16260 Sigma, Poole UK) diluted at 1:1500 in 1×PBS (pH 7.4) at 37° C. for 1 hour. Plates were washed three times in PBS+0.05% Tween 20 before adding samples and standards, diluted in 2% BSA/PBS. Plates were incubated at RT for 1 hour before washing three times in PBS/Tween and adding 100 µl/well of detecting antibody goat anti-human kappa light chain peroxidase conjugate (A7164 Sigma, Poole UK) diluted 1:1000 in 2% BSA/PBS. Plates were incubated at RT for 1 hour before washing five times with PBS/tween and bound antibody detected using OPD substrate (Sigma, Poole UK). The assay was developed in the dark for 5 minutes before being stopped by the addition of 3M HCl. The assay plate was then read in a MRX TCII plate reader (Dynex Technologies, Worthing, UK) at 490 nm.

The chimeric antibody was tested in an ELISA-based competition assay using 6E10 mouse antibody, biotinylated using Biotintag micro biotinylation kit (Sigma, Poole UK).

Biotinylated mouse 6E10 antibody was diluted to 0.25 µg/ml and mixed with equal volumes of competing antibody at concentrations ranging from 3 ng/ml-16 µg/ml. 100 µl of the antibody mixes were transferred into the wells of Immulon Maxisorb plates precoated with 0.06125 µg/ml Abeta$_{42}$ beta amyloid peptide coated plates and incubated at room temperature for 1 hour. The plate was washed, and bound biotinylated mouse 6E10 was detected by adding a strepavidin-HRP conjugate (Sigma, Poole UK) (diluted at 1:500) and OPD substrate (Sigma, Poole UK). The assay was developed in the dark for 5 minutes before being stopped by the addition of 3M HCl. The assay plate was then read in a MRX TCII plate reader at absorbance 490 nm.

TABLE 1

Primer sequences and primer pool constituents

| Code | Sequence | Length | Name-Pool |
|---|---|---|---|
| OL007 | ATGRASTTSKGGYTMARCTKGR TTT (SEQ ID NO: 1) | 25 | MuIgV$_H$5'-HA |
| OL008 | ATGRAATGSASCTGGGTYWTYC TCTT (SEQ ID NO: 2) | 26 | MuIgV$_H$5'-HB |
| OL009 | ATGGACTCCAGGCTCAATTTAG TTTTCCT (SEQ ID NO: 3) | 29 | MuIgV$_H$5'-HC |
| OL010 | ATGGCTGTCYTRGBGCTGYTCY TCTG (SEQ ID NO: 4) | 26 | MuIgV$_H$5'-HC |
| OL011 | ATGGVTTGGSTGTGGAMCTTGC YATTCCT (SEQ ID NO: 5) | 29 | MuIgV$_H$5'-HC |
| OL012 | ATGAAATGCAGCTGGRTYATST TCTT (SEQ ID NO: 6) | 26 | MuIgV$_H$5'-HD |

TABLE 1-continued

Primer sequences and primer pool constituents

| Code | Sequence | Length | Name-Pool |
|---|---|---|---|
| OL013 | ATGGRCAGRCTTACWTYYTCAT TCCT (SEQ ID NO: 7) | 26 | MuIgV$_H$5'H-D |
| OL014 | ATGATGGTGTTAAGTCTTCTGT ACCT (SEQ ID NO: 8) | 26 | MuIgV$_H$5'-HD |
| OL015 | ATGGGATGGAGCTRTATCATSY TCTT (SEQ ID NO: 9) | 26 | MuIgV$_H$5'-HE |
| OL016 | ATGAAGWTGTGGBTRAACTGG RT (SEQ ID NO: 10) | 23 | MuIgV$_H$5'-HE |
| OL017 | ATGGRATGGASCKKIRTCTTTM TCT (SEQ ID NO: 11) | 25 | MuIgV$_H$5'-HE |
| OL018 | ATGAACTTYGGGYTSAGMTTGR TTT (SEQ ID NO: 12) | 25 | MuIgV$_H$5'-HF |
| OL019 | ATGTACTTGGGACTGAGCTGTG TAT (SEQ ID NO: 13) | 25 | MuIgV$_H$5'-HF |
| OL020 | ATGAGAGTGCTGATTCTTTTG TG (SEQ ID NO: 14) | 23 | MuIgV$_H$5'-HF |
| OL021 | ATGGATTTTGGGCTGATTTTTT TTATTG (SEQ ID NO: 15) | 28 | MuIgV$_H$5'-HF |
| OL023 | CCAGGGRCCARKGGATARACIG RTGG (SEQ ID NO: 16) | 26 | MuIgGV$_H$3'-2 |

TABLE 2

Primer sequences and primer pool constituents

| Code | Sequence | Length | Name-Pool |
|---|---|---|---|
| OL024 | ATGRAGWCACAKWCYCAGGTC TTT (SEQ. ID. NO: 17) | 24 | MuIgkV$_L$5'-LA |
| OL025 | ATGGAGACAGACACACTCCTG CTAT (SEQ. ID. NO: 18) | 25 | MuIgkV$_L$5'-LB |
| OL026 | ATGGAGWCAGACACACTSCTG YTATGGGT (SEQ. ID. NO: 19) | 29 | MuIgkV$_L$5'-LC |
| OL027 | ATGAGGRCCCCTGCTCAGWTT YTTGGIWTCTT (SEQ. ID. NO: 20) | 32 | MuIgkV$_L$5'-LD |
| OL028 | ATGGGCWTCAAGATGRAGTCA CAKWYYCWGG (SEQ. ID. NO: 21) | 31 | MuIgkV$_L$5'-LD |
| OL029 | ATGAGTGTGCYCACTCAGGTC CTGGSGTT (SEQ. ID. NO: 22) | 29 | MuIgkV$_L$5'-LE |

TABLE 2-continued

Primer sequences and primer pool constituents

| Code | Sequence | Length | Name-Pool |
|---|---|---|---|
| OL030 | ATGTGGGAYCGKTTTYAMMC TTTTCAATTG (SEQ. ID. NO. 23) | 31 | MuIgkV$_L$5'-LE |
| OL031 | ATGGAAGCCCCAGCTCAGCTT CTCTTCC (SEQ. ID. NO. 24) | 28 | MuIgkV$_L$5'-LE |
| OL032 | ATGAGIMMKTCIMTTCAITTC YTGGG (SEQ. ID. NO. 25) | 26 | MuIgkV$_L$5'-LF |
| OL033 | ATGAKGTHCYCIGCTCAGYTY CTIRG (SEQ. ID. NO. 26) | 26 | MuIgkV$_L$5'-LF |
| OL034 | ATGGTRTCCWCASCTCAGTTC CTTG (SEQ. ID. NO. 27) | 25 | MuIgkV$_L$5'-LF |
| OL035 | ATGTATATATGTTTGTTGTCT ATTTCT (SEQ. ID. NO. 28) | 27 | MuIgkV$_L$5'-LF |
| OL036 | ATGAAGTTGCCTGTTAGGCTG TTGGTGCT (SEQ. ID. NO. 29) | 29 | MuIgkV$_L$5'-LG |
| OL037 | ATGGATTTWCARGTGCAGATT WTCAGCTT (SEQ. ID. NO. 30) | 29 | MuIgkV$_L$5'-LG |
| OL038 | ATGGTYCTYATVTCCTTGCTG TTCTGG (SEQ. ID. NO. 31) | 27 | MuIgkV$_L$5'-LG |
| OL039 | ATGGTYCTYATVTTRCTGCTG CTATGG (SEQ. ID. NO. 32) | 27 | MuIgkV$_L$5'-LG |
| OL040 | ACTGGATGGTGGGAAGATGGA (SEQ. ID. NO. 33) | 21 | MuIgkV$_L$3'-1 |
| OL041 | ATGGCCTGGAYTYCWCTYWTM YTCT (SEQ. ID. NO. 34) | 25 | MuIgλV$_L$5'-LI |
| OL042 | AGCTCYTCWGWGGAIGGYGGR AA (SEQ. ID. NO. 35) | 23 | MuIgλV$_L$3'-1 |

Example 2

Deimmunized 6E10

Peptides of 15 amino acids length with overlaps of 12 amino acids were synthesised from the VH and VL sequences of mouse 6E10 (FIG. 2). For VH and VL, 36 and 34 peptides respectively were synthesised, in both cases starting from the N terminal amino acid in the sequence. These peptides were then analysed in human T cell assays using the method described in PCT/GB2007/000736 (Antitope Ltd). This revealed the presence of four T cell epitopes from the following peptides:

| | |
|---|---|
| VH19-33 | (amino acids 19-33 of SEQ ID NO: 36) KLSCTASGFNIKDTY; |
| VH79-93 | (amino acids 79-93 of SEQ ID NO: 36) TAYLHLNSLTSEDTA; |
| VL10-24 and | (amino acids 10-24 of SEQ ID NO: 37) SLTVTAGEKVALTCK; |
| VL79-93 | (amino acids 79-93 of SEQ ID NO: 37) LTISSVQAEDLAVYY. |

The peptides are underline in the "mouse" sequence provided in FIG. 2.

A range of variants of these peptides were retested in human T cell assays incorporating amino acid substitutions for amino acids present at the corresponding positions in other antibody V regions. From this analysis, the following variant peptides were negative in human T cell assays (with substitutions underlined):

| | | |
|---|---|---|
| VH19-33 | K<u>V</u>SCTASGFNIKDTY | (SEQ ID NO: 38) |
| VH79-93 | TAY<u>MELSSLRS</u>EDTA | (SEQ ID NO: 39) |
| VL10-24 | SLTVTAGE<u>DA</u>ALTCK | (SEQ ID NO: 40) |
| VL79-93 | LTISSV<u>T</u>AEDLAVYY | (SEQ ID NO: 41) |

Deimmunized VH and VL sequences were designed to incorporate the variant peptide sequences as above. Sequences of the deimmunized variants (SEQ ID NO:42 and SEQ ID NO:43) are given in FIG. 2 ('DeI'). Deimmunized V region genes were constructed using the mouse 6E10 VH and VL templates for PCR using long overlapping oligonucleotides to introduce amino acids corresponding to the variant peptide sequences as above. Variant genes were cloned directly into the expression vectors pANT15 and pANT13 and transfected into NS0 as detailed in Example 1. Binding of deimmunized antibody was tested in the competition binding ELISA described in Example 1.

Example 3

Humanized 6E10

Humanized VH and VL sequences were designed by comparison of mouse 6E10 sequences and homologous human VH and VL sequences. From this analysis, the human VH region VH1-46 was chosen to provide frameworks for grafting of 6E10 VH CDRs as shown in FIG. 2 ('Graft1', SEQ ID NO:44). The human VL region B3 was chosen to provide frameworks for grafting of 6E10 VL CDRs as shown in FIG. 2 ('Graft', SEQ ID NO:45). A variant of the humanized VH sequence was designed as shown in FIG. 2 ('Graft2', SEQ ID NO:46) where six framework residues (amino acids 23, 48, 71, 73, 78 and 93 using Kabat numbering) were converted back to the corresponding mouse VH residues. The retention of these six amino acids was considered important due to internal folding or interactions with CDRs (for example, see US2006073137 (Celltech Limited)). Humanized V region genes were constructed using the mouse 6E10 VH and VL templates for PCR using long overlapping oligonucleotides to introduce amino acids from homologous human VH and VL sequences. Variant genes were cloned directly into the expression vectors pANT15 and pANT13 and transfected into NS0 as detailed in Example 1. Binding of humanized antibody variants were tested in the competition binding ELISA described in Example 1.

Example 4

Composite Human Antibody Variants of 6E10

Composite human VH and VL sequences were designed by comparison of mouse 6E10 sequences and fragments of different naturally occurring human VH and VL sequences and selection of such human fragments to build the composite human sequences. The choice of human VH and VL sequence fragments was constrained for the presence of certain amino acids at corresponding positions in 6E10 which were considered to be potentially important for antibody binding in conjunction with CDRs from 6E10. For VH, these amino acids were 1, 11, 23, 41, 48, 67, 71, 73, 76, 78 and 93 (Kabat numbering). For VL, these amino acids were 12, 63 and 70 (Kabat numbering). A bias was also used for the selection of human VH and VL sequence fragments where fragments were chosen for homology to certain human germline framework regions of closest homology to the 6E10 VH and VL. For VH, these were VH1-46 for framework 1 (VHFR1), VH1-58 for VHFR2, VH1-69 for VHFR3 and J4 for the J region. For VL, these were A14 for VLFR1, B3 for VLFR2, B3 for VHFR3 and J4 for the J region. From this analysis, a series of composite human VH and VL sequences were designed as shown in FIG. 2 (THAW, SEQ ID NOs: 47-54, corresponding nucleotide sequences are shown in FIGS. 3-5, SEQ ID NOs: 55-62). Composite human V region genes were constructed using the mouse 6E10 VH and VL templates for PCR using long overlapping oligonucleotides to introduce amino acids from human VH and VL sequence fragments.

Variant genes were cloned directly into the expression vectors pANT15 and pANT13 and transfected into NS0 as detailed in Example 1. All combinations of composite heavy and light chains (i.e. a total of 15 pairings) were stably transfected into NS0 cells by electroporation and selected in media (high glucose DMEM with L-glutamine and Na pyruvate, 5% ultra-low IgG FCS, pen/strep—all from Invitrogen, Paisley, UK) containing 200 nM methotrexate. Several drug resistant colonies for each construct were tested for expression levels and the best expressing lines were selected and frozen under liquid nitrogen.

Binding of humanized variants were tested in the competition binding ELISA described in Example 1. Briefly, supernatants from the best expressing lines for each combination were quantified using an Fc capture, Kappa light chain detection ELISA in comparison to a IgG1/kappa standard. The quantified supernatants were then tested in a competition ELISA for binding to their target antigen, beta amyloid. 96 well maxisorb plates (Nunc—Fisher Scientific, Loughborough, UK) were coated overnight at 4° C. with 50 µl/well of 0.06125 µg/ml beta amyloid (Covance, UK) in carbonate buffer pH 9.6. Duplicate titrations of mouse MDT-2007 antibody and COMPOSITE HUMAN ANTIBODY™ (Antitope Ltd.) samples were generated (in the range 0.003 µg/ml to 16 µg/ml) and mixed with a constant concentration (0.25 ug/ml) of biotinylated mouse MDT-2007 antibody in PBS pH 7.4/ 0.5% BSA/0.05% Tween. The titrations, 50 µl/well, were added to washed (3× with PBS pH 7.4/0.5% BSA/0.05% Tween 20) assay plates and incubated at room temperature for 1 hour. Plates were washed as above and 100 µl/well of a 1/500 dilution of streptavidin HRP (Sigma, Poole, UK) in PBS pH 7.4/0.5% BSA/0.05% Tween was added and incubated for a further 1 hour at room temperature. After a further wash, bound biotinylated mouse MDT-2007 antibody was detected with 100 µl/well TMB substrate. After stopping the reaction with 50 µl/well 3M HCl, absorbance was measured at 450 nm and the binding curves of the test antibodies were compared to the mouse reference standard. Absorbance was plotted against sample concentration and straight lines were fitted through each of the data sets. The equations of the lines were used to calculate the concentration required to inhibit Biotin-MDT-2007 binding to beta amyloid by 50% ($IC_{50}$). The $IC_{50}$ values were used to calculate the fold difference in binding efficiencies and these values are reported in Table 3.

TABLE 3

Anti-Beta Amyloid COMPOSITE HUMAN ANTIBODY ™ (Antitope Ltd.) Sequence Variants Matrix of Binding Efficiencies Relative to Mouse MDT-2007

|     | VK1  | VK2  | VK3  |
| --- | ---- | ---- | ---- |
| VH1 | 0.78 | —    | 1.93 |
| VH2 | —    | 1.10 | 0.96 |
| VH3 | —    | —    | 1.57 |
| VH4 | 0.94 | 0.67 | 1.36 |
| VH5 | 0.80 | 0.72 | 1.02 |

The data presented in Table 3 is from a competition assay. Anti-beta amyloid humanized antibodies were used in a competition assay with biotinylated mouse (6E10). $IC_{50}$ values were normalized against the binding of the mouse 6E10 anti-Aβ antibody so that 1 is equal to the mouse antibody binding and a value <1 is improved binding relative to mouse 6E10.

Based on these data and the sequences of the humanized antibodies, four antibodies were selected as lead candidates (highlighted in bold in Table 3). Cell lines for these variants were expanded to 100 ml and grown to saturation. Antibodies were purified from each culture via protein A affinity chromatography. Briefly, supernatants were pH adjusted with 0.1 volume of 10×PBS pH 7.4 and passed over 1 ml Mab Select Sure protein A columns (GE Healthcare, Amersham, UK). The columns were washed with 10 volumes of PBS pH 7.4 before elution with 50 mM citrate buffer pH 3.0. 1 ml fractions were collected and immediately neutralized with 0.1 ml of 1 m Tris-HCl pH 9.0. Protein containing fractions (as judged by absorbance at 280 nm) were pooled, buffer exchanged into PBS pH 7.4 and the purified antibodies stored at +4° C. An SDS-PAGE gel of 1 µg of each antibody was run and stained with coomassie blue. The concentrations of the antibodies were calculated by UV absorption based upon a calculated molar extinction coefficient such that $E_{0.1\%}$ at 280 nm=1.45.

The purified antibodies were tested for binding to beta amyloid via competition ELISA as described above (n=2). Titrations of the test antibodies were done from 0.003 µg/ml to 16 µg/ml in duplicate. Absorbance at 450 nm was measured and this was plotted against test antibody concentration.

Table 4 summarizes the results for the combinations of the composite VH and VK variant sequences obtained from a competition assay performed over a wide range of concentrations (0.003 µg/ml to 16 µg/ml) for the anti-beta amyloid antibodies. Three of the humanized antibodies have an $IC_{50}$ that is improved compared to the mouse reference, particularly VH4/VK2 that has a measured 1.72 fold increase in binding in this assay.

TABLE 4

IC$_{50}$ Values for Anti-Beta Amyloid
COMPOSITE HUMAN ANTIBODY ™
(Antitope Ltd.) Sequence Variants

| Antibody | IC50 µg/ml | Fold Difference |
|---|---|---|
| Mouse | 3.6 | 1 |
| VH4/VK1 | 4.1 | 1.14 |
| VH4/VK2 | 2.1 | 0.57 |
| VH5/VK1 | 3.3 | 0.91 |
| VH5/VK2 | 2.6 | 0.72 |

The data provided in Table 4 were obtained from a competition assay with biotinylated chimeric mouse 6E10 antibody. IC$_{50}$ values are displayed and are also normalized against the binding of chimeric mouse 6E10 so that 1 is equal to chimeric mouse 6E10 antibody binding and a value <1 is improved binding relative to chimeric mouse 6E10 antibody.

Tables 5-8 show the human sequences from which the humanized antibodies were derived.

TABLE 5

VH4 sequences from which humanized antibodies were derived

| Genbank Accession No. | VH4 Sequence |
|---|---|
| AAC18394 | QVQLVQSGAEVKKPGASVKVSC (SEQ ID NO: 67) |
| ABF83341 | SVKVSCTAS (SEQ ID NO: 68) |
| CAM57950 | ASGFNIKDTYIHWVRQA (SEQ ID NO: 69) |
| BAC02116 | ARGQRLEWIGR (SEQ ID NO: 70) |
| CAK50661 | GRFDP (SEQ ID NO: 71) |
| 1313976D | VNVN (SEQ ID NO: 72) |
| AAK68005 | NTRY (SEQ ID NO: 73) |
| AAK14005 | DS (SEQ ID NO: 74) |
| AAR32283 | RFRGRV (SEQ ID NO: 75) |
| AAR02486 | FRGRVTIT (SEQ ID NO: 76) |
| CAA85547 | RVTITSDASTNTAY (SEQ ID NO: 77) |
| BAC01408 | TAYMELSSLRSEDTAVYYC (SEQ ID NO: 78) |
| BAC02402 | EDTAVYYCSR (SEQ ID NO: 79) |
| ABK81616 | RSYY (SEQ ID NO: 80) |
| CAB56165 | YNG (SEQ ID NO: 81) |
| AAL59364 | GRR (SEQ ID NO: 82) |
| AAV40543 | RR (SEQ ID NO: 83) |
| AAA17922 | FTY (SEQ ID NO: 84) |
| IGHJ4*01 | YWGQGTLVTVSS (SEQ ID NO: 85) |

TABLE 6

VH5 sequences from which humanized antibodies were derived

| Genbank Accession No. | VH4 Sequence |
|---|---|
| AAC18394 | QVQLVQSGAEVKKPGASVKVSC (SEQ ID NO: 115) |
| ABF83341 | SVKVSCTAS (SEQ ID NO: 116) |
| CAM57950 | ASGFNIKDTYIHWVRQA (SEQ ID NO: 117) |
| BAC02116 | ARGQRLEWIGR (SEQ ID NO: 118) |
| CAK50661 | GRFDP (SEQ ID NO: 119) |
| 1313976D | VNVN (SEQ ID NO: 120) |
| AAK68005 | NTRY (SEQ ID NO: 121) |
| AAK14005 | DS (SEQ ID NO: 122) |
| AAR32283 | RFRGRV (SEQ ID NO: 123) |
| AAR02486 | FRGRVTIT (SEQ ID NO: 124) |
| CAA85547 | RVTITSDASTNTAY (SEQ ID NO: 125) |
| BAC01408 | TAYMELSSLRSEDTAVYYC (SEQ ID NO: 126) |
| BAC02402 | EDTAVYYCSR (SEQ ID NO: 127) |
| ABK81616 | RSYY (SEQ ID NO: 128) |
| CAB56165 | YNG (SEQ ID NO: 129) |
| AAL59364 | GRR (SEQ ID NO: 130) |
| AAV40543 | RR (SEQ ID NO: 131) |
| AAA17922 | FTY (SEQ ID NO: 132) |

TABLE 6-continued

VH5 sequences from which humanized antibodies were derived

| Genbank Accession No. | VH4 Sequence |
|---|---|
| IGHJ4*01 | YWGQGTLVTVSS (SEQ ID NO: 133) |

TABLE 7

VK1 sequences from which humanized antibodies were derived

| Genbank Accession No. | Vκ1 Sequence |
|---|---|
| CAA51125 | DIVMTQSPDSLTVSLGERATINCK (SEQ ID NO: 86) |
| AAQ21856 | CKASQS (SEQ ID NO: 87) |
| AAZ09112 | SQSLL (SEQ ID NO: 88) |
| CAA81698 | LSS (SEQ ID NO: 89) |
| CAE18257 | GNQ (SEQ ID NO: 90) |
| AAR89578 | KNYLTWYQQKPGQPPKLLIYWAS (SEQ ID NO: 91) |
| AAW67408 | WYQQKPGQPPKLLIYWASIRESGVPDRF (SEQ ID NO: 92) |
| BAC03964 | SGVPDRFTGSGSGT (SEQ ID NO: 93) |
| CAJ57189 | GSGSGTFFTLTIS (SEQ ID NO: 94) |
| BAC03964 | FTLTISSLQAEDVAVYYCQ (SEQ ID NO: 95) |
| AAQ21931 | YYCQN (SEQ ID NO: 96) |
| CAC94614 | DYNYP (SEQ ID NO: 97) |
| ABA26134 | PFTFG (SEQ ID NO: 98) |
| Human J2 | TFGQGTKLEIK (SEQ ID NO: 99) |

TABLE 8

VK2 sequences from which humanized antibodies were derived

| Genbank Accession No. | Vκ2 Sequence |
|---|---|
| AAD16249 | DIVMTQSPSSL (SEQ ID NO: 100) |
| AAO91645 | MTQSPSSLTASVGDRVTITC (SEQ ID NO: 101) |

TABLE 8-continued

VK2 sequences from which humanized antibodies were derived

| Genbank Accession No. | Vκ2 Sequence |
|---|---|
| AAQ21856 | CKASQS (SEQ ID NO: 102) |
| AAZ09112 | SQSLL (SEQ ID NO: 103) |
| CAA81698 | LSS (SEQ ID NO: 104) |
| CAE18257 | GNQ (SEQ ID NO: 105) |
| AAR89578 | KNYLTWYQQKPGQPPKLLIYWAS (SEQ ID NO: 106) |
| AAW67408 | WYQQKPGQPPKLLIYWASIRESGVPDRF (SEQ ID NO: 107) |
| BAC03964 | SGVPDRFTGSGSGT (SEQ ID NO: 108) |
| CAJ57189 | GSGSGTFFTLTIS (SEQ ID NO: 109) |
| BAC03964 | FTLTISSLQAEDVAVYYCQ (SEQ ID NO: 110) |
| AAQ21931 | YYCQN (SEQ ID NO: 111) |
| CAC94614 | DYNYP (SEQ ID NO: 112) |
| ABA26134 | PFTFG (SEQ ID NO: 113) |
| Human J2 | TFGQGTKLEIK (SEQ ID NO: 114) |

Example 5

Immunogenicity Study of Humanized Anti-Aβ Antibody, MDT-2007

Sequence variant VH4/VK2 (see Table 4) has been designated MDT-2007 and will be referred to hereinafter as MDT-2007. MDT-2007 was subjected to a pre-clinical ex vivo T cell assay (EPISCREEN™, Antitope Ltd.). The EPISCREEN™ (Antitope Ltd.) assay provides an effective technology for predicting T cell immunogenicity by quantifying T cell responses to protein therapeutics. Using a cohort of community blood donors carefully selected based on MHC class II haplotypes, purified antibodies are tested for T cell immunogenicity in vitro using the EPISCREEN™ (Antitope Ltd.) time course T cell assay format. This assay provides a method by which the immunogenicity of whole proteins can be assessed both in terms of magnitude and frequency of T cell responses (Jones et al., *J Interferon Cytokine Res.* 2004 24(9): 560-72; Jones et al., *J Thromb Haemost.* 2005 3(5):991-1000). Standard T cell assays provide a single time point 'snapshot' of the immune response and do not allow for natural variation in individual donors' response to antigens. The EpiScreen™ time course T cell assay samples donors' T cell responses over a four day period and the high degree of sensitivity along with the robust nature of the assay allows an accurate pre-clinical assessment of the potential for immunogenicity of the biologic being studied.

5.1. Methods 5.1.1 Purification of Antibodies

MDT-2007 (Lot No. MED01) was used as test antibody in the EPISCREEN™ (Antitope Ltd.) assay. Control chimeric antibody was prepared fresh as follows: a 1 L culture of chimeric antibody expressing cell-line was grown to saturation. Supernatant was separated from cells and debris, adjusted to pH 7.4, filter sterilized and run through 2× 1 ml Hi-Trap Mab Select Pure affinity columns (GE Healthcare, Amersham, UK) at a flow rate of 1 ml/min. The columns were washed with 20 ml PBS pH 7.4 and eluted with sodium citrate buffer pH 3.0. Fractions were immediately neutralized with 0.1 volumes 1M Tris buffer pH 9.0. The protein content of each fraction was measured by UV absorption at 280 nm and protein containing fractions were pooled, buffer exchanged into PBS pH 7.4 and concentrated. The antibody was further purified by size exclusion chromatography using a 16/60 Sephacryl S200 column (GE Healthcare, Amersham, UK). The major peak fractions were collected, pooled, filter sterilized and stored at +4° C.

Final concentrations were determined by UV absorption using calculated molar extinction coefficients, where A280 1.0=1.42 mg/ml. Each antibody was then diluted to 100 µg/ml in AIMV culture medium (Invitrogen, Paisley, UK).

5.1.2 Preparation and Selection of Donor PBMC

Peripheral blood mononuclear cells (PBMC) were isolated from healthy community donor buffy coats (from blood drawn within 24 hours) obtained from the National Blood Transfusion Service (Addenbrooke's Hospital, Cambridge, UK). PBMC were isolated from buffy coats by Lymphoprep (Axis-Shield, Dundee, UK) density centrifugation and CD8+ T cells were depleted using CD8+ ROSETTESEP™ (StemCell Technologies Inc., London, UK). Donors were characterized by identifying HLA-DR haplotypes using a Biotest SSP-PCR based tissue-typing kit (Biotest, Landsteinerstraβe, Denmark) as well as determining T cell responses to a control antigen keyhole limpet haemocyanin (KLH) (Pierce, Rockford, USA). PBMC were then frozen and stored in liquid nitrogen until required.

A cohort of 20 donors was selected to best represent the number and frequency of HLADR allotypes expressed in the world population. Analysis of the allotypes expressed in the cohort against those expressed in the world population revealed that coverage of >80% was achieved and that all major HLA-DR alleles (individual allotypes with a frequency >5% expressed in the world population) were well represented. Details of individual donor haplotypes and a comparison of the frequency of MHC class II allotypes expressed in the world population and the sample population can be found in Table 9 and FIG. 6, respectively.

5.1. Time Course T Cell Proliferation Assays

PBMCs from each donor were thawed, counted and viability assessed. Cells were revived in room temperature AIMV culture medium (Invitrogen, Paisley, UK) and resuspended in AIMV to 4-6×106 PBMC/ml. For each donor, bulk cultures were established in which a total of 1 ml proliferation cell stock was added a 24 well plate. A total of 1 ml of each diluted test sample was added to the PBMC to give a final concentration of 50 µg/ml per sample. For each donor, a positive control (cells incubated with 100 µg/ml KLH) and a negative control (cells incubated with culture media only) were also included. Cultures were incubated for a total of 8 days at 37° C. with 5% $CO_2$. On days 5, 6, 7 and 8, the cells in each well were gently resuspended and 3×100 µl aliquots transferred to individual wells of a round bottomed 96 well plate. The cultures were pulsed with 1 µCi [3H]-Thymidine (Perkin Elmer, Waltham, Mass., USA) in 100 µl AIMV culture medium and incubated for a further 18 hours before harvesting onto filter mats (Perkin Elmer, Waltham, Mass., USA) using a TomTec Mach III cell harvester. Counts per minute (cpm) for each well were determined by MELTILEX™ (Perkin Elmer, Waltham, Mass., USA) scintillation counting on a Microplate Beta Counter in paralux, low background counting.

5.1.4 Data Analysis

For proliferation assays, an empirical threshold of a stimulation index (SI) equal to or greater than 2 (SI≥2) has been previously established whereby samples inducing proliferative responses above this threshold are deemed positive (where included, borderline SIs≥1.95 are highlighted). Extensive assay development and previous studies have shown that this is the minimum signal to noise threshold allowing maximum sensitivity without detecting large numbers of false positive responses. For proliferation data sets (n=3), positive responses were defined by statistical and empirical thresholds:

1. Significance (p<0.05) of the response by comparing cpm of test wells against medium control wells using unpaired two sample student's t-test.
2. Stimulation index greater than 2 (SI≥2), where SI=mean of test wells (cpm)/mean medium control wells (cpm).

In addition, intra-assay variation was assessed by calculating the coefficient of variance and standard deviation (SD) of the raw data from replicate cultures.

5.2 Results

Both MDT-2007 and chimeric anti-Aβ42 were purified to homogeneity by Protein A affinity chromatography followed by size exclusion chromatography. Both preparations were derived from single peaks representing monomeric, non-aggregated antibody.

The two test samples were tested against a cohort of 20 healthy donors using EPISCREEN™ (Antitope Ltd.) time course T cell assays in order to determine the relative risk of immunogenicity. The cohort was selected to best represent the number and frequency of HLA-DR allotypes expressed in the world population (FIG. 6). Donor haplotypes and the results of the control antigen tests are shown in Table 1. The samples were tested at a final concentration of 50 µg/ml based on Antitope's previous experience showing that this saturating concentration is sufficient to stimulate detectable protein-specific T cell responses. The results from the current EPISCREEN™ (Antitope Ltd.) time course proliferation assay with MDT-2007 and chimeric antibody are shown in FIG. 7 and summarised in Table 10.

The chimeric antibody stimulated responses in 4 of the 20 donors where the SI≥2, and significance was achieved in the Student's t-test with 5 donors (donor 1 gave a borderline SI of 1.96 that was significantly different from control), a rate of 25% (FIG. 7(a)). In contrast none of the donors responded to MDT2007. Results with the control antigen KLH show that the correlation between positive and negative results in Test 1 and Test 2 is good (Table 9), thus validating the assay. In addition all the basal cpm for the control wells are above the minimum specification for the assay of 150 cpm (Table 2).

5.3 Conclusions

In general, the positive proliferation responses observed in the EPISCREEN™ (Antitope Ltd.) time course T cell assay against the chimeric antibody was in the expected range of 20-40%. Based on previous experience with other therapeutic antibodies if the frequency of responses >10% there is an association with an increased risk of immunogenicity in the clinic (FIG. 8). Importantly, frequent and potent T cell responses were observed against the control antigen, KLH, that indicate that the assay functioned as expected. The results also show that MDT-2007 failed to induce any positive responses in any donors which indicates that the frequency of positive responses is <5%, and therefore falls below the 10% threshold.

FIG. 8 shows a clear correlation between the level of immunogenicity observed using the EPISCREEN™ (Antitope Ltd.) assay and the level of immunogenicity (anti-protein therapeutic antibody responses) that has been actually observed in the clinic against a large panel of therapeutic proteins (Baker and Jones, *Curr. Opin. Drug. Disc. Dev.* 2007. 10:219-217). High levels of immunogenicity were observed in both the clinical data and EPISCREEN™ (Antitope Ltd.) assays for proteins such as Infliximab and Campath, whereas relatively low levels of immunogenicity were observed for proteins such as Xolair, Herceptin, and Avastin. It is clear that MDT-2007 would therefore be considered as having a low potential risk of immunogenicity.

TABLE 9

HLA class II haplotypes and details of the study population.

| Donor No. | Haplotpe | Test 1 | MED01 |
|---|---|---|---|
| 1 | DRB1*01, DRB1*11, DRB3 | 3.31 | 4.15 |
| 2 | DRB1*09, DRB1*15, DRB4, DRB5 | 1.79 | 2.59 |
| 3 | DRB1*15, DRB1*10, DRB5 | 1.17 | 0.89 |
| 4 | DRB1*07, DRB1*08, DRB4 | 1.8 | 0.51 |
| 5 | DRB1*14, DRB1*15, DRB3, DRB5 | 2.98 | 2.06 |
| 6 | DRB1*04, DRB1*16, DRB4, DRB5 | 1.86 | 1.70 |
| 7 | DRB1*03, DRB1*13, DRB3 | 4.91 | 0.97 |
| 8 | DRB1*07, DRB1*15, DRB4, DRB5 | 1.15 | 1.96 |
| 9 | DRB1*04, DRB1*07, DRB4 | 10.31 | 4.08 |
| 10 | DRB1*03, DRB1*04, DRB3, DRB4 | 2.91 | 3.82 |
| 11 | DRB1*03, DRB1*13, DRB3 | n/d | 2.16 |
| 12 | DRB1*07, DRB1*13, DRB3, DRB4 | 1.81 | 2.46 |
| 13 | DRB1*03, DRB1*11, DRB3 | 1.08 | 1.79 |
| 14 | DRB1*04, DRB1*07, DRB4 | 5.98 | 2.78 |
| 15 | DRB1*13, DRB3 | 8.16 | 2.76 |
| 16 | DRB1*11, DRB1*13, DRB3 | 3.39 | 3.06 |
| 17 | DRB1*03, DRB3 | 4.42 | 2.03 |
| 18 | DRB1*07, DRB1*11, DRB3, DRB4 | 3.41 | 3.96 |
| 19 | DRB1*03, DRB1*11, DRB3, DRB4 | n/d | 5.17 |
| 20 | DRB1*01, DRB1*04, DRB4 | 2.54 | 3.03 |

In Table 9, donor responses (SI) to KLH are shown for two independent tests. Test 1 was performed on freshly isolated PBMC and MED01 is from the current study. KLH-specific responses were measured on day 8 post stimulation for both tests values in bold text are considered as positive proliferation responses. Underlined values indicate differences in the test result (i.e. positive or negative).

TABLE 10

Summary of positive donor proliferation responses to chimeric anti-Aβ42 and MDT-2007.

| Donor No. | Chimeric | MDT-2007 | Basal CPM |
|---|---|---|---|
| 1 | +* | − | 1089 |
| 2 | − | − | 980 |
| 3 | − | − | 1183 |
| 4 | − | − | 2903 |
| 5 | − | − | 1115 |
| 6 | − | − | 1266 |
| 7 | − | − | 682 |
| 8 | − | − | 492 |
| 9 | − | − | 546 |
| 10 | + | − | 1442 |
| 11 | − | − | 2162 |
| 12 | − | − | 1968 |
| 13 | − | − | 909 |
| 14 | + | − | 454 |
| 15 | − | − | 719 |
| 16 | − | − | 1451 |
| 17 | − | − | 2880 |
| 18 | − | − | 5209 |
| 19 | + | − | 1883 |
| 20 | + | − | 404 |
| Positive Responses | 5 (25%) | 0 (0%) | |

In Table 10, positive proliferation (+) responses are indicated along with borderline proliferation (*) positive responses (SI range 1.95-1.99). All responses shown were significantly (p<0.05) different from untreated control wells. The mean counts per minute (cpm) are shown for untreated control wells (basal rate).

Example 6

Binding of MDT-2007 to Brains of AD Human and Aged Non-Human Primate

Brain sections were washed 3 times with TBS (TBS=12.1 g Tris, 9.0 g NaCl in one Lit dH2O) PH 7.4 with HCl then incubated with Sodium meta per Iodate for 20 min ((2.139 Na meta Per Iodate/100 mL TBS). Sections were then washed with Wash with TBS/0.25% Triton 3 times and blocked with TBS/Triton/Goat Serum (3%) for 30 min, followed by a blocking wash consisting of TBS/Triton/Blocking Serum (1%). After blocking, the sections were incubated with Fab fragment Goat anti-Human IgG 1:200/TBS (Jackson Immuno Research Laboratory. Cat #109-007-003)/Triton 0.1%/and G.S 1% for 1 Hour followed by wash step with TBS. The primary antibody of interest (MDT-2007) was then added to the sections 1:10K in TBS/Triton/Goat Serum (1%)/ 1° Ab and kept overnight on shaker table at room temp. The second day, sections were washed with TBS/1% Blocking Serum three times and then incubated with 2Ab Biotin SP Conjugated AffiniPur Goat anti-Human IgG (Jackson Immuno Research Laboratory. Cat #109-065-003) 1:200/ TBS/1% Blocking serum for 1 Hr. Sections were washed with TBS and then incubated again with ABC 135 ul of A+ 135 ul of B/50 mL TBS (1:500) for 1 hr. Sections were then rinsed with Imidizole Acetate Buffer 3 times (0.68 g Imidizole, 6.8 g. NaAc Trihydrate/1 L $dH_2O$, pH w/glacial Acetic Acid to 7.4)

As shown in FIG. 9, MDT-2007 bound to amyloid plaques in brains of both the aged rhesus monkey (A) and the 84 year-old female human diagnosed end stage Alzheimer's disease (eight year disease course) (B). The staining was more intense in the rhesus monkey than the human, with the human having a higher background and less intense plaque staining. Brains sections of a 26 yr old stump tail monkey were also stained (not shown) and resulted less staining compared to the rhesus monkey shown in FIG. 9A.

Example 7

Stability of MDT-2007 in Infusion System Under Implant Conditions

Stability of MDT-2007 in a delivery system (SYN-CHROMED II® (Medtronic, Inc.) implantable infusion device and Model 8910 polyurethane catheter, Medtronic, Inc.) was tested at two different concentrations and under two different flow parameters. MDT-2007 was diluted in Dulbecco's 1× PBS (without calcium and magnesium) to achieve 0.1 mg/ml and 1 mg/ml injectable compositions of MDT-2007. In the first cycle (4 wk duration) pumps were run at 600 ul/day flow rate. In the second cycle (8 wk duration), upon refill of the pumps, the pumps were run at 300 ul/day flow rate. All test conditions simulate potential clinical use (37° C. set up, flow rates, concentrations, refill interval).

The flow rate (i.e., the function of the pump) was not affected by the MDT-2007 formulations, possibly indicating that the MDT-2007 did not aggregate or precipitate and cause pump malfunction. MDT-2007 was found to be stable with 80% or greater recovery of active MDT-2007 (based on ELISA) infused from the infusion system. The 20% loss is believed to be due to adsorption of the antibody to components of the system, as steady state delivery was reached quickly.

Thus, embodiments of HUMANIZED ANTI-AMYLOID BETA ANTIBODIES are disclosed. One skilled in the art will appreciate that the cell culture apparatuses and methods described herein can be practiced with embodiments other than those disclosed. The disclosed embodiments are presented for purposes of illustration and not limitation.

What is claimed is:

1. An isolated anti-amyloid beta antibody comprising:
   a variable heavy chain region including an amino acid sequence selected from the group consisting of SEQ ID NOs: 42, 44, 46, 47, 48, 49, 50 and 51; and
   a variable light chain region including an amino acid sequence selected from the group consisting of SEQ ID NOs: 43, 45, 52, 53 and 54,
   with the proviso that if the variable heavy chain region includes the amino acid sequence of SEQ ID NO:50, the variable light chain region does not include the amino acid sequence of SEQ ID NO:53.

2. The antibody of claim 1, further comprising an immunoglobulin domain.

3. The antibody of claim 2, wherein the immunoglobulin domain is selected from the group consisting of IgG-1, IgG-4, and IgGM.

4. The antibody of claim 1, wherein the antibody is a monoclonal antibody.

5. The antibody of claim 1, wherein the antibody is a F(ab)'$_2$ antibody.

6. The antibody of claim 1, wherein the variable heavy chain region comprises an amino acid sequence selected from the group consisting of SEQ ID NO:47, SEQ ID NO:48, SEQ ID NO:49 and SEQ ID NO:51.

7. The antibody of claim 6, wherein the variable light chain region comprises an amino acid sequence selected from the group consisting of SEQ ID NO:52 and SEQ ID NO:54.

8. The antibody of claim 1, wherein the variable heavy chain region comprises the amino acid sequence of SEQ ID NO:47 and the variable light chain region comprises the amino acid sequence of SEQ ID NO:52.

9. The antibody of claim 1, wherein the variable heavy chain region comprises the amino acid sequence of SEQ ID NO:48 and the variable light chain region comprises the amino acid sequence of SEQ ID NO:54.

10. The antibody of claim 1, wherein the variable heavy chain region comprises the amino acid sequence of SEQ ID NO:50 and the variable light chain region comprises the amino acid sequence of SEQ ID NO:52.

11. The antibody of claim 1, wherein the variable heavy chain region comprises the amino acid sequence of SEQ ID NO:51 and the variable light chain region comprises the amino acid sequence of SEQ ID NO:52.

12. The antibody of claim 1, wherein the variable heavy chain region comprises the amino acid sequence of SEQ ID NO:51 and the variable light chain region comprises the amino acid sequence of SEQ ID NO:53.

13. A composition comprising the antibody of claim 1.

14. The composition of claim 13, further comprising a pharmaceutically acceptable diluent.

15. The composition of claim 14, wherein the antibody is present in the composition in an amount effective to treat a disease associated with increased or aberrant soluble A$\beta$, A$\beta$ fibrils or A$\beta$ plaques when administered to a subject in need thereof.

16. A system comprising an implantable infusion device and the composition of claim 15, wherein the composition is an injectable composition, wherein the infusion device comprises a reservoir for housing the composition, and wherein the composition is housed in the reservoir.

* * * * *

SEQUENCE LISTING

```
<160> NUMBER OF SEQ ID NOS: 133

<210> SEQ ID NO 1
<211> LENGTH: 25
<212> TYPE: DNA
<213> ORGANISM: Artificial Sequence
<220> FEATURE:
<223> OTHER INFORMATION: Synthetic primer

<400> SEQUENCE: 1
atgrasttsk ggytmarctk grttt                                          25

<210> SEQ ID NO 2
<211> LENGTH: 26
<212> TYPE: DNA
<213> ORGANISM: Artificial Sequence
<220> FEATURE:
<223> OTHER INFORMATION: Synthetic primer

<400> SEQUENCE: 2
atgraatgsa sctgggtywt yctctt                                         26

<210> SEQ ID NO 3
<211> LENGTH: 29
<212> TYPE: DNA
<213> ORGANISM: Artificial Sequence
<220> FEATURE:
<223> OTHER INFORMATION: Synthetic primer

<400> SEQUENCE: 3
atggactcca ggctcaattt agttttcct                                      29

<210> SEQ ID NO 4
<211> LENGTH: 26
<212> TYPE: DNA
<213> ORGANISM: Artificial Sequence
<220> FEATURE:
<223> OTHER INFORMATION: Synthetic primer

<400> SEQUENCE: 4
atggctgtcy trgbgctgyt cytctg                                         26

<210> SEQ ID NO 5
<211> LENGTH: 29
<212> TYPE: DNA
<213> ORGANISM: Artificial Sequence
<220> FEATURE:
<223> OTHER INFORMATION: Synthetic primer

<400> SEQUENCE: 5
atggvttggs tgtggamctt gcyattcct                                      29
```

<210> SEQ ID NO 6
<211> LENGTH: 26
<212> TYPE: DNA
<213> ORGANISM: Artificial Sequence
<220> FEATURE:
<223> OTHER INFORMATION: Synthetic primer

<400> SEQUENCE: 6
atgaaatgca gctggrtyat sttctt                                          26

<210> SEQ ID NO 7
<211> LENGTH: 26
<212> TYPE: DNA
<213> ORGANISM: Artificial Sequence
<220> FEATURE:
<223> OTHER INFORMATION: Synthetic primer

<400> SEQUENCE: 7
atggrcagrc ttacwtyytc attcct                                          26

<210> SEQ ID NO 8
<211> LENGTH: 26
<212> TYPE: DNA
<213> ORGANISM: Artificial Sequence
<220> FEATURE:
<223> OTHER INFORMATION: Synthetic primer

<400> SEQUENCE: 8
atgatggtgt taagtcttct gtacct                                          26

<210> SEQ ID NO 9
<211> LENGTH: 26
<212> TYPE: DNA
<213> ORGANISM: Artificial Sequence
<220> FEATURE:
<223> OTHER INFORMATION: Synthetic primer

<400> SEQUENCE: 9
atgggatgga gctrtatcat sytctt                                          26

<210> SEQ ID NO 10
<211> LENGTH: 23
<212> TYPE: DNA
<213> ORGANISM: Artificial Sequence
<220> FEATURE:
<223> OTHER INFORMATION: Synthetic primer

<400> SEQUENCE: 10
atgaagwtgt ggbtraactg grt                                             23

<210> SEQ ID NO 11
<211> LENGTH: 25
<212> TYPE: DNA
<213> ORGANISM: Artificial Sequence
<220> FEATURE:
<223> OTHER INFORMATION: Synthetic primer
<220> FEATURE:
<221> NAME/KEY: n
<222> LOCATION: (15)..(15)
<223> OTHER INFORMATION: "n" is inosine
<220> FEATURE:
<221> NAME/KEY: misc_feature
<222> LOCATION: (15)..(15)
<223> OTHER INFORMATION: n is a, c, g, or t

<400> SEQUENCE: 11
atggratgga sckknrtctt tmtct                                           25

```
<210> SEQ ID NO 12
<211> LENGTH: 25
<212> TYPE: DNA
<213> ORGANISM: Artificial Sequence
<220> FEATURE:
<223> OTHER INFORMATION: Synthetic primer

<400> SEQUENCE: 12
atgaacttyg ggytsagmtt grttt                                    25

<210> SEQ ID NO 13
<211> LENGTH: 25
<212> TYPE: DNA
<213> ORGANISM: Artificial Sequence
<220> FEATURE:
<223> OTHER INFORMATION: Synthetic primer

<400> SEQUENCE: 13
atgtacttgg gactgagctg tgtat                                    25

<210> SEQ ID NO 14
<211> LENGTH: 23
<212> TYPE: DNA
<213> ORGANISM: Artificial Sequence
<220> FEATURE:
<223> OTHER INFORMATION: Synthetic primer

<400> SEQUENCE: 14
atgagagtgc tgattctttt gtg                                      23

<210> SEQ ID NO 15
<211> LENGTH: 28
<212> TYPE: DNA
<213> ORGANISM: Artificial Sequence
<220> FEATURE:
<223> OTHER INFORMATION: Synthetic primer

<400> SEQUENCE: 15
atggattttg ggctgatttt ttttattg                                 28

<210> SEQ ID NO 16
<211> LENGTH: 26
<212> TYPE: DNA
<213> ORGANISM: Artificial Sequence
<220> FEATURE:
<223> OTHER INFORMATION: Synthetic primer
<220> FEATURE:
<221> NAME/KEY: n
<222> LOCATION: (21)..(21)
<223> OTHER INFORMATION: "n" is inosine
<220> FEATURE:
<221> NAME/KEY: misc_feature
<222> LOCATION: (21)..(21)
<223> OTHER INFORMATION: n is a, c, g, or t

<400> SEQUENCE: 16
ccagggrcca rkggatarac ngrtgg                                   26

<210> SEQ ID NO 17
<211> LENGTH: 24
<212> TYPE: DNA
<213> ORGANISM: Artificial Sequence
<220> FEATURE:
<223> OTHER INFORMATION: Synthetic primer

<400> SEQUENCE: 17
atgragwcac akwcycaggt cttt                                     24
```

<210> SEQ ID NO 18
<211> LENGTH: 25
<212> TYPE: DNA
<213> ORGANISM: Artificial Sequence
<220> FEATURE:
<223> OTHER INFORMATION: Synthetic primer

<400> SEQUENCE: 18
atggagacag acacactcct gctat                                              25

<210> SEQ ID NO 19
<211> LENGTH: 29
<212> TYPE: DNA
<213> ORGANISM: Artificial Sequence
<220> FEATURE:
<223> OTHER INFORMATION: Synthetic primer

<400> SEQUENCE: 19
atggagwcag acacactsct gytatgggt                                          29

<210> SEQ ID NO 20
<211> LENGTH: 32
<212> TYPE: DNA
<213> ORGANISM: Artificial Sequence
<220> FEATURE:
<223> OTHER INFORMATION: Synthetic primer
<220> FEATURE:
<221> NAME/KEY: n
<222> LOCATION: (27)..(27)
<223> OTHER INFORMATION: "n" is inosine
<220> FEATURE:
<221> NAME/KEY: misc_feature
<222> LOCATION: (27)..(27)
<223> OTHER INFORMATION: n is a, c, g, or t

<400> SEQUENCE: 20
atgaggrccc ctgctcagwt tyttggnwtc tt                                      32

<210> SEQ ID NO 21
<211> LENGTH: 31
<212> TYPE: DNA
<213> ORGANISM: Artificial Sequence
<220> FEATURE:
<223> OTHER INFORMATION: Synthetic primer

<400> SEQUENCE: 21
atgggcwtca agatgragtc acakwyycwg g                                       31

<210> SEQ ID NO 22
<211> LENGTH: 29
<212> TYPE: DNA
<213> ORGANISM: Artificial Sequence
<220> FEATURE:
<223> OTHER INFORMATION: Synthetic primer

<400> SEQUENCE: 22
atgagtgtgc ycactcaggt cctggsgtt                                          29

<210> SEQ ID NO 23
<211> LENGTH: 31
<212> TYPE: DNA
<213> ORGANISM: Artificial Sequence
<220> FEATURE:
<223> OTHER INFORMATION: Synthetic primer

<400> SEQUENCE: 23
atgtggggay cgktttyamm cttttcaatt g                                       31

```
<210> SEQ ID NO 24
<211> LENGTH: 28
<212> TYPE: DNA
<213> ORGANISM: Artificial Sequence
<220> FEATURE:
<223> OTHER INFORMATION: Synthetic primer

<400> SEQUENCE: 24
atggaagccc cagctcagct tctcttcc                                              28

<210> SEQ ID NO 25
<211> LENGTH: 26
<212> TYPE: DNA
<213> ORGANISM: Artificial Sequence
<220> FEATURE:
<223> OTHER INFORMATION: synthetic primer
<220> FEATURE:
<221> NAME/KEY: n
<222> LOCATION: (6)..(6)
<223> OTHER INFORMATION: "n" is inosine
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: n
<222> LOCATION: (12)..(12)
<223> OTHER INFORMATION: "n" is inosine
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: n
<222> LOCATION: (18)..(18)
<223> OTHER INFORMATION: "n" is inosine
<220> FEATURE:
<221> NAME/KEY: misc_feature
<222> LOCATION: (18)..(18)
<223> OTHER INFORMATION: n is a, c, g, or t

<400> SEQUENCE: 25
atgagnmmkt cnmttcantt cytggg                                                26

<210> SEQ ID NO 26
<211> LENGTH: 26
<212> TYPE: DNA
<213> ORGANISM: Artificial Sequence
<220> FEATURE:
<223> OTHER INFORMATION: Synthetic primer
<220> FEATURE:
<221> NAME/KEY: n
<222> LOCATION: (12)..(12)
<223> OTHER INFORMATION: "n" is inosine
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: n
<222> LOCATION: (24)..(24)
<223> OTHER INFORMATION: "n" is inosine
<220> FEATURE:
<221> NAME/KEY: misc_feature
<222> LOCATION: (24)..(24)
<223> OTHER INFORMATION: n is a, c, g, or t

<400> SEQUENCE: 26
atgakgthcy cngctcagyt yctnrg                                                26

<210> SEQ ID NO 27
<211> LENGTH: 25
```

```
<212> TYPE: DNA
<213> ORGANISM: Artificial Sequence
<220> FEATURE:
<223> OTHER INFORMATION: Synthetic primer

<400> SEQUENCE: 27
atggtrtccw casctcagtt ccttg                                    25

<210> SEQ ID NO 28
<211> LENGTH: 27
<212> TYPE: DNA
<213> ORGANISM: Artificial Sequence
<220> FEATURE:
<223> OTHER INFORMATION: Synthetic primer

<400> SEQUENCE: 28
atgtatatat gtttgttgtc tatttct                                  27

<210> SEQ ID NO 29
<211> LENGTH: 29
<212> TYPE: DNA
<213> ORGANISM: Artificial Sequence
<220> FEATURE:
<223> OTHER INFORMATION: Synthetic primer

<400> SEQUENCE: 29
atgaagttgc ctgttaggct gttggtgct                                29

<210> SEQ ID NO 30
<211> LENGTH: 29
<212> TYPE: DNA
<213> ORGANISM: Artificial Sequence
<220> FEATURE:
<223> OTHER INFORMATION: Synthetic primer

<400> SEQUENCE: 30
atggatttwc argtgcagat twtcagctt                                29

<210> SEQ ID NO 31
<211> LENGTH: 27
<212> TYPE: DNA
<213> ORGANISM: Artificial Sequence
<220> FEATURE:
<223> OTHER INFORMATION: Synthetic primer

<400> SEQUENCE: 31
atggtyctya tvtccttgct gttctgg                                  27

<210> SEQ ID NO 32
<211> LENGTH: 27
<212> TYPE: DNA
<213> ORGANISM: Artificial Sequence
<220> FEATURE:
<223> OTHER INFORMATION: Synthetic Primer

<400> SEQUENCE: 32
atggtyctya tvttrctgct gctatgg                                  27

<210> SEQ ID NO 33
<211> LENGTH: 21
<212> TYPE: DNA
<213> ORGANISM: Artificial Sequence
<220> FEATURE:
<223> OTHER INFORMATION: Synthetic primer

<400> SEQUENCE: 33
actggatggt gggaagatgg a                                        21
```

<210> SEQ ID NO 34
<211> LENGTH: 25
<212> TYPE: DNA
<213> ORGANISM: Artificial Sequence
<220> FEATURE:
<223> OTHER INFORMATION: Synthetic primer

<400> SEQUENCE: 34
atggcctgga ytycwctywt mytct                                          25

<210> SEQ ID NO 35
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: n
<222> LOCATION: (15)..(15)
<223> OTHER INFORMATION: "n" is inosine
<220> FEATURE:
<221> NAME/KEY: misc_feature
<222> LOCATION: (15)..(15)
<223> OTHER INFORMATION: n is a, c, g, or t

<400> SEQUENCE: 35
agctcytcwg wgganggygg raa                                            23

<210> SEQ ID NO 36
<211> LENGTH: 120
<212> TYPE: PRT
<213> ORGANISM: Artificial Sequence
<220> FEATURE:
<223> OTHER INFORMATION: Chimeric polypeptide

<400> SEQUENCE: 36

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Phe Asp Pro Val Asn Val Asn Thr Arg Tyr Asp Ser Arg Phe
    50                  55                  60

Arg Gly Lys Ala Thr Ile Thr Ser Asp Ala Ser Ser Asn Thr Ala Tyr
65                  70                  75                  80

Leu His Leu Asn Ser Leu Thr Ser Glu Asp Thr Ala Val Tyr Tyr Cys
                85                  90                  95

Ser Arg Ser Tyr Tyr Asn Gly Arg Arg Phe Thr Tyr Trp Gly Gln
            100                 105                 110

Gly Thr Leu Val Thr Val Ser Ala
        115                 120

<210> SEQ ID NO 37
<211> LENGTH: 113
<212> TYPE: PRT
<213> ORGANISM: Artificial Sequence
<220> FEATURE:
<223> OTHER INFORMATION: Chimeric polypeptide

<400> SEQUENCE: 37

Asp Ile Val Met Thr Gln Ser Pro Ser Ser Leu Thr Val Thr Ala Gly
1               5                   10                  15

```
Glu Lys Val Ala Leu Thr Cys Lys Ala Ser Gln Ser Leu Leu Ser Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Ile Arg Glu Ser Gly Val
 50                  55                  60

Pro Asp Arg Phe Thr Gly Ser Gly Ser Gly Thr Phe Phe Thr Leu Thr
 65                  70                  75                  80

Ile Ser Ser Val Gln Ala Glu Asp Leu Ala Val Tyr Tyr Cys Gln Asn
                85                  90                  95

Asp Tyr Asn Tyr Pro Phe Thr Phe Gly Ser Gly Thr Lys Leu Glu Ile
                100                 105                 110

Lys

<210> SEQ ID NO 38
<211> LENGTH: 15
<212> TYPE: PRT
<213> ORGANISM: Artificial Sequence
<220> FEATURE:
<223> OTHER INFORMATION: Polypeptide variant

<400> SEQUENCE: 38

Lys Val Ser Cys Thr Ala Ser Gly Phe Asn Ile Lys Asp Thr Tyr
 1               5                  10                  15

<210> SEQ ID NO 39
<211> LENGTH: 15
<212> TYPE: PRT
<213> ORGANISM: Artificial Sequence
<220> FEATURE:
<223> OTHER INFORMATION: Variant polypeptide

<400> SEQUENCE: 39

Thr Ala Tyr Met Glu Leu Ser Ser Leu Arg Ser Glu Asp Thr Ala
 1               5                  10                  15

<210> SEQ ID NO 40
<211> LENGTH: 15
<212> TYPE: PRT
<213> ORGANISM: Artificial Sequence
<220> FEATURE:
<223> OTHER INFORMATION: Polypeptide variant

<400> SEQUENCE: 40

Ser Leu Thr Val Thr Ala Gly Glu Asp Ala Ala Leu Thr Cys Lys
 1               5                  10                  15

<210> SEQ ID NO 41
<211> LENGTH: 15
<212> TYPE: PRT
<213> ORGANISM: Artificial Sequence
<220> FEATURE:
<223> OTHER INFORMATION: polypeptide variant

<400> SEQUENCE: 41

Leu Thr Ile Ser Ser Val Thr Ala Glu Asp Leu Ala Val Tyr Tyr
 1               5                  10                  15

<210> SEQ ID NO 42
<211> LENGTH: 120
<212> TYPE: PRT
<213> ORGANISM: Artificial Sequence
<220> FEATURE:
<223> OTHER INFORMATION: Deimunized heavy chain
```

-continued

```
<400> SEQUENCE: 42

Glu Val Gln Leu Gln Gln Ser Gly Ala Glu Leu Val Lys Pro Gly Ala
1               5                   10                  15

Ser Val Lys Val Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Phe Asp Pro Val Asn Val Asn Thr Arg Tyr Asp Ser Arg Phe
    50                  55                  60

Arg Gly Lys Ala Thr Ile Thr Ser Asp Ala Ser Ser Asn Thr Ala Tyr
65                  70                  75                  80

Met Glu Leu Ser Ser Leu Arg Ser Glu Asp Thr Ala Val Tyr Tyr Cys
                85                  90                  95

Ser Arg Ser Tyr Tyr Asn Gly Arg Arg Arg Phe Thr Tyr Trp Gly Gln
            100                 105                 110

Gly Thr Leu Val Thr Val Ser Ala
        115                 120

<210> SEQ ID NO 43
<211> LENGTH: 113
<212> TYPE: PRT
<213> ORGANISM: Artificial Sequence
<220> FEATURE:
<223> OTHER INFORMATION: Deimmunized Light Chain

<400> SEQUENCE: 43

Asp Ile Val Met Thr Gln Ser Pro Ser Ser Leu Thr Val Thr Ala Gly
1               5                   10                  15

Glu Asp Ala Ala Leu Thr Cys Lys Ala Ser Gln Ser Leu Leu Ser Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Thr Gly Ser Gly Ser Gly Thr Phe Phe Thr Leu Thr
65                  70                  75                  80

Ile Ser Ser Val Thr Ala Glu Asp Leu Ala Val Tyr Tyr Cys Gln Asn
                85                  90                  95

Asp Tyr Asn Tyr Pro Phe Thr Phe Gly Ser Gly Thr Lys Leu Glu Ile
            100                 105                 110

Lys

<210> SEQ ID NO 44
<211> LENGTH: 120
<212> TYPE: PRT
<213> ORGANISM: Artificial Sequence
<220> FEATURE:
<223> OTHER INFORMATION: Graft Heavy Chain

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Ile His Trp Val Arg Gln Ala Pro Gly Gln Gly Leu Glu Trp Met
        35                  40                  45

Gly Arg Phe Asp Pro Val Asn Val Asn Thr Arg Tyr Asp Ser Arg Phe
    50                  55                  60
```

```
Arg Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Tyr Tyr Asn Gly Arg Arg Phe Thr Tyr Trp Gly Gln
            100                 105                 110

Gly Thr Leu Val Thr Val Ser Ser
        115                 120

<210> SEQ ID NO 45
<211> LENGTH: 113
<212> TYPE: PRT
<213> ORGANISM: Artificial Sequence
<220> FEATURE:
<223> OTHER INFORMATION: Graft Light Chain

<400> SEQUENCE: 45

Asp Ile Val Met Thr Gln Ser Pro Asp Ser Leu Ala Val Ser Leu Gly
 1               5                  10                  15

Glu Arg Ala Thr Ile Asn Cys Lys Ala Ser Gln Ser Leu Leu Ser Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Asp Tyr Asn Tyr Pro Phe Thr Phe Gly Gln Gly Thr Lys Leu Glu Ile
            100                 105                 110

Lys

<210> SEQ ID NO 46
<211> LENGTH: 120
<212> TYPE: PRT
<213> ORGANISM: Artificial Sequence
<220> FEATURE:
<223> OTHER INFORMATION: Graft Heavy Chain

<400> SEQUENCE: 46

Gln Val Gln Leu Val Gln Ser Gly Ala Glu Val Lys Lys Pro Gly Ala
 1               5                  10                  15

Ser Val Lys Val Ser Cys Thr Ala Ser Gly Phe Asn Ile Lys Asp Thr
            20                  25                  30

Tyr Ile His Trp Val Arg Gln Ala Pro Gly Gln Gly Leu Glu Trp Ile
        35                  40                  45

Gly Arg Phe Asp Pro Val Asn Val Asn Thr Arg Tyr Asp Ser Arg Phe
    50                  55                  60

Arg Gly Arg Val Thr Met Thr Ser Asp Ala Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ser Arg Ser Tyr Tyr Asn Gly Arg Arg Phe Thr Tyr Trp Gly Gln
            100                 105                 110

Gly Thr Leu Val Thr Val Ser Ser
        115                 120
```

```
<210> SEQ ID NO 47
<211> LENGTH: 120
<212> TYPE: PRT
<213> ORGANISM: Artificial Sequence
<220> FEATURE:
<223> OTHER INFORMATION: Composite human heavy chain

<400> SEQUENCE: 47

Glu Val Gln Leu Val Gln Ser Gly Ala Glu Leu Lys Lys Pro Gly Ala
1               5                   10                  15

Ser Val Lys Val Ser Cys Thr Ala Ser Gly Phe Asn Ile Lys Asp Thr
            20                  25                  30

Tyr Ile His Trp Val Arg Gln Ala Pro Gly Gln Arg Leu Glu Trp Ile
        35                  40                  45

Gly Arg Phe Asp Pro Val Asn Val Asn Thr Arg Tyr Asp Ser Arg Phe
    50                  55                  60

Arg Gly Arg Ala Thr Ile Thr Ser Asp Ala Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ser Arg Ser Tyr Tyr Asn Gly Arg Arg Arg Phe Thr Tyr Trp Gly Gln
            100                 105                 110

Gly Thr Leu Val Thr Val Ser Ser
        115                 120

<210> SEQ ID NO 48
<211> LENGTH: 120
<212> TYPE: PRT
<213> ORGANISM: Artificial Sequence
<220> FEATURE:
<223> OTHER INFORMATION: Composite human heavy chain

<400> SEQUENCE: 48

Glu Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Lys Asp Thr
            20                  25                  30

Tyr Ile His Trp Val Arg Gln Ala Arg Gly Gln Arg Leu Glu Trp Ile
        35                  40                  45

Gly Arg Phe Asp Pro Val Asn Val Asn Thr Arg Tyr Asp Ser Arg Phe
    50                  55                  60

Arg Gly Arg Ala Thr Ile Thr Ser Asp Ala Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ser Arg Ser Tyr Tyr Asn Gly Arg Arg Arg Phe Thr Tyr Trp Gly Gln
            100                 105                 110

Gly Thr Leu Val Thr Val Ser Ser
        115                 120

<210> SEQ ID NO 49
<211> LENGTH: 120
<212> TYPE: PRT
<213> ORGANISM: Artificial Sequence
<220> FEATURE:
<223> OTHER INFORMATION: Composite Human Heavy Chain

<400> SEQUENCE: 49

Gln Val Gln Leu Val Gln Ser Gly Ala Glu Val Lys Lys Pro Gly Ala
1               5                   10                  15
```

Ser Val Lys Val Ser Cys Thr Ala Ser Gly Phe Asn Ile Lys Asp Thr
                20                  25                  30

Tyr Ile His Trp Val Arg Gln Ala Arg Gly Gln Arg Leu Glu Trp Ile
            35                  40                  45

Gly Arg Phe Asp Pro Val Asn Val Asn Thr Arg Tyr Asp Ser Arg Phe
    50                  55                  60

Arg Gly Arg Ala Thr Ile Thr Ser Asp Ala Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ser Arg Ser Tyr Tyr Asn Gly Arg Arg Phe Thr Tyr Trp Gly Gln
            100                 105                 110

Gly Thr Leu Val Thr Val Ser Ser
        115                 120

<210> SEQ ID NO 50
<211> LENGTH: 120
<212> TYPE: PRT
<213> ORGANISM: Artificial Sequence
<220> FEATURE:
<223> OTHER INFORMATION: Composite Human Heavy Chain

<400> SEQUENCE: 50

Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Lys Asp Thr
                20                  25                  30

Tyr Ile His Trp Val Arg Gln Ala Arg Gly Gln Arg Leu Glu Trp Ile
            35                  40                  45

Gly Arg Phe Asp Pro Val Asn Val Asn Thr Arg Tyr Asp Ser Arg Phe
    50                  55                  60

Arg Gly Arg Val Thr Ile Thr Ser Asp Ala Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ser Arg Ser Tyr Tyr Asn Gly Arg Arg Phe Thr Tyr Trp Gly Gln
            100                 105                 110

Gly Thr Leu Val Thr Val Ser Ser
        115                 120

<210> SEQ ID NO 51
<211> LENGTH: 120
<212> TYPE: PRT
<213> ORGANISM: Artificial Sequence
<220> FEATURE:
<223> OTHER INFORMATION: Composite Human Heavy Chain

<400> SEQUENCE: 51

Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Lys Asp Thr
                20                  25                  30

Tyr Ile His Trp Val Arg Gln Ala Arg Gly Gln Arg Leu Glu Trp Ile
            35                  40                  45

Gly Arg Phe Asp Pro Val Asn Val Asn Thr Arg Tyr Asp Ser Arg Phe
    50                  55                  60

Arg Gly Arg Val Thr Ile Thr Ser Asp Ala Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ser Arg Ser Tyr Tyr Asn Gly Arg Arg Phe Thr Tyr Trp Gly Gln
            100                 105                 110

Gly Thr Leu Val Thr Val Ser Ser
            115                 120

<210> SEQ ID NO 52
<211> LENGTH: 113
<212> TYPE: PRT
<213> ORGANISM: Artificial Sequence
<220> FEATURE:
<223> OTHER INFORMATION: Composite Human Light Chain

<400> SEQUENCE: 52

Asp Ile Val Met Thr Gln Ser Pro Asp Ser Leu Thr Val Ser Leu Gly
1               5                   10                  15

Glu Arg Ala Thr Ile Asn Cys Lys Ala Ser Gln Ser Leu Leu Ser Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Thr Gly Ser Gly Ser Gly Thr Phe Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Asn Tyr Pro Phe Thr Phe Gly Gln Gly Thr Lys Leu Glu Ile
            100                 105                 110

Lys

<210> SEQ ID NO 53
<211> LENGTH: 113
<212> TYPE: PRT
<213> ORGANISM: Artificial Sequence
<220> FEATURE:
<223> OTHER INFORMATION: Composite Human Light Chain

<400> SEQUENCE: 53

Asp Ile Val Met Thr Gln Ser Pro Ser Ser Leu Thr Ala Ser Val Gly
1               5                   10                  15

Asp Arg Val Thr Ile Thr Cys Lys Ala Ser Gln Ser Leu Leu Ser Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Thr Gly Ser Gly Ser Gly Thr Phe Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Asn Tyr Pro Phe Thr Phe Gly Gln Gly Thr Lys Leu Glu Ile
            100                 105                 110

Lys

<210> SEQ ID NO 54
<211> LENGTH: 113
<212> TYPE: PRT
```

```
<213> ORGANISM: Artificial Sequence
<220> FEATURE:
<223> OTHER INFORMATION: Composite Human Light Chain

<400> SEQUENCE: 54

Asp Ile Val Met Thr Gln Ser Pro Ser Ser Leu Thr Ala Ser Val Gly
1               5                   10                  15

Asp Arg Val Thr Ile Thr Cys Lys Ala Ser Gln Ser Leu Leu Ser Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Asn Tyr Pro Phe Thr Phe Gly Gln Gly Thr Lys Leu Glu Ile
            100                 105                 110

Lys

<210> SEQ ID NO 55
<211> LENGTH: 359
<212> TYPE: DNA
<213> ORGANISM: Artificial Sequence
<220> FEATURE:
<223> OTHER INFORMATION: Composite Human Heavy Chain

<400> SEQUENCE: 55
gaggttcagt tggtgcagtc tggggcagag cttaagaagc caggggcctc agtcaaggtg        60
tcctgtacag cttctggttt caacattaaa gacacctata acattgggtg aggcaggccc       120
ctggacagcg cctggagtgg attggaaggt ttgatcctgt gaatgttaat actagatatg       180
actcgcggtt ccggggcagg gccactataa catcagacgc atccaccaat acagcctaca       240
tggagctcag cagcctgaga tctgaggaca ctgccgtcta ttactgttct aggtcttatt       300
acaacggtag aagacgcttt acttactggg gccaagggac tctggtcact gtctcttca        359

<210> SEQ ID NO 56
<211> LENGTH: 339
<212> TYPE: DNA
<213> ORGANISM: Artificial Sequence
<220> FEATURE:
<223> OTHER INFORMATION: Composite human light chain

<400> SEQUENCE: 56
gacattgtga tgacacagtc tccagactcc ctgactgtgt cactgggaga gagggccact        60
atcaactgca aggccagtca gagtctgtta agcagtggaa atcaaaagaa ctacttgacc       120
tggtaccaac agaaaccagg gcagcctcct aaattgttga tctactgggc atctattagg       180
gaatctgggg tccctgatcg cttcacaggc agtggatctg gaacattttt cactctcacc       240
atcagtagtc tgcaggctga agacgtggca gtgtattact gtcagaatga ttataattat       300
ccattcacat tcggccaggg gacaaagttg gagataaaa                              339

<210> SEQ ID NO 57
<211> LENGTH: 360
<212> TYPE: DNA
<213> ORGANISM: Artificial Sequence
<220> FEATURE:
<223> OTHER INFORMATION: Composite human heavy chain
```

```
<400> SEQUENCE: 57
gaggttcagt tggtgcagtc tggggcagag gtgaagaagc aggggcctc  agtcaaggtg      60 tcctgtacag cttctggttt caacattaaa gacacctata tacattgggt gaggcaggcc     120
aggggacagc gcctggagtg gattggaagg tttgatcctg tgaatgttaa tactagatat     180
gactcgcggt tccggggcag ggccactata acatcagacg catccaccaa tacagcctac     240
atggagctca gcagcctgag atctgaggac actgccgtct attactgttc taggtcttat     300
tacaacggta aagacgctt  tacttactgg ggccaaggga ctctggtcac tgtctcttca     360

<210> SEQ ID NO 58
<211> LENGTH: 360
<212> TYPE: DNA
<213> ORGANISM: Artificial Sequence
<220> FEATURE:
<223> OTHER INFORMATION: Composite human heavy chain

<400> SEQUENCE: 58
caggttcagt tggtgcagtc tggggcagag gtgaagaagc aggggcctc  agtcaaggtg      60 tcctgtacag cttctggttt caacattaaa gacacctata tacattgggt gaggcaggcc     120
aggggacagc gcctggagtg gattggaagg tttgatcctg tgaatgttaa tactagatat     180
gactcgcggt tccggggcag ggccactata acatcagacg catccaccaa tacagcctac     240
atggagctca gcagcctgag atctgaggac actgccgtct attactgttc taggtcttat     300
tacaacggta aagacgctt  tacttactgg ggccaaggga ctctggtcac tgtctcttca     360

<210> SEQ ID NO 59
<211> LENGTH: 360
<212> TYPE: DNA
<213> ORGANISM: Artificial Sequence
<220> FEATURE:
<223> OTHER INFORMATION: Composite human heavy chain

<400> SEQUENCE: 59
caggttcagt tggtgcagtc tggggcagag gtgaagaagc aggggcctc  agtcaaggtg      60 tcctgtacag cttctggttt caacattaaa gacacctata tacattgggt gaggcaggcc     120
aggggacagc gcctggagtg gattggaagg tttgatcctg tgaatgttaa tactagatat     180
gactcgcggt tccggggcag ggtgactata acatcagacg catccaccaa tacagcctac     240
atggagctca gcagcctgag atctgaggac actgccgtct attactgttc taggtcttat     300
tacaacggta aagacgctt  tacttactgg ggccaaggga ctctggtcac tgtctcttca     360

<210> SEQ ID NO 60
<211> LENGTH: 360
<212> TYPE: DNA
<213> ORGANISM: Artificial Sequence
<220> FEATURE:
<223> OTHER INFORMATION: Composite human heavy chain

<400> SEQUENCE: 60
caggttcagt tggtgcagtc tggggcagag gtgaagaagc aggggcctc  agtcaaggtg      60 tcctgtacag cttctggttt caacattaaa gacacctata tacattgggt gaggcaggcc     120
aggggacagc gcctggagtg gattggaagg tttgatcctg tgaatgttaa tactagatat     180
gactcgcggt tccggggcag ggtgactata acatcagacg catccaccag cacagcctac     240
atggagctca gcagcctgag atctgaggac actgccgtct attactgttc taggtcttat     300
tacaacggta aagacgctt  tacttactgg ggccaaggga ctctggtcac tgtctcttca     360
```

<210> SEQ ID NO 61
<211> LENGTH: 339
<212> TYPE: DNA
<213> ORGANISM: Artificial Sequence
<220> FEATURE:
<223> OTHER INFORMATION: Composite human light chain

<400> SEQUENCE: 61

```
gacattgtga tgacacagtc tccatcctcc ctgactgcct cagtgggaga cagggtgact      60
atcacctgca aggccagtca gagtctgtta agcagtggaa atcaaaagaa ctacttgacc     120
tggtaccaac agaaaccagg gcagcctcct aaattgttga tctactgggc atctattagg    180
gaatctgggg tccctgatcg cttcacaggc agtggatctg gaacattttt cactctcacc    240
atcagtagtc tgcaggctga agacgtggca gtgtattact gtcagaatga ttataattat    300
ccattcacat tcggccaggg gacaaagttg gagataaaa                          339
```

<210> SEQ ID NO 62
<211> LENGTH: 339
<212> TYPE: DNA
<213> ORGANISM: Artificial Sequence
<220> FEATURE:
<223> OTHER INFORMATION: Composite human light chain

<400> SEQUENCE: 62

```
gacattgtga tgacacagtc tccatcctcc ctgactgcct cagtgggaga cagggtgact      60
atcacctgca aggccagtca gagtctgtta agcagtggaa atcaaaagaa ctacttgacc     120
tggtaccaac agaaaccagg gcagcctcct aaattgttga tctactgggc atctattagg    180
gaatctgggg tccctgatcg cttcagcggc agtggatctg gaacagactt cactctcacc    240
atcagtagtc tgcaggctga agacgtggca gtgtattact gtcagaatga ttataattat    300
ccattcacat tcggccaggg gacaaagttg gagataaaa                          339
```

<210> SEQ ID NO 63
<211> LENGTH: 39
<212> TYPE: DNA
<213> ORGANISM: Artificial Sequence
<220> FEATURE:
<223> OTHER INFORMATION: Primer

<400> SEQUENCE: 63

```
gatcacgcgt gtccactccg aagtgcagct ggtggagtc                            39
```

<210> SEQ ID NO 64
<211> LENGTH: 33
<212> TYPE: DNA
<213> ORGANISM: Artificial Sequence
<220> FEATURE:
<223> OTHER INFORMATION: Priner

<400> SEQUENCE: 64

```
gtacaagctt acctgaggag acggtgactg agg                                  33
```

<210> SEQ ID NO 65
<211> LENGTH: 35
<212> TYPE: DNA
<213> ORGANISM: Artificial Sequence
<220> FEATURE:
<223> OTHER INFORMATION: Primer

<400> SEQUENCE: 65

```
catggcgcgc gatgtgacat ccagatgact cagtc                                35
```

<210> SEQ ID NO 66
<211> LENGTH: 63
<212> TYPE: DNA
<213> ORGANISM: Artificial Sequence
<220> FEATURE:
<223> OTHER INFORMATION: Primer

<400> SEQUENCE: 66
tgcgggatcc aactgaggaa gcaaagttta aattctactc acgtctcagc tccagcttgg     60
tcc                                                                  63

<210> SEQ ID NO 67
<211> LENGTH: 22
<212> TYPE: PRT
<213> ORGANISM: Homo sapiens

<400> SEQUENCE: 67

Gln Val Gln Leu Val Gln Ser Gly Ala Glu Val Lys Lys Pro Gly Ala
1               5                   10                  15

Ser Val Lys Val Ser Cys
            20

<210> SEQ ID NO 68
<211> LENGTH: 9
<212> TYPE: PRT
<213> ORGANISM: Homo sapiens

<400> SEQUENCE: 68

Ser Val Lys Val Ser Cys Thr Ala Ser
1               5

<210> SEQ ID NO 69
<211> LENGTH: 17
<212> TYPE: PRT
<213> ORGANISM: Homo sapiens

<400> SEQUENCE: 69

Ala Ser Gly Phe Asn Ile Lys Asp Thr Tyr Ile His Trp Val Arg Gln
1               5                   10                  15

Ala

<210> SEQ ID NO 70
<211> LENGTH: 11
<212> TYPE: PRT
<213> ORGANISM: Homo sapiens

<400> SEQUENCE: 70

Ala Arg Gly Gln Arg Leu Glu Trp Ile Gly Arg
1               5                   10

<210> SEQ ID NO 71
<211> LENGTH: 5
<212> TYPE: PRT
<213> ORGANISM: Homo sapiens

<400> SEQUENCE: 71

Gly Arg Phe Asp Pro
1               5

<210> SEQ ID NO 72
<211> LENGTH: 4
<212> TYPE: PRT
<213> ORGANISM: Homo sapiens

```
<400> SEQUENCE: 72

Val Asn Val Asn
1

<210> SEQ ID NO 73
<211> LENGTH: 4
<212> TYPE: PRT
<213> ORGANISM: Homo sapiens

<400> SEQUENCE: 73

Asn Thr Arg Tyr
1

<210> SEQ ID NO 74
<211> LENGTH: 2
<212> TYPE: PRT
<213> ORGANISM: Homo sapiens

<400> SEQUENCE: 74

Asp Ser
1

<210> SEQ ID NO 75
<211> LENGTH: 6
<212> TYPE: PRT
<213> ORGANISM: Homo sapiens

<400> SEQUENCE: 75

Arg Phe Arg Gly Arg Val
1               5

<210> SEQ ID NO 76
<211> LENGTH: 8
<212> TYPE: PRT
<213> ORGANISM: Homo sapiens

<400> SEQUENCE: 76

Phe Arg Gly Arg Val Thr Ile Thr
1               5

<210> SEQ ID NO 77
<211> LENGTH: 14
<212> TYPE: PRT
<213> ORGANISM: Homo sapiens

<400> SEQUENCE: 77

Arg Val Thr Ile Thr Ser Asp Ala Ser Thr Asn Thr Ala Tyr
1               5                   10

<210> SEQ ID NO 78
<211> LENGTH: 19
<212> TYPE: PRT
<213> ORGANISM: Homo sapiens

<400> SEQUENCE: 78

Thr Ala Tyr Met Glu Leu Ser Ser Leu Arg Ser Glu Asp Thr Ala Val
1               5                   10                  15

Tyr Tyr Cys

<210> SEQ ID NO 79
<211> LENGTH: 10
<212> TYPE: PRT
<213> ORGANISM: Homo sapiens
```

```
<400> SEQUENCE: 79

Glu Asp Thr Ala Val Tyr Tyr Cys Ser Arg
1               5                   10

<210> SEQ ID NO 80
<211> LENGTH: 4
<212> TYPE: PRT
<213> ORGANISM: Homo sapiens

<400> SEQUENCE: 80

Arg Ser Tyr Tyr
1

<210> SEQ ID NO 81
<211> LENGTH: 3
<212> TYPE: PRT
<213> ORGANISM: Homo sapiens

<400> SEQUENCE: 81

Tyr Asn Gly
1

<210> SEQ ID NO 82
<211> LENGTH: 3
<212> TYPE: PRT
<213> ORGANISM: Homo sapiens

<400> SEQUENCE: 82

Gly Arg Arg
1

<210> SEQ ID NO 83
<211> LENGTH: 2
<212> TYPE: PRT
<213> ORGANISM: Homo sapiens

<400> SEQUENCE: 83

Arg Arg
1

<210> SEQ ID NO 84
<211> LENGTH: 3
<212> TYPE: PRT
<213> ORGANISM: Homo sapiens

<400> SEQUENCE: 84

Phe Thr Tyr
1

<210> SEQ ID NO 85
<211> LENGTH: 12
<212> TYPE: PRT
<213> ORGANISM: Homo sapiens

<400> SEQUENCE: 85

Tyr Trp Gly Gln Gly Thr Leu Val Thr Val Ser Ser
1               5                   10

<210> SEQ ID NO 86
<211> LENGTH: 24
<212> TYPE: PRT
<213> ORGANISM: Homo sapiens

<400> SEQUENCE: 86

Asp Ile Val Met Thr Gln Ser Pro Asp Ser Leu Thr Val Ser Leu Gly
```

```
                1               5                  10                 15

Glu Arg Ala Thr Ile Asn Cys Lys
                20

<210> SEQ ID NO 87
<211> LENGTH: 6
<212> TYPE: PRT
<213> ORGANISM: Homo sapiens

<400> SEQUENCE: 87

Cys Lys Ala Ser Gln Ser
1               5

<210> SEQ ID NO 88
<211> LENGTH: 5
<212> TYPE: PRT
<213> ORGANISM: Homo sapiens

<400> SEQUENCE: 88

Ser Gln Ser Leu Leu
1               5

<210> SEQ ID NO 89
<211> LENGTH: 3
<212> TYPE: PRT
<213> ORGANISM: Homo sapiens

<400> SEQUENCE: 89

Leu Ser Ser
1

<210> SEQ ID NO 90
<211> LENGTH: 3
<212> TYPE: PRT
<213> ORGANISM: Homo sapiens

<400> SEQUENCE: 90

Gly Asn Gln
1

<210> SEQ ID NO 91
<211> LENGTH: 23
<212> TYPE: PRT
<213> ORGANISM: Homo sapiens

<400> SEQUENCE: 91

Lys Asn Tyr Leu Thr Trp Tyr Gln Gln Lys Pro Gly Gln Pro Pro Lys
1               5                  10                 15

Leu Leu Ile Tyr Trp Ala Ser
                20

<210> SEQ ID NO 92
<211> LENGTH: 28
<212> TYPE: PRT
<213> ORGANISM: Homo sapiens

<400> SEQUENCE: 92

Trp Tyr Gln Gln Lys Pro Gly Gln Pro Pro Lys Leu Leu Ile Tyr Trp
1               5                  10                 15

Ala Ser Ile Arg Glu Ser Gly Val Pro Asp Arg Phe
                20                  25

<210> SEQ ID NO 93
<211> LENGTH: 14
```

```
<212> TYPE: PRT
<213> ORGANISM: Homo sapiens

<400> SEQUENCE: 93

Ser Gly Val Pro Asp Arg Phe Thr Gly Ser Gly Ser Gly Thr
1               5                   10

<210> SEQ ID NO 94
<211> LENGTH: 13
<212> TYPE: PRT
<213> ORGANISM: Homo sapiens

<400> SEQUENCE: 94

Gly Ser Gly Ser Gly Thr Phe Phe Thr Leu Thr Ile Ser
1               5                   10

<210> SEQ ID NO 95
<211> LENGTH: 19
<212> TYPE: PRT
<213> ORGANISM: Homo sapiens

<400> SEQUENCE: 95

Phe Thr Leu Thr Ile Ser Ser Leu Gln Ala Glu Asp Val Ala Val Tyr
1               5                   10                  15

Tyr Cys Gln

<210> SEQ ID NO 96
<211> LENGTH: 5
<212> TYPE: PRT
<213> ORGANISM: Homo sapiens

<400> SEQUENCE: 96

Tyr Tyr Cys Gln Asn
1               5

<210> SEQ ID NO 97
<211> LENGTH: 5
<212> TYPE: PRT
<213> ORGANISM: Homo sapiens

<400> SEQUENCE: 97

Asp Tyr Asn Tyr Pro
1               5

<210> SEQ ID NO 98
<211> LENGTH: 5
<212> TYPE: PRT
<213> ORGANISM: Homo sapiens

<400> SEQUENCE: 98

Pro Phe Thr Phe Gly
1               5

<210> SEQ ID NO 99
<211> LENGTH: 11
<212> TYPE: PRT
<213> ORGANISM: Homo sapiens

<400> SEQUENCE: 99

Thr Phe Gly Gln Gly Thr Lys Leu Glu Ile Lys
1               5                   10

<210> SEQ ID NO 100
<211> LENGTH: 11
<212> TYPE: PRT
```

<213> ORGANISM: Homo sapiens

<400> SEQUENCE: 100

Asp Ile Val Met Thr Gln Ser Pro Ser Ser Leu
1               5                   10

<210> SEQ ID NO 101
<211> LENGTH: 20
<212> TYPE: PRT
<213> ORGANISM: Homo sapiens

<400> SEQUENCE: 101

Met Thr Gln Ser Pro Ser Ser Leu Thr Ala Ser Val Gly Asp Arg Val
1               5                   10                  15

Thr Ile Thr Cys
            20

<210> SEQ ID NO 102
<211> LENGTH: 6
<212> TYPE: PRT
<213> ORGANISM: Homo sapiens

<400> SEQUENCE: 102

Cys Lys Ala Ser Gln Ser
1               5

<210> SEQ ID NO 103
<211> LENGTH: 5
<212> TYPE: PRT
<213> ORGANISM: Homo sapiens

<400> SEQUENCE: 103

Ser Gln Ser Leu Leu
1               5

<210> SEQ ID NO 104
<211> LENGTH: 3
<212> TYPE: PRT
<213> ORGANISM: Homo sapiens

<400> SEQUENCE: 104

Leu Ser Ser
1

<210> SEQ ID NO 105
<211> LENGTH: 3
<212> TYPE: PRT
<213> ORGANISM: Homo sapiens

<400> SEQUENCE: 105

Gly Asn Gln
1

<210> SEQ ID NO 106
<211> LENGTH: 23
<212> TYPE: PRT
<213> ORGANISM: Homo sapiens

<400> SEQUENCE: 106

Lys Asn Tyr Leu Thr Trp Tyr Gln Gln Lys Pro Gly Gln Pro Pro Lys
1               5                   10                  15

Leu Leu Ile Tyr Trp Ala Ser
            20

```
<210> SEQ ID NO 107
<211> LENGTH: 28
<212> TYPE: PRT
<213> ORGANISM: Homo sapiens

<400> SEQUENCE: 107

Trp Tyr Gln Gln Lys Pro Gly Gln Pro Pro Lys Leu Leu Ile Tyr Trp
1               5                   10                  15

Ala Ser Ile Arg Glu Ser Gly Val Pro Asp Arg Phe
            20                  25

<210> SEQ ID NO 108
<211> LENGTH: 14
<212> TYPE: PRT
<213> ORGANISM: Homo sapiens

<400> SEQUENCE: 108

Ser Gly Val Pro Asp Arg Phe Thr Gly Ser Gly Ser Gly Thr
1               5                   10

<210> SEQ ID NO 109
<211> LENGTH: 13
<212> TYPE: PRT
<213> ORGANISM: Homo sapiens

<400> SEQUENCE: 109

Gly Ser Gly Ser Gly Thr Phe Phe Thr Leu Thr Ile Ser
1               5                   10

<210> SEQ ID NO 110
<211> LENGTH: 19
<212> TYPE: PRT
<213> ORGANISM: Homo sapiens

<400> SEQUENCE: 110

Phe Thr Leu Thr Ile Ser Ser Leu Gln Ala Glu Asp Val Ala Val Tyr
1               5                   10                  15

Tyr Cys Gln

<210> SEQ ID NO 111
<211> LENGTH: 5
<212> TYPE: PRT
<213> ORGANISM: Homo sapiens

<400> SEQUENCE: 111

Tyr Tyr Cys Gln Asn
1               5

<210> SEQ ID NO 112
<211> LENGTH: 5
<212> TYPE: PRT
<213> ORGANISM: Homo sapiens

<400> SEQUENCE: 112

Asp Tyr Asn Tyr Pro
1               5

<210> SEQ ID NO 113
<211> LENGTH: 5
<212> TYPE: PRT
<213> ORGANISM: Homo sapiens

<400> SEQUENCE: 113

Pro Phe Thr Phe Gly
1               5
```

<210> SEQ ID NO 114
<211> LENGTH: 11
<212> TYPE: PRT
<213> ORGANISM: Homo sapiens

<400> SEQUENCE: 114

Thr Phe Gly Gln Gly Thr Lys Leu Glu Ile Lys
1               5                   10

<210> SEQ ID NO 115
<211> LENGTH: 22
<212> TYPE: PRT
<213> ORGANISM: Homo sapiens

<400> SEQUENCE: 115

Gln Val Gln Leu Val Gln Ser Gly Ala Glu Val Lys Lys Pro Gly Ala
1               5                   10                  15

Ser Val Lys Val Ser Cys
            20

<210> SEQ ID NO 116
<211> LENGTH: 9
<212> TYPE: PRT
<213> ORGANISM: Homo sapiens

<400> SEQUENCE: 116

Ser Val Lys Val Ser Cys Thr Ala Ser
1               5

<210> SEQ ID NO 117
<211> LENGTH: 17
<212> TYPE: PRT
<213> ORGANISM: Homo sapiens

<400> SEQUENCE: 117

Ala Ser Gly Phe Asn Ile Lys Asp Thr Tyr Ile His Trp Val Arg Gln
1               5                   10                  15

Ala

<210> SEQ ID NO 118
<211> LENGTH: 11
<212> TYPE: PRT
<213> ORGANISM: Homo sapiens

<400> SEQUENCE: 118

Ala Arg Gly Gln Arg Leu Glu Trp Ile Gly Arg
1               5                   10

<210> SEQ ID NO 119
<211> LENGTH: 5
<212> TYPE: PRT
<213> ORGANISM: Homo sapiens

<400> SEQUENCE: 119

Gly Arg Phe Asp Pro
1               5

<210> SEQ ID NO 120
<211> LENGTH: 4
<212> TYPE: PRT
<213> ORGANISM: Homo sapiens

<400> SEQUENCE: 120

Val Asn Val Asn
1

<210> SEQ ID NO 121
<211> LENGTH: 4
<212> TYPE: PRT
<213> ORGANISM: Homo sapiens

<400> SEQUENCE: 121

Asn Thr Arg Tyr
1

<210> SEQ ID NO 122
<211> LENGTH: 2
<212> TYPE: PRT
<213> ORGANISM: Homo sapiens

<400> SEQUENCE: 122

Asp Ser
1

<210> SEQ ID NO 123
<211> LENGTH: 6
<212> TYPE: PRT
<213> ORGANISM: Homo sapiens

<400> SEQUENCE: 123

Arg Phe Arg Gly Arg Val
1               5

<210> SEQ ID NO 124
<211> LENGTH: 8
<212> TYPE: PRT
<213> ORGANISM: Homo sapiens

<400> SEQUENCE: 124

Phe Arg Gly Arg Val Thr Ile Thr
1               5

<210> SEQ ID NO 125
<211> LENGTH: 14
<212> TYPE: PRT
<213> ORGANISM: Homo sapiens

<400> SEQUENCE: 125

Arg Val Thr Ile Thr Ser Asp Ala Ser Thr Asn Thr Ala Tyr
1               5                   10

<210> SEQ ID NO 126
<211> LENGTH: 19
<212> TYPE: PRT
<213> ORGANISM: Homo sapiens

<400> SEQUENCE: 126

Thr Ala Tyr Met Glu Leu Ser Ser Leu Arg Ser Glu Asp Thr Ala Val
1               5                   10                  15

Tyr Tyr Cys

<210> SEQ ID NO 127
<211> LENGTH: 10
<212> TYPE: PRT
<213> ORGANISM: Homo sapiens

<400> SEQUENCE: 127

Glu Asp Thr Ala Val Tyr Tyr Cys Ser Arg

```
<210> SEQ ID NO 128
<211> LENGTH: 4
<212> TYPE: PRT
<213> ORGANISM: Homo sapiens

<400> SEQUENCE: 128

Arg Ser Tyr Tyr
1

<210> SEQ ID NO 129
<211> LENGTH: 3
<212> TYPE: PRT
<213> ORGANISM: Homo sapiens

<400> SEQUENCE: 129

Tyr Asn Gly
1

<210> SEQ ID NO 130
<211> LENGTH: 3
<212> TYPE: PRT
<213> ORGANISM: Homo sapiens

<400> SEQUENCE: 130

Gly Arg Arg
1

<210> SEQ ID NO 131
<211> LENGTH: 2
<212> TYPE: PRT
<213> ORGANISM: Homo sapiens

<400> SEQUENCE: 131

Arg Arg
1

<210> SEQ ID NO 132
<211> LENGTH: 3
<212> TYPE: PRT
<213> ORGANISM: Homo sapiens

<400> SEQUENCE: 132

Phe Thr Tyr
1

<210> SEQ ID NO 133
<211> LENGTH: 12
<212> TYPE: PRT
<213> ORGANISM: Homo sapiens

<400> SEQUENCE: 133

Tyr Trp Gly Gln Gly Thr Leu Val Thr Val Ser Ser
1               5                   10
```